United States Patent
Akoulitchev et al.

(10) Patent No.: US 12,006,547 B2
(45) Date of Patent: Jun. 11, 2024

(54) DETECTION OF CHROMOSOME INTERACTIONS AS INDICATIVE OF AMYOTROPHIC LATERAL SCLEROSIS

(71) Applicant: Oxford BioDynamics PLC, Oxford (GB)

(72) Inventors: Alexandre Akoulitchev, Oxford (GB); Aroul Selvam Ramadass, Oxford (GB); Ewan Hunter, Oxford (GB); Matthew Salter, Oxford (GB)

(73) Assignee: Oxford BioDynamics PLC, Oxford (GB)

( * ) Notice: Subject to any disclaimer, the term of this patent is extended or adjusted under 35 U.S.C. 154(b) by 99 days.

(21) Appl. No.: 16/652,959

(22) PCT Filed: Oct. 1, 2018

(86) PCT No.: PCT/GB2018/052808
§ 371 (c)(1),
(2) Date: Apr. 1, 2020

(87) PCT Pub. No.: WO2019/069067
PCT Pub. Date: Apr. 11, 2019

(65) Prior Publication Data
US 2020/0407790 A1 Dec. 31, 2020

Related U.S. Application Data

(60) Provisional application No. 62/566,756, filed on Oct. 2, 2017.

(51) Int. Cl.
*C12Q 1/6883* (2018.01)

(52) U.S. Cl.
CPC ..... *C12Q 1/6883* (2013.01); *C12Q 2600/106* (2013.01); *C12Q 2600/118* (2013.01); *C12Q 2600/156* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

2010/0075861 A1* 3/2010 De Laat ............... C12Q 1/6809
506/26

FOREIGN PATENT DOCUMENTS

| WO | WO2016207647 | * 12/2006 |
| WO | 2009/147386 A1 | 12/2009 |
| WO | 2016/207653 A1 | 12/2016 |
| WO | 2016/207661 A1 | 12/2016 |
| WO | 2017/001568 A1 | 1/2017 |
| WO | 2018/115802 A1 | 6/2018 |

OTHER PUBLICATIONS

Lim et al. 2017. J Neurological Sciences. 381: 616, Abstract 1706 (Year: 2017).*
Jakub et al Melanoma Research. 2015. 25: 408-411 (Year: 2015).*
(Continued)

*Primary Examiner* — Carla J Myers
(74) *Attorney, Agent, or Firm* — Seed IP Law Group LLP

(57) ABSTRACT

A process for analysing chromosome regions and interactions relating to ALS and Huntington's disease.

2 Claims, 5 Drawing Sheets

Specification includes a Sequence Listing.

(56) References Cited

OTHER PUBLICATIONS

Stadhouders et al Nature Protocols. 2013. 8(3): 509-524 (Year: 2013).*
Crutchley et al Biomarkers in Medicine. 2010. 4(4): 611-629 (Year: 2010).*
GeneCards for the NEFH gene, available via URL: <genecards.org/cgi-bin/carddisp.pl?gene=NEFH>, printed Jun. 29, 2023 (Year: 2023).*
Hughes, "Oxford BioDynamics expands biomarker discovery programme for ALS", European Pharmaceutical Manufacturer, Jan. 18, 2016.
Krause et al, "Junctophilin 3 (JPH3) expansion mutations causing Huntington disease like 2 (HDL2) are common in South African patients with African ancestry and a Huntington disease phenotype: JPH3 Mutations Causing HD Phenotype in Africa", American Journal of Medical Genetics Part B: Neuropsychiatric Genetics, (Jun. 16, 2015), vol. 168, No. 7.
Lim et al., "Epigenetic signatures and early detection of neurodegenerative diseases: Development of stratifying biomarker for ALS in Asian cohorts." World Congress of Neurology; Sep. 16-21, 2017; Kyoto, Japan.
Poesen, "The Chromosomal Conformation Signature: a New Kid on the Block in ALS Biomarker Research?", EBioMedicine, vol. 33, Jul. 2018, pp. 6-7.
Salter et al, "Initial Identification of a Blood-Based Chromosome Conformation Signature for Aiding in the Diagnosis of Amyotrophic Lateral Sclerosis"; EBioMedicine, vol. 33, Jun. 2018, pp. 169-184.
Salter et al, "A Chromosomal Conformation Signature for a Priori Prediction of ALS Progression Subtypes", 28th International Symposium on ALS/MND; Dec. 8-10, 2017; Boston, USA.
Salter et al, "Chromosome conformation signatures as a clinical tool for diagnosis, prognosis and disease understanding in ALS", ENCALS Jun. 20-22, 2018, Oxford, UK.
Westra et al, "A Prospective Study of Two Distinct Epigenetic Signatures for ALS Diagnosis and Prognosis"; 16th Annual Northeast Amyotrophic Lateral Sclerosis Meeting; Oct. 3-5, 2017; Clearwater Beach, Florida, USA.
Q&A with Dr Alexandre Akoulitchev Chief Scientific Officer at Oxford Biodynamics PLC (Mar. 21, 2018).
Oxford Biodynamics Press Release of Mar. 16, 2018.
Oxford Biodynamics Press Release of Jun. 26, 2018.
Oxford Biodynamics Press Release of Dec. 16, 2014.
Oxford Biodynamics Press Release of Oct. 11, 2017.
Oxford Biodynamics Press Release of Jun. 13, 2017.

* cited by examiner

DETECTION OF CHROMOSOME INTERACTIONS AS INDICATIVE OF AMYOTROPHIC LATERAL SCLEROSIS

REFERENCE TO AN ELECTRONIC SEQUENCE LISTING

The contents of the electronic sequence listing (Sequence_Listing.xm.; Size: 25.2 KB; and Date of Creation: Oct. 25, 2022) are herein incorporated by reference in its entirety.

Field of the Invention

The invention relates to detecting chromosome interactions.

BACKGROUND OF THE INVENTION

Biomarkers allow disease characteristics to be identified. The present commonly used biomarkers include RNA expression patterns and protein markers.

SUMMARY OF THE INVENTION

Specific Chromosome Conformation Signatures (CCSs) at loci either exist or are absent due to the regulatory epigenetic control settings associated with pathology or treatment. CCSs have mild off-rates and when representing a particular phenotype or pathology, they will only change with a physiologically signalled transition to a new phenotype, or as a result of external intervention. In addition, the measurement of these events is binary, and so this read-out is in stark contrast to the continuum readout of varying levels of DNA methylation, histone modifications and most of the non-coding RNAs. The continuum read-out used for most molecular biomarkers to date offers a challenge to data analysis, in that the magnitude of change for particular biomarkers varies greatly from patient to patient, which causes problems for classification statistics when they are used to stratify cohorts of patients. These classification statistics are better-suited to using biomarkers that are absent of magnitude and offer just a "yes or no" binary score of phenotypic differences—signifying that chromosome conformation (EpiSwitch™) biomarkers are an excellent resource for potential diagnostic, prognostic and predictive biomarkers.

The inventors have identified regions of the genome where chromosomal interactions are relevant to amyotrophic lateral sclerosis (ALS) or Huntington's disease using an approach which allows identification of subgroups in a population. Accordingly, the invention provides a process for detecting a chromosome state which represents a subgroup in a population comprising determining whether a chromosome interaction is present or absent within a defined disease-associated region of the genome, wherein said disease is ALS or Huntington's disease. The chromosome interaction may optionally have been identified, or be identifiable (or derivable), by a method of determining which chromosomal interactions are relevant to a chromosome state corresponding to an ALS or Huntington's disease subgroup of the population, comprising contacting a first set of nucleic acids from subgroups with different states of the chromosome with a second set of index nucleic acids, and allowing complementary sequences to hybridise, wherein the nucleic acids in the first and second sets of nucleic acids represent a ligated product comprising sequences from both the chromosome regions that have come together in chromosomal interactions, and wherein the pattern of hybridisation between the first and second set of nucleic acids allows a determination of which chromosomal interactions are specific to a ALS or Huntington's disease subgroup. The ALS or Huntington's disease subgroup may relate to diagnosis (presence of ALS or Huntington's disease) or prognosis (for example rate of progress of ALS or Huntington's disease). Any of the specific relevant chromosome interactions (markers) described herein may be used as the basis of the invention, including combinations of markers.

The invention provides a process for detecting a chromosome state which represents a disease subgroup in a population comprising determining whether a chromosome interaction relating to that chromosome state is present or absent within a defined region of the genome, wherein said disease subgroup is an amyotrophic lateral sclerosis (ALS) subgroup; and wherein said chromosome interaction has optionally been identified by a method of determining which chromosomal interactions are relevant to a chromosome state corresponding to an ALS subgroup of the population, comprising contacting a first set of nucleic acids from subgroups with different states of the chromosome with a second set of index nucleic acids, and allowing complementary sequences to hybridise, wherein the nucleic acids in the first and second sets of nucleic acids represent a ligated product comprising sequences from both the chromosome regions that have come together in chromosomal interactions, and wherein the pattern of hybridisation between the first and second set of nucleic acids allows a determination of which chromosomal interactions are specific to an ALS subgroup; and wherein the chromosome interaction:

(i) is present in any one of the regions or genes listed in Table 1 or 5; and/or (ii) corresponds to any one of the chromosome interactions represented by any probe shown in Table 1 or 5, and/or (iii) corresponds to any one of the chromosome interactions shown in Table 10 or 11, and/or (iv) is present in a 4,000 base region which comprises or which flanks (i), (ii) or (iii).

The invention also provides a process for detecting a chromosome state which represents a disease subgroup in a population comprising determining whether a chromosome interaction relating to that chromosome state is present or absent within a defined region of the genome, wherein said disease subgroup is a Huntington's disease subgroup; and wherein said chromosome interaction has optionally been identified by a method of determining which chromosomal interactions are relevant to a chromosome state corresponding to an Huntington's disease subgroup of the population, comprising contacting a first set of nucleic acids from subgroups with different states of the chromosome with a second set of index nucleic acids, and allowing complementary sequences to hybridise, wherein the nucleic acids in the first and second sets of nucleic acids represent a ligated product comprising sequences from both the chromosome regions that have come together in chromosomal interactions, and wherein the pattern of hybridisation between the first and second set of nucleic acids allows a determination of which chromosomal interactions are specific to an Huntington's disease subgroup; and
wherein the chromosome interaction:
(i) is present in any one of the regions or genes listed in Table 12; and/or
(ii) corresponds to any one of the chromosome interactions represented by any probe shown in Table 12, and/or
(iii) corresponds to any one of the chromosome interactions represented in Table 12, and/or
(iii) is present in a 4,000 base region which comprises or which flanks (i), (ii) or (iii).

DETAILED DESCRIPTION OF THE INVENTION

The Process of the Invention

Figure 1:
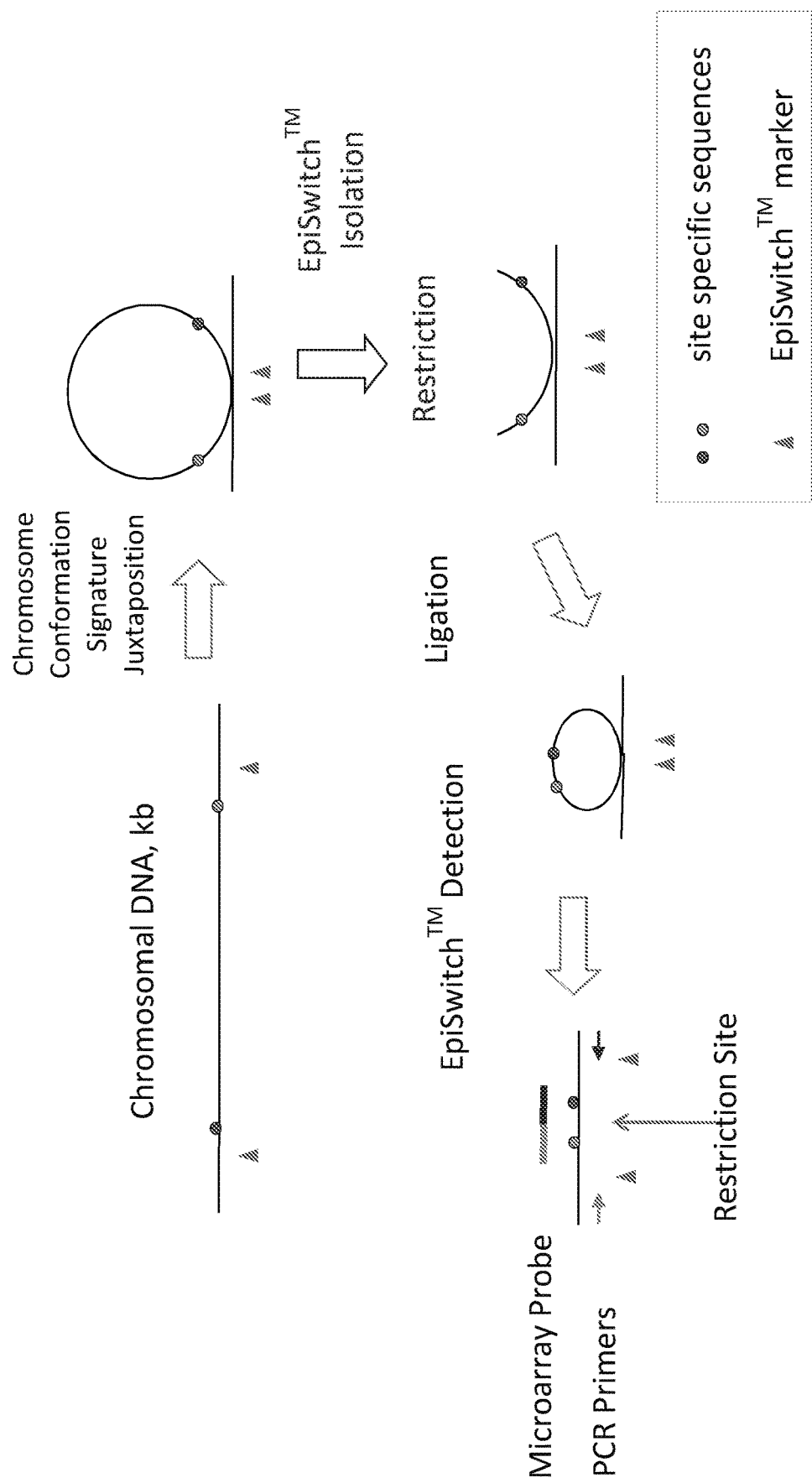
FIG. 1 shows how the chromosome interaction can be detected.

The process of the invention comprises a typing system for detecting chromosome interactions relevant to ALS or Huntington's disease. This typing may be performed using the EpiSwitch™ system mentioned herein which is based on cross-linking regions of chromosome which have come together in the chromosome interaction, subjecting the chromosomal DNA to cleavage and then ligating the nucleic acids present in the cross-linked entity to derive a ligated nucleic acid with sequence from both the regions which formed the chromosomal interaction. Detection of this ligated nucleic acid allows determination of the presence or absence of a particular chromosome interaction.

The chromosomal interactions may be identified using the above described method in which populations of first and second nucleic acids are used. These nucleic acids can also be generated using EpiSwitch™ technology.

The Epigenetic Interactions Relevant to the Invention

As used herein, the term 'epigenetic' and 'chromosome' interactions typically refers to interactions between distal regions of a chromosome, said interactions being dynamic and altering, forming or breaking depending upon the status of the region of the chromosome.

In particular processes of the invention chromosome interactions are detected by first generating a ligated nucleic acid that comprises sequence from both regions of the chromosomes that are part of the interactions. In such processes the regions can be cross-linked by any suitable means. In a preferred embodiment, the interactions are cross-linked using formaldehyde, but may also be cross-linked by any aldehyde, or D-Biotinoyl-e-aminocaproic acid-N-hydroxysuccinimide ester or Digoxigenin-3-O-methylcarbonyl-e-aminocaproic acid-N-hydroxysuccinimide ester. Para-formaldehyde can cross link DNA chains which are 4 Angstroms apart. Preferably the chromosome interactions are on the same chromosome and optionally 2 to 10 Angstroms apart.

The chromosome interaction may reflect the status of the region of the chromosome, for example, if it is being transcribed or repressed in response to change of the physiological conditions. Chromosome interactions which are specific to subgroups as defined herein have been found to be stable, thus providing a reliable means of measuring the differences between the two subgroups.

In addition, chromosome interactions specific to a characteristic (such as a disease condition) will normally occur early in a biological process, for example compared to other epigenetic markers such as methylation or changes to binding of histone proteins. Thus the process of the invention is able to detect early stages of a biological process. This allows early intervention (for example treatment) which may as a consequence be more effective. Furthermore there is little variation in the relevant chromosome interactions between individuals within the same subgroup. Detecting chromosome interactions is highly informative with up to 50 different possible interactions per gene, and so processes of the invention can interrogate 500,000 different interactions.

Preferred Marker Sets

Herein the term 'marker' or 'biomarker' refers to a specific chromosome interaction which can be detected (typed) in the invention. Specific markers are disclosed herein, any of which may be used in the invention. Further sets of markers may be used, for example in the combinations or numbers disclosed herein. The markers disclosed in the tables herein are preferred. These may be typed by any suitable method, for example the PCR or probe based methods disclosed herein, including a qPCR method. The markers are defined herein by location or by probe and/or primer sequences.

Location and Causes of Epigenetic Interactions

Epigenetic chromosomal interactions may overlap and include the regions of chromosomes shown to encode relevant or undescribed genes, but equally may be in intergenic regions. It should further be noted that the inventors have discovered that epigenetic interactions in all regions are equally important in determining the status of the chromosomal locus. These interactions are not necessarily in the coding region of a particular gene located at the locus and may be in intergenic regions.

The chromosome interactions which are detected in the invention could be caused by changes to the underlying DNA sequence, by environmental factors, DNA methylation, non-coding antisense RNA transcripts, non-mutagenic carcinogens, histone modifications, chromatin remodelling and specific local DNA interactions. The changes which lead to the chromosome interactions may be caused by changes to the underlying nucleic acid sequence, which themselves do not directly affect a gene product or the mode of gene expression. Such changes may be for example, SNPs within and/or outside of the genes, gene fusions and/or deletions of intergenic DNA, microRNA, and non-coding RNA. For example, it is known that roughly 20% of SNPs are in non-coding regions, and therefore the process as described is also informative in non-coding situation. In one embodiment the regions of the chromosome which come together to form the interaction are less than 5 kb, 3 kb, 1 kb, 500 base pairs or 200 base pairs apart on the same chromosome.

The chromosome interaction which is detected is preferably within any of the genes mentioned in Table 1 or 5. However it may also be upstream or downstream of the gene, for example up to 50,000, up to 30,000, up to 20,000, up to 10,000 or up to 5000 bases upstream or downstream from the gene or from the coding sequence.

Subgroups, Diagnosis and Personalised Treatment

The aim of the present invention is to permit detection of chromosome interactions relevant to an ALS or Huntington's disease subgroup. Therefore the process may or may not be used for diagnosis of ALS or Huntington's disease. The process may or may not be used for prognosis of ALS or Huntington's disease.

When the process is used for diagnosis of ALS the typing of markers relating to Table 1 are preferred (i.e. the specific disclosed markers and those in the genes, regions and flanking areas disclosed in Table 1). In one embodiment relating to diagnosis only markers relating to Table 1 are typed and no other markers. In other embodiments relating to diagnosis at least 1, 2, 3, 4, 5 or more markers relating to (for example as represented by the listed probe sequences) Table 5 are not typed.

When the process is used for prognosis the typing of markers relating to Table 5 are preferred (i.e. the specific disclosed markers and those in the genes, regions and flanking areas disclosed in Table 5). In one embodiment relating to prognosis only markers relating to Table 5 are typed and no other markers. In other embodiments relating to prognosis at least 1, 2, 3, 4, 5 or more markers relating to (for example as represented by the listed probe sequences) Table 1 are not typed.

Typically, 'prognosis' relates to progression of ALS, and allows individuals to be divided into rate of progression subgroups. Progression may be measured using an ALS-FRS-R score (ALS functional rating scale), and individuals may be classed as being above or below a certain value, for example above or below a 0.5 point decline per 30 days. This allows a predictive prognosis to be performed.

As used herein, a "subgroup" preferably refers to a population subgroup (a subgroup in a population), more preferably a subgroup in the population of a particular animal such as a particular eukaryote, or mammal (e.g. human, non-human, non-human primate, or rodent e.g. mouse or rat). Most preferably, a "subgroup" refers to a subgroup in the human population.

The invention includes detecting and treating particular subgroups in a population. The inventors have discovered that chromosome interactions differ between subsets (for example at least two subsets) in a given population. Identifying these differences will allow physicians to categorize their patients as a part of one subset of the population as described in the process. The invention therefore provides physicians with a process of personalizing medicine for the patient based on their epigenetic chromosome interactions.

In one embodiment subgroups (for example relating to prognosis) are defined by the ALS functional rating scale, for example as described in Cedarbaum, J. M., Stambler, N., Malta, E., Fuller, C., Hilt, D., Thurmond, B. and Nakanishi, A. (1999) The ALSFRS-R: a revised ALS functional rating scale that incorporates assessments of respiratory function. BDNF ALS Study Group (Phase III), Journal of the Neurological Sciences. 169(1-2), 13-21.

In one embodiment subgroups (for example relating to prognosis) are defined by forced vital capacity (FVC), for example as described in Talakad, N. S., Pradhan, C., Nalini, A., Thennarasu, K. and Raju T. R. (2009) Assessment of Pulmonary Function in Amyotrophic Lateral Sclerosis, *Indian J Chest Dis Allied Sci.* 51(2):87-91.

Generating Ligated Nucleic Acids

Certain embodiments of the invention utilise ligated nucleic acids, in particular ligated DNA. These comprise sequences from both of the regions that come together in a chromosome interaction and therefore provide information about the interaction. The EpiSwitch™ method described herein uses generation of such ligated nucleic acids to detect chromosome interactions.

Thus a process of the invention may comprise a step of generating ligated nucleic acids (e.g. DNA) by the following steps (including a method comprising these steps):
  (i) cross-linking of epigenetic chromosomal interactions present at the chromosomal locus, preferably in vitro;
  (ii) optionally isolating the cross-linked DNA from said chromosomal locus;
  (iii) subjecting said cross-linked DNA to cutting, for example by restriction digestion with an enzyme that cuts it at least once (in particular an enzyme that cuts at least once within said chromosomal locus);
  (iv) ligating said cross-linked cleaved DNA ends (in particular to form DNA loops); and
  (v) optionally identifying the presence of said ligated DNA and/or said DNA loops, in particular using techniques such as PCR (polymerase chain reaction), to identify the presence of a specific chromosomal interaction.

These steps may be carried out to detect the chromosome interactions for any embodiment mentioned herein, such as for determining whether the individual is part of an ALS or Huntington's disease subgroup. The steps may also be carried out to generate the first and/or second set of nucleic acids mentioned herein.

PCR (polymerase chain reaction) may be used to detect or identify the ligated nucleic acid, for example the size of the PCR product produced may be indicative of the specific chromosome interaction which is present, and may therefore be used to identify the status of the locus. In preferred embodiments at least 1, 2, 3, 4, 5, 6, 7 or 8 primers or primer pairs as shown in Table 2 or 7 are used in the PCR reaction. In other preferred embodiments at least 1, 2, 3, 4, 5, 6, 7 or 8 primers or primer pairs as shown in any other table are used in the PCR reaction The skilled person will be aware of numerous restriction enzymes which can be used to cut the DNA within the chromosomal locus of interest. It will be apparent that the particular enzyme used will depend upon the locus studied and the sequence of the DNA located therein. A non-limiting example of a restriction enzyme which can be used to cut the DNA as described in the present invention is TaqI.

Embodiments such as EpiSwitch™ Technology

The EpiSwitch™ Technology also relates to the use of microarray EpiSwitch™ marker data in the detection of epigenetic chromosome conformation signatures specific for phenotypes. Embodiments such as EpiSwitch™ which utilise ligated nucleic acids in the manner described herein have several advantages. They have a low level of stochastic noise, for example because the nucleic acid sequences from the first set of nucleic acids of the present invention either hybridise or fail to hybridise with the second set of nucleic acids. This provides a binary result permitting a relatively simple way to measure a complex mechanism at the epigenetic level. EpiSwitch™ technology also has fast processing time and low cost. In one embodiment the processing time is 3 hours to 6 hours.

Samples and Sample Treatment

The process of the invention will normally be carried out on a sample. The sample will normally contain DNA from the individual. It will normally contain cells. In one embodiment a sample is obtained by minimally invasive means, and may for example be a blood sample. DNA may be extracted and cut up with a standard restriction enzyme. This can pre-determine which chromosome conformations are retained and will be detected with the EpiSwitch™ platforms. Due to the synchronisation of chromosome interactions between tissues and blood, including horizontal transfer, a blood sample can be used to detect the chromosome interactions in tissues, such as tissues relevant to disease. For certain conditions, such as cancer, genetic noise due to mutations can affect the chromosome interaction 'signal' in the relevant tissues and therefore using blood is advantageous.

Properties of Nucleic Acids of the Invention

The invention relates to certain nucleic acids, such as the ligated nucleic acids which are described herein as being used or generated in the process of the invention. These may be the same as, or have any of the properties of, the first and second nucleic acids mentioned herein. The nucleic acids of the invention typically comprise two portions each comprising sequence from one of the two regions of the chromosome which come together in the chromosome interaction. Typically each portion is at least 8, 10, 15, 20, 30 or 40 nucleotides in length, for example 10 to 40 nucleotides in length. Preferred nucleic acids comprise sequence from any of the genes mentioned in any of the tables. Typically preferred nucleic acids comprise the specific probe sequences mentioned in Table 1 or 5; or fragments and/or homologues of such sequences. Other preferred nucleic acids comprise the specific probe sequences mentioned in Table 10, 11 or 12; or fragments and/or homologues of such sequences. Preferably the nucleic acids are DNA. It is understood that where a specific sequence is provided the invention may use the complementary sequence as required in the particular embodiment.

The primers shown in Table 2 or 7 may also be used in the invention as mentioned herein. In one embodiment primers are used which comprise any of: the sequences shown in Table 2 or 7; or fragments and/or homologues of any sequence shown in Table 2 or 7.

The Second Set of Nucleic Acids—the 'Index' Sequences

The second set of nucleic acid sequences has the function of being a set of index sequences, and is essentially a set of nucleic acid sequences which are suitable for identifying subgroup specific sequence. They can represents the 'background' chromosomal interactions and might be selected in some way or be unselected. They are in general a subset of all possible chromosomal interactions.

The second set of nucleic acids may be derived by any suitable process. They can be derived computationally or they may be based on chromosome interaction in individuals. They typically represent a larger population group than the first set of nucleic acids. In one particular embodiment, the second set of nucleic acids represents all possible epigenetic chromosomal interactions in a specific set of genes. In another particular embodiment, the second set of nucleic acids represents a large proportion of all possible epigenetic chromosomal interactions present in a population described herein. In one particular embodiment, the second set of nucleic acids represents at least 50% or at least 80% of epigenetic chromosomal interactions in at least 20, 50, 100 or 500 genes, for example in 20 to 100 or 50 to 500 genes.

The second set of nucleic acids typically represents at least 100 possible epigenetic chromosome interactions which modify, regulate or in any way mediate a disease state/phenotype in population. The second set of nucleic acids may represent chromosome interactions that affect a disease state (typically relevant to diagnosis or prognosis) in a species. The second set of nucleic acids typically comprises sequences representing epigenetic interactions both relevant and not relevant to an ALS subgroup. In one particular embodiment the second set of nucleic acids derive at least partially from naturally occurring sequences in a population, and are typically obtained by in silico processes. Said nucleic acids may further comprise single or multiple mutations in comparison to a corresponding portion of nucleic acids present in the naturally occurring nucleic acids. Mutations include deletions, substitutions and/or additions of one or more nucleotide base pairs. In one particular embodiment, the second set of nucleic acids may comprise sequence representing a homologue and/or orthologue with at least 70% sequence identity to the corresponding portion of nucleic acids present in the naturally occurring species. In another particular embodiment, at least 80% sequence identity or at least 90% sequence identity to the corresponding portion of nucleic acids present in the naturally occurring species is provided.

Properties of the Second Set of Nucleic Acids

In one particular embodiment, there are at least 100 different nucleic acid sequences in the second set of nucleic acids, preferably at least 1000, 2000 or 5000 different nucleic acids sequences, with up to 100,000, 1,000,000 or 10,000,000 different nucleic acid sequences. A typical number would be 100 to 1,000,000, such as 1,000 to 100,000 different nucleic acids sequences. All or at least 90% or at least 50% or these would correspond to different chromosomal interactions.

In one particular embodiment, the second set of nucleic acids represent chromosome interactions in at least 20 different loci or genes, preferably at least 40 different loci or genes, and more preferably at least 100, at least 500, at least 1000 or at least 5000 different loci or genes, such as 100 to 10,000 different loci or genes. The lengths of the second set of nucleic acids are suitable for them to specifically hybridise according to Watson Crick base pairing to the first set of nucleic acids to allow identification of chromosome interactions specific to subgroups. Typically the second set of nucleic acids will comprise two portions corresponding in sequence to the two chromosome regions which come together in the chromosome interaction. The second set of nucleic acids typically comprise nucleic acid sequences which are at least 10, preferably 20, and preferably still 30 bases (nucleotides) in length. In another embodiment, the nucleic acid sequences may be at the most 500, preferably at most 100, and preferably still at most 50 base pairs in length. In a preferred embodiment, the second set of nucleic acids comprises nucleic acid sequences of between 17 and 25 base pairs. In one embodiment at least 100, 80% or 50% of the second set of nucleic acid sequences have lengths as described above. Preferably the different nucleic acids do not have any overlapping sequences, for example at least 100%, 90%, 80% or 50% of the nucleic acids do not have the same sequence over at least 5 contiguous nucleotides.

Given that the second set of nucleic acids acts as an 'index' then the same set of second nucleic acids may be used with different sets of first nucleic acids which represent subgroups for different characteristics, i.e. the second set of nucleic acids may represent a 'universal' collection of nucleic acids which can be used to identify chromosome interactions relevant to different characteristics.

The First Set of Nucleic Acids

The first set of nucleic acids are typically from subgroups relevant to diagnosis or prognosis of ALS or Huntington's disease. The first nucleic acids may have any of the characteristics and properties of the second set of nucleic acids mentioned herein. The first set of nucleic acids is normally derived from a sample from the individuals which has undergone treatment and processing as described herein, particularly the EpiSwitch™ cross-linking and cleaving steps. Typically the first set of nucleic acids represents all or at least 80% or 50% of the chromosome interactions present in the samples taken from the individuals.

Typically, the first set of nucleic acids represents a smaller population of chromosome interactions across the loci or genes represented by the second set of nucleic acids in comparison to the chromosome interactions represented by second set of nucleic acids, i.e. the second set of nucleic acids is representing a background or index set of interactions in a defined set of loci or genes.

Library of Nucleic Acids

Any of the types of nucleic acid populations mentioned herein may be present in the form of a library comprising at least 200, at least 500, at least 1000, at least 5000 or at least 10000 different nucleic acids of that type, such as 'first' or 'second' nucleic acids. Such a library may be in the form of being bound to an array.

Hybridisation

The invention requires a means for allowing wholly or partially complementary nucleic acid sequences from the first set of nucleic acids and the second set of nucleic acids to hybridise. In one embodiment all of the first set of nucleic acids is contacted with all of the second set of nucleic acids in a single assay, i.e. in a single hybridisation step. However any suitable assay can be used.

Labelled Nucleic Acids and Pattern of Hybridisation

The nucleic acids mentioned herein may be labelled, preferably using an independent label such as a fluorophore (fluorescent molecule) or radioactive label which assists detection of successful hybridisation. Certain labels can be detected under UV light. The pattern of hybridisation, for example on an array described herein, represents differences in epigenetic chromosome interactions between the two subgroups, and thus provides a process of comparing epigenetic chromosome interactions and determination of which epigenetic chromosome interactions are specific to a subgroup in the population of the present invention.

The term 'pattern of hybridisation' broadly covers the presence and absence of hybridisation between the first and second set of nucleic acids, i.e. which specific nucleic acids from the first set hybridise to which specific nucleic acids from the second set, and so it not limited to any particular assay or technique, or the need to have a surface or array on which a 'pattern' can be detected.

Selecting a Subgroup with Particular Characteristics

The invention provides a process which comprises detecting the presence or absence of chromosome interactions, typically 5 to 20 or 5 to 500 such interactions, preferably 20 to 300 or 50 to 100 interactions, in order to determine the presence or absence of a characteristic relating to ALS or Huntington's disease in an individual. Preferably the chromosome interactions are those in any of the genes mentioned herein. In one embodiment the chromosome interactions which are typed are those represented by the nucleic acids in Table 1 or 5. Preferably the chromosome interactions which are typed are those represented by the nucleic acids in Table 10, 11 or 12. The column titled 'Loop Detected' in the tables shows which subgroup is detected (ALS or control) by each probe. As can be seen the process of the invention can detect either an ALS subgroup and/or a control subgroup (non-ALS) as part of the testing.

The Individual that is Tested

Examples of the species that the individual who is tested is from are mentioned herein. In addition the individual that is tested in the process of the invention may have been selected in some way. The individual may be susceptible to ALS or Huntington's disease, for example.

Preferred Gene Regions, Loci, Genes and Chromosome Interactions

For all aspects of the invention preferred gene regions, loci, genes and chromosome interactions are mentioned in the tables, for example in Table 1 and 5. Typically in the processes of the invention chromosome interactions are detected from at least 1, 2, 3, 4, 5, 6, 7 or 8 of the relevant genes listed in Table 1 or 5. Preferably the presence or absence of at least 1, 2, 3, 4, 5, 6, 7 or 8 of the relevant specific chromosome interactions represented by the probe sequences in Table 1 or 5 are detected. The chromosome interaction may be upstream or downstream of any of the genes mentioned herein, for example 50 kb upstream or 20 kb downstream, for example from the coding sequence.

Preferably at least 5, 8, 10, 15 or all of the chromosome interactions in Table 1 are typed.

Typically embodiment at least 5, 7, 8 or all of the chromosome interactions in Table 5 are typed.

Preferably at least 4, 6 or all of the chromosome interactions in Table 10 are typed.

Typically at least 1, 2 or all of the chromosome interactions in Table 11 are typed.

Preferably at least 4, 6 or all of the chromosome interactions in Table 12 are typed.

Chromosome interactions may be typed to determine presence of disease. Chromosome interactions may be typed to determine whether the individual will progress fast or slow.

The specific probes and primer sequence disclosed in the tables (or derivates including fragments and homologues) may be used for any typing method disclosed herein. Their use in a method of diagnosis or prognosis is provided.

In one embodiment the locus (including the gene and/or place where the chromosome interaction is detected) may comprise a CTCF binding site. This is any sequence capable of binding transcription repressor CTCF. That sequence may consist of or comprise the sequence CCCTC which may be present in 1, 2 or 3 copies at the locus. The CTCF binding site sequence may comprise the sequence CCGCGNGG-NGGCAG (SEQ ID NO: 1) (in IUPAC notation). The CTCF binding site may be within at least 100, 500, 1000 or 4000 bases of the chromosome interaction or within any of the chromosome regions shown Table 1 or 5.

In one embodiment the chromosome interactions which are detected are present at any of the gene regions shown Table 1 or 5. In the case where a ligated nucleic acid is detected in the process then sequence shown in any of the probe sequences in Table 1 or 5 may be detected.

Thus typically sequence from both regions of the probe (i.e. from both sites of the chromosome interaction) could be detected. In preferred embodiments probes are used in the process which comprise or consist of the same or complementary sequence to a probe shown in any table. In some embodiments probes are used which comprise sequence which is homologous to any of the probe sequences shown in the tables.

Tables Provided Herein

Tables 1 and 5 show probe (Episwitch™ marker) data and gene data representing chromosome interactions relevant to ALS. The probe sequences show sequence which can be used to detect a ligated product generated from both sites of gene regions that have come together in chromosome interactions, i.e. the probe will comprise sequence which is complementary to sequence in the ligated product. The first two sets of Start-End positions show probe positions, and the second two sets of Start-End positions show the relevant 4 kb region. The following information is provided in the probe data table:

HyperG_Stats: p-value for the probability of finding that number of significant EpiSwitch™ markers in the locus based on the parameters of hypergeometric enrichment Probe Count Total: Total number of EpiSwitch™ Conformations tested at the locus Probe Count Sig: Number of EpiSwitch™ Conformations found to be statistical significant at the locus FDR HyperG: Multi-test (False Discovery Rate) corrected hypergeometric p-value Percent Sig: Percentage of significant EpiSwitch™ markers relative the number of markers tested at the locus log FC: logarithm base 2 of Epigenetic Ratio (FC)

AveExpr: average log 2-expression for the probe over all arrays and channels

T: moderated t-statistic p-value: raw p-value adj. p-value: adjusted p-value or q-value B—B-statistic (lods or B) is the log-odds that that gene is differentially expressed.

FC—non-log Fold Change

FC_1—non-log Fold Change centred around zero

LS— Binary value this relates to FC_1 values. FC_1 value below −1.1 it is set to −1 and if the FC_1 value is above 1.1 it is set to 1. Between those values the value is 0

Tables 1 and 5 show genes where a relevant chromosome interaction has been found to occur. Other tables show similar data. The p-value in the loci table is the same as the HyperG_Stats (p-value for the probability of finding that number of significant EpiSwitch™ markers in the locus based on the parameters of hypergeometric enrichment).

The probes are designed to be 30 bp away from the TaqI site. In case of PCR, PCR primers are also designed to detect ligated product but their locations from the TaqI site vary.

Probe Locations:
Start 1—30 bases upstream of TaqI site on fragment 1
End 1—TaqI restriction site on fragment 1
Start 2—TaqI restriction site on fragment 2
End 2—30 bases downstream of TaqI site on fragment 2

4 kb Sequence Location:
Start 1—4000 bases upstream of TaqI site on fragment 1
End 1—TaqI restriction site on fragment 1
Start 2—TaqI restriction site on fragment 2
End 2—4000 bases downstream of TaqI site on fragment 2

GLMNET values related to procedures for fitting the entire lasso or elastic-net regularization (Lambda set to 0.5 (elastic-net)).

Tables 1 to 4 relate to diagnosis of ALS, whilst Tables 5 to 9 relate to prognosis of ALS, and in one embodiment detection relevant to diagnosis is performed based on Tables 1 and 4 and detection relevant to prognosis is performed based on Tables 5 to 9.

Table 1—The LS column shows a 1 or −1.1 means present in ALS cases and −1 means absent from ALS cases.

Table 5—The LS column shows 1 or −1.1 means the marker is present in fast progressors and absent from slow progressors, and −1 means the marker is present in slow progressors but absent in fast progressors.

Tables 10 and 11 relate to ALS prognosis. Table 10 includes markers shown in earlier tables. The 'Loop detected' column of Table 11 means the marker is present in fast progressors and absent from slow progressors.

Markers are uniquely identified in the tables with reference to a relevant probe for the product of an EpiSwitch™ 3C method. In the case of hydrolysis probes these are located on top of Taq site (TCGA) and they cover both genome sites in EpiSwitch™ interaction. It measures the same junction as 60 base array probes (30 bases on each side of the sequence tags), but spans over a tailored length of the sequence on both sides. Table 19 provides an example of this.

Preferred Embodiments for Sample Preparation and Chromosome Interaction Detection Methods of preparing samples and detecting chromosome conformations are described herein. Optimised (non-conventional) versions of these methods can be used, for example as described in this section.

Typically the sample will contain at least $2\times10^5$ cells. The sample may contain up to $5\times10^5$ cells. In one embodiment, the sample will contain $2\times10^5$ to $5.5\times10^5$ cells Crosslinking of epigenetic chromosomal interactions present at the chromosomal locus is described herein. This may be performed before cell lysis takes place. Cell lysis may be performed for 3 to 7 minutes, such as 4 to 6 or about 5 minutes. In some embodiments, cell lysis is performed for at least 5 minutes and for less than 10 minutes.

Digesting DNA with a restriction enzyme is described herein. Typically, DNA restriction is performed at about 55° C. to about 70° C., such as for about 65° C., for a period of about 10 to 30 minutes, such as about minutes.

Preferably a frequent cutter restriction enzyme is used which results in fragments of ligated DNA with an average fragment size up to 4000 base pair. Optionally the restriction enzyme results in fragments of ligated DNA have an average fragment size of about 200 to 300 base pairs, such as about 256 base pairs. In one embodiment, the typical fragment size is from 200 base pairs to 4,000 base pairs, such as 400 to 2,000 or 500 to 1,000 base pairs.

In one embodiment of the EpiSwitch™ method a DNA precipitation step is not performed between the DNA restriction digest step and the DNA ligation step.

DNA ligation is described herein. Typically the DNA ligation is performed for 5 to 30 minutes, such as about 10 minutes.

The protein in the sample may be digested enzymatically, for example using a proteinase, optionally Proteinase K. The protein may be enzymatically digested for a period of about 30 minutes to 1 hour, for example for about 45 minutes. In one embodiment after digestion of the protein, for example Proteinase K digestion, there is no cross-link reversal or phenol DNA extraction step.

In one embodiment PCR detection is capable of detecting a single copy of the ligated nucleic acid, preferably with a binary read-out for presence/absence of the ligated nucleic acid.

Processes and Uses of the Invention

The process of the invention can be described in different ways. It can be described as a method of making a ligated nucleic acid comprising (i) in vitro cross-linking of chromosome regions which have come together in a chromosome interaction; (ii) subjecting said cross-linked DNA to cutting or restriction digestion cleavage; and (iii) ligating said cross-linked cleaved DNA ends to form a ligated nucleic acid, wherein detection of the ligated nucleic acid may be used to determine the chromosome state at a locus, and wherein preferably:

- the locus may be any of the loci, regions or genes mentioned in Table 1 or 5,
- and/or wherein the chromosomal interaction may be any of the chromosome interactions mentioned herein or corresponding to any of the probes disclosed in Table 1 or 5, and/or
- wherein the ligated product may have or comprise (i) sequence which is the same as or homologous to any of the probe sequences disclosed in Table 1 or 5; or (ii) sequence which is complementary to (ii).

The process of the invention can be described as a process for detecting chromosome states which represent different subgroups in a population comprising determining whether a chromosome interaction is present or absent within a defined epigenetically active (disease associated) region of the genome, wherein preferably:

- the subgroup is defined by presence or absence of ALS or a characteristic relating to ALS (such as prognosis or progression), and/or
- the chromosome state may be at any locus, region or gene mentioned in Table 1 or 5; and/or
- the chromosome interaction may be any of those mentioned in Table 1 or 5 or corresponding to any of the probes disclosed in that table.

The invention includes detecting chromosome interactions at any locus, gene or regions mentioned Table 1 or 5. The invention includes use of the nucleic acids and probes mentioned herein to detect chromosome interactions, for example use of at least 1, 2, 4, 6 or 8 such nucleic acids or probes to detect chromosome interactions in at least 1, 2, 4, 6 or 8 different loci or genes. The invention includes detection of chromosome interactions using any of the primers or primer pairs listed in Table 2 or 7 or using variants of these primers as described herein (sequences comprising the primer sequences or comprising fragments and/or homologues of the primer sequences).

When analysing whether a chromosome interaction occurs 'within' a defined gene, region or location, either both the parts of the chromosome which have together in the interaction are within the defined gene, region or location or in some embodiments only one part of the chromosome is within the defined, gene, region or location.

Use of the Method of the Invention to Identify New Treatments

Knowledge of chromosome interactions can be used to identify new treatments for conditions. The invention provides methods and uses of chromosomes interactions defined here to identify or design new therapeutic agents for ALS (including treatments relating to prognosis).

Homologues

Homologues of polynucleotide/nucleic acid (e.g. DNA) sequences are referred to herein. Such homologues typically have at least 70% homology, preferably at least 80%, at least 85%, at least 90%, at least 95%, at least 97%, at least 98% or at least 99% homology, for example over a region of at least 10, 15, 20, 30, 100 or more contiguous nucleotides, or across the portion of the nucleic acid which is from the region of the chromosome involved in the chromosome interaction. The homology may be calculated on the basis of nucleotide identity (sometimes referred to as "hard homology").

Therefore, in a particular embodiment, homologues of polynucleotide/nucleic acid (e.g. DNA) sequences are referred to herein by reference to percentage sequence identity. Typically such homologues have at least 70% sequence identity, preferably at least 80%, at least 85%, at least 90%, at least 95%, at least 97%, at least 98% or at least 99% sequence identity, for example over a region of at least 10, 15, 20, 30, 100 or more contiguous nucleotides, or across the portion of the nucleic acid which is from the region of the chromosome involved in the chromosome interaction.

For example the UWGCG™ Package provides the BESTFIT™ program which can be used to calculate homology and/or % sequence identity (for example used on its default settings) (Devereux et al (1984) Nucleic Acids Research 12, p 387-395). The PILEUP' and BLAST' algorithms can be used to calculate homology and/or % sequence identity and/or line up sequences (such as identifying equivalent or corresponding sequences (typically on their default settings)), for example as described in Altschul S. F. (1993) J Mol Evol 36:290-300; Altschul, S, F et al (1990) J Mol Biol 215:403-10.

Software for performing BLAST' analyses is publicly available through the National Center for Biotechnology Information. This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST™ algorithm parameters W5 T and X determine the sensitivity and speed of the alignment. The BLAST™ program uses as defaults a word length (W) of 11, the BLOSUM62 scoring matrix (see Henikoff and Henikoff (1992) Proc. Natl. Acad. Sci. USA 89: 10915-10919) alignments (B) of 50, expectation (E) of 10, M=5, N=4, and a comparison of both strands.

The BLAST™ algorithm performs a statistical analysis of the similarity between two sequences; see e.g., Karlin and Altschul (1993) Proc. Natl. Acad. Sci. USA 90: 5873-5787. One measure of similarity provided by the BLAST™ algorithm is the smallest sum probability (P(N)), which provides an indication of the probability by which a match between two polynucleotide sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

The homologous sequence typically differs by 1, 2, 3, 4 or more bases, such as less than 10, 15 or 20 bases (which may be substitutions, deletions or insertions of nucleotides). These changes may be measured across any of the regions mentioned above in relation to calculating homology and/or % sequence identity.

Homology of a 'pair of primers' can be calculated, for example, by considering the two sequences as a single sequence (as if the two sequences are joined together) for the purpose of then comparing against the another primer pair which again is considered as a single sequence.

Arrays

The second set of nucleic acids may be bound to an array, and in one embodiment there are at least 15,000, 45,000, 100,000 or 250,000 different second nucleic acids bound to the array, which preferably represent at least 300, 900, 2000 or 5000 loci. In one embodiment one, or more, or all of the different populations of second nucleic acids are bound to more than one distinct region of the array, in effect repeated on the array allowing for error detection. The array may be based on an Agilent™ SurePrint™ G3 Custom CGH microarray platform. Detection of binding of first nucleic acids to the array may be performed by a dual colour system.

Therapeutic Agents

Therapeutic agents are mentioned herein. The invention provides such agents for use in preventing or treating ALS in certain individuals, for example those identified by a process of the invention. This may comprise administering to an individual in need a therapeutically effective amount of the agent. The invention provides use of the agent in the manufacture of a medicament to prevent or treat ALS in certain individuals.

Preferred therapeutic agents for ALS are:
Riluzole™ (Rilutek™): This drug is typically taken as a pill and it reduces the disease's progression by reducing levels of a messenger (glutamate) in the brain. Glutamate is present in higher levels in ALS patient.
Edaravone™ (Radicava™): This drug reduces the decline in daily performance related to ALS. The drug is typically given to patient via intravenous infusion for 10-14 days in a row, once a month.
Arimoclomol™: This drug performs as a heat shock response inducer in motor neurons and it defends against neuronal disorder and cell death.
Talampanel™: This drug reduces the rate of muscle strength decline and symptoms progression.
Beta-lactam antibiotics: These antibodies such as penicillin and cephalosporin maintain muscle stability and increase life time via up-regulating the level of GLT1, glial glutamate transporter 1.
Bromocriptine™: This drug is a free-radical scavenger that inhibits oxidative cell death induced by stress.
Pramipexole™ and Dexpramipexole™: These drugs act as a dopamine agonist and they have a free-radical scavenging function. These drugs are involved in mitochondrial malfunction. Dexpramipexole™ is an optical enantiomer of Pramipexole™.
Stem Cell therapy: Stem cell growth reduces the progression of neuron disease or replaces motor neurons. Stem cells have the potential to make spinal motor neurons, expand axons and receive and generate synapses with the muscle. Mesenchymal stem cells (MSCs) derived from adult stem cells releases trophic factors, anti-inflammatory cytokines and immunomodulatory chemokines to postpone disease progression.
Immunotherapy: Antibody therapy, such as D3H5 antibody infusion via ICV route maintains weight for a longer period of time and prolongs the life time of transgenic mouse model for ALS.

The following is a list of therapies for Huntington's disease. These can help reduce some symptoms of movement and psychiatric disorders.
Medications for movement disorders
Tetrabenazine™ (Xenazine™)
Antipsychotic drugs, such as Haloperidol™ (Haldol™), Chlorpromazine™, Risperidone™ (Risperdal™) and quetiapine (Seroquel™)
Other medications include amantadine, levetiracetam (Keppra™, others) and clonazepam (Klonopin™)
Medications for Psychiatric Disorders
Antidepressants include citalopram (Celexa™), escitalopram (Lexapro™), fluoxetine (Prozac™, Sarafem™) and sertraline (Zoloft™)
Antipsychotics include quetiapine (Seroquel™), Risperidone™ (Risperdal™) and olanzapine (Zyprexa™)
Mood-stabilizing drugs include valproate (Depacon™), carbamazepine (Carbatrol™, Epitol™, Tegretol™) and lamotrigine (Lamictal™)

Early diagnosis of Huntington's helps to manage the treatment of symptoms over the course of the disease.

The formulation of the agent (for ALS or Huntington's disease) will depend upon the nature of the agent. The agent will be provided in the form of a pharmaceutical composition containing the agent and a pharmaceutically acceptable carrier or diluent. Suitable carriers and diluents include isotonic saline solutions, for example phosphate-buffered saline. Typical oral dosage compositions include tablets, capsules, liquid solutions and liquid suspensions. The agent may be formulated for parenteral, intravenous, intramuscular, subcutaneous, transdermal or oral administration.

The dose of an agent may be determined according to various parameters, especially according to the substance used; the age, weight and condition of the individual to be treated; the route of administration; and the required regimen. A physician will be able to determine the required route of administration and dosage for any particular agent. A suitable dose may however be from 0.1 to 100 mg/kg body weight such as 1 to 40 mg/kg body weight, for example, to be taken from 1 to 3 times daily.

Forms of the Substance Mentioned Herein

Any of the substances, such as nucleic acids or therapeutic agents, mentioned herein may be in purified or isolated form. They may be in a form which is different from that found in nature, for example they may be present in combination with other substance with which they do not occur in nature. The nucleic acids (including portions of sequences defined herein) may have sequences which are different to those found in nature, for example having at least 1, 2, 3, 4 or more nucleotide changes in the sequence as described in the section on homology. The nucleic acids may have heterologous sequence at the 5' or 3' end. The nucleic acids may be chemically different from those found in nature, for example they may be modified in some way, but preferably are still capable of Watson-Crick base pairing. Where appropriate the nucleic acids will be provided in double stranded or single stranded form. The invention provides all of the specific nucleic acid sequences mentioned herein in single or double stranded form, and thus includes the complementary strand to any sequence which is disclosed.

The invention also provides a kit for carrying out any process of the invention, including detection of a chromosomal interaction associated with ALS (relating for example to diagnosis or prognosis of ALS). Such a kit can include a specific binding agent capable of detecting the relevant chromosomal interaction, such as agents capable of detecting a ligated nucleic acid generated by processes of the invention. Preferred agents present in the kit include probes capable of hybridising to the ligated nucleic acid or primer pairs, for example as described herein, capable of amplifying the ligated nucleic acid in a PCR reaction.

The invention also provides a device that is capable of detecting the relevant chromosome interactions. The device preferably comprises any specific binding agents, probe or primer pair capable of detecting the chromosome interaction, such as any such agent, probe or primer pair described herein.

Detection Methods

In one embodiment quantitative detection of the ligated sequence which is relevant to a chromosome interaction is carried out using a probe which is detectable upon activation during a PCR reaction, wherein said ligated sequence comprises sequences from two chromosome regions that come together in an epigenetic chromosome interaction, wherein said method comprises contacting the ligated sequence with the probe during a PCR reaction, and detecting the extent of activation of the probe, and wherein said probe binds the ligation site. The method typically allows particular interactions to be detected in a MIQE compliant manner using a dual labelled fluorescent hydrolysis probe.

The probe is generally labelled with a detectable label which has an inactive and active state, so that it is only detected when activated. The extent of activation will be related to the extent of template (ligation product) present in the PCR reaction. Detection may be carried out during all or some of the PCR, for example for at least 50% or 80% of the cycles of the PCR.

The probe can comprise a fluorophore covalently attached to one end of the oligonucleotide, and a quencher attached to the other end of the nucleotide, so that the fluorescence of the fluorophore is quenched by the quencher. In one embodiment the fluorophore is attached to the 5'end of the oligonucleotide, and the quencher is covalently attached to the 3' end of the oligonucleotide. Fluorophores that can be used in the methods of the invention include FAM™, TET™, JOE™, Yakima Yellow™, HEX™, Cyanine3™, ATTO 550™, TAMRA™, ROX™, Texas Red™, Cyanine 3.5™, LC610™, LC 640™, ATTO 647N™, Cyanine 5™, Cyanine 5.5™ and ATTO 680™. Quenchers that can be used with the appropriate fluorophore include TAM™, BHQ1™, DAB™, Eclip™, BHQ2™ and BBQ650™, optionally wherein said fluorophore is selected from HEX™, Texas Red™ and FAM™. Preferred combinations of fluorophore and quencher include FAM™ with BHQ1™ and Texas Red™ with BHQ2™.

Use of the Probe in a qPCR Assay

Hydrolysis probes of the invention are typically temperature gradient optimised with concentration matched negative controls. Preferably single-step PCR reactions are optimized. More preferably a standard curve is calculated. An advantage of using a specific probe that binds across the junction of the ligated sequence is that specificity for the ligated sequence can be achieved without using a nested PCR approach. The methods described herein allow accurate and precise quantification of low copy number targets. The target ligated sequence can be purified, for example gel-purified, prior to temperature gradient optimization. The target ligated sequence can be sequenced. Preferably PCR reactions are performed using about 10 ng, or 5 to 15 ng, or 10 to 20 ng, or 10 to 50 ng, or 10 to 200 ng template DNA. Forward and reverse primers are designed such that one primer binds to the sequence of one of the chromosome regions represented in the ligated DNA sequence, and the other primer binds to other chromosome region represented in the ligated DNA sequence, for example, by being complementary to the sequence.

Choice of Ligated DNA Target

The invention includes selecting primers and a probe for use in a PCR method as defined herein comprising selecting primers based on their ability to bind and amplify the ligated sequence and selecting the probe sequence based properties of the target sequence to which it will bind, in particular the curvature of the target sequence.

Probes are typically designed/chosen to bind to ligated sequences which are juxtaposed restriction fragments spanning the restriction site. In one embodiment of the invention, the predicted curvature of possible ligated sequences relevant to a particular chromosome interaction is calculated, for example using a specific algorithm referenced herein. The curvature can be expressed as degrees per helical turn, e.g. 10.5° per helical turn. Ligated sequences are selected for targeting where the ligated sequence has a curvature propensity peak score of at least 5° per helical turn, typically at least 10°, 15° or 20° per helical turn, for example 5° to 20° per helical turn. Preferably the curvature propensity score per helical turn is calculated for at least 20, 50, 100, 200 or 400 bases, such as for 20 to 400 bases upstream and/or downstream of the ligation site. Thus in one embodiment the target sequence in the ligated product has any of these levels of curvature. Target sequences can also be chosen based on lowest thermodynamic structure free energy.

Preferred ALS Embodiments

Paragraph 1. A process for detecting a chromosome state which represents a disease subgroup in a population comprising determining whether a chromosome interaction relating to that chromosome state is present or absent within a defined region of the genome, wherein said disease subgroup is an amyotrophic lateral sclerosis (ALS) subgroup; and wherein said chromosome interaction has optionally been identified by a method of determining which chromosomal interactions are relevant to a chromosome state corresponding to an ALS subgroup of the population, comprising contacting a first set of nucleic acids from subgroups with different states of the chromosome with a second set of index nucleic acids, and allowing complementary sequences to hybridise, wherein the nucleic acids in the first and second sets of nucleic acids represent a ligated product comprising sequences from both the chromosome regions that have come together in chromosomal interactions, and wherein the pattern of hybridisation between the first and second set of nucleic acids allows a determination of which chromosomal interactions are specific to an ALS subgroup; and wherein the chromosome interaction:

(i) is present in any one of the regions or genes listed in Table 1 or 5; and/or
(ii) corresponds to any one of the chromosome interactions represent by any probe shown in Table 1 or 5, and/or
(iii) is present in a 4,000 base region which comprises or which flanks (i) or (ii).

Paragraph 2. A process according to paragraph 1 which is carried out to diagnose ALS or to determine a prognosis for ALS.

Paragraph 3. A process according to paragraph 1 or 2 wherein a specific combination of chromosome interactions are typed:

(i) comprising all of the chromosome interactions represented by the probes in Table 1 or 5; or
(ii) comprising at least 4, 5, 6 or 7 of the chromosome interactions represented by the probes in Table 1 or 5; or
(iii) which together are present in at least 4, 5, 6 or 7 of the regions or genes listed in Table 1 or 5; or
(iv) at least 4, 5, 6 or 7 chromosome interactions are typed which are present in a 4,000 base region which comprises or which flanks the chromosome interactions represented by the probes in Table 1 or 5.

Paragraph 4. A process according to any one of the preceding paragraphs in which the chromosome interactions are typed:
in a sample from an individual, and/or
by detecting the presence or absence of a DNA loop at the site of the chromosome interactions, and/or
detecting the presence or absence of distal regions of a chromosome being brought together in a chromosome conformation, and/or
by detecting the presence of a ligated nucleic acid which is generated during said typing and whose sequence comprises two regions each corresponding to the regions of the chromosome which come together in the chromosome interaction, wherein detection of the ligated nucleic acid is preferably by using (i) a probe that has at least 70% identity to any of the specific probe sequences mentioned in Table 1 or 5, and/or (ii) by a primer pair which has at least 70% identity to any primer pair in Table 2 or 7.

Paragraph 5. A process according to any one of the preceding paragraphs, wherein:
the second set of nucleic acids is from a larger group of individuals than the first set of nucleic acids; and/or
the first set of nucleic acids is from at least 8 individuals; and/or
the first set of nucleic acids is from at least 4 individuals from a first subgroup and at least 4 individuals from a second subgroup which is preferably non-overlapping with the first subgroup; and/or
the process is carried out to select an individual for a medical treatment.

Paragraph 6. A process according to any one of the preceding paragraphs wherein:
the second set of nucleic acids represents an unselected group; and/or
wherein the second set of nucleic acids is bound to an array at defined locations; and/or
wherein the second set of nucleic acids represents chromosome interactions in least 100 different genes; and/or
wherein the second set of nucleic acids comprises at least 1,000 different nucleic acids representing at least 1,000 different chromosome interactions; and/or
wherein the first set of nucleic acids and the second set of nucleic acids comprise at least 100 nucleic acids with length 10 to 100 nucleotide bases.

Paragraph 7. A process according to any one of the preceding paragraphs, wherein the first set of nucleic acids is obtainable in a process comprising the steps of: —
(i) cross-linking of chromosome regions which have come together in a chromosome interaction;
(ii) subjecting said cross-linked regions to cleavage, optionally by restriction digestion cleavage with an enzyme; and
(iii) ligating said cross-linked cleaved DNA ends to form the first set of nucleic acids (in particular comprising ligated DNA).

Paragraph 8. A process according to any one of the preceding paragraphs wherein at least 5 to 9 different chromosome interactions are typed, preferably in 5 to 9 different regions or genes.

Paragraph 9. A process according to any one of the preceding paragraphs wherein said defined region of the genome:
(i) comprises a single nucleotide polymorphism (SNP); and/or
(ii) expresses a microRNA (miRNA); and/or
(iii) expresses a non-coding RNA (ncRNA); and/or
(iv) expresses a nucleic acid sequence encoding at least 10 contiguous amino acid residues; and/or
(v) expresses a regulating element; and/or
(vii) comprises a CTCF binding site.

Paragraph 10. Method for identifying or designing a therapeutic agent for treating ALS by selecting an agent that is able to cause a change of chromosomal interaction and thereby cause a therapeutic effect,
wherein the chromosomal interaction is represented by any probe in Table 1 or 5; and/or
the chromosomal interaction is present in any region or gene listed in Table 1 or 5;
and wherein optionally:
the chromosomal interaction has been identified by the method of determining which chromosomal interactions are relevant to a chromosome state as defined in paragraph 1, and/or
the change in chromosomal interaction is monitored using (i) a probe that has at least 70% identity to any of the probe sequences mentioned in Table 1 or 5, and/or (ii) by a primer pair which has at least 70% identity to any primer pair in Table 1 or 5; and/or
a candidate agent is contacted with a cell and the chromosome interaction in the cell is monitored to determine whether the candidate agent is able to treat ALS.

Paragraph 11. Use of
(i) detection of a chromosomal interaction wherein:
the chromosomal interaction is as represented by a probe in Table 1 or 5, and/or
the chromosomal interaction is present in any region or gene which is mentioned in Table 1 or 5; or
(ii) a probe that has at least 70% identity to any of the probe sequences mentioned in Table 1 or 5, or
(iii) a primer pair which has at least 70% identity to any primer pair identified in Table 2 or 7; to identify or design a therapeutic agent for ALS.

Paragraph 12. Use according to paragraph 11 to identify a therapeutic agent comprising administering a candidate agent, and using said detection of a chromosomal interaction, said probe or said primer pair to detect whether there is a change in chromosome state to thereby determine whether the candidate agent is a therapeutic agent, wherein the use is optionally performed in vitro, preferably in a cell.

Paragraph 13. A therapeutic agent for ALS for use in a method of preventing or treating ALS in an individual that has been identified as being in need of the therapeutic agent by a process according to any one of paragraphs 1 to 9.

Paragraph 14. A process, method or use according to any of the preceding paragraphs wherein the typing or detecting comprises specific detection of the ligated product by quantitative PCR (qPCR) which uses primers capable of amplifying the ligated product and a probe which binds the ligation site during the PCR reaction, wherein said probe comprises sequence which is complementary to sequence from each of the chromosome regions that have come together in the chromosome interaction, wherein preferably said probe comprises:
- an oligonucleotide which specifically binds to said ligated product, and/or
- a fluorophore covalently attached to the 5' end of the oligonucleotide, and/or
- a quencher covalently attached to the 3' end of the oligonucleotide, and optionally
- said fluorophore is selected from HEX™, Texas Red™ and FAM™; and/or
- said probe comprises a nucleic acid sequence of length 10 to 40 nucleotide bases, preferably a length of to 30 nucleotide bases.

Particular Embodiments

In one embodiment only intrachromosomal interactions are typed/detected, and no extrachromosomal interactions (between different chromosomes) are typed/detected.

Publications

The contents of all publications mentioned herein are incorporated by reference into the present specification and may be used to further define the features relevant to the invention.

Specific Embodiments

The EpiSwitch™ platform technology detects epigenetic regulatory signatures of regulatory changes between normal and abnormal conditions at loci. The EpiSwitch™ platform identifies and monitors the fundamental epigenetic level of gene regulation associated with regulatory high order structures of human chromosomes also known as chromosome conformation signatures. Chromosome signatures are a distinct primary step in a cascade of gene deregulation. They are high order biomarkers with a unique set of advantages against biomarker platforms that utilize late epigenetic and gene expression biomarkers, such as DNA methylation and RNA profiling.

EpiSwitch™ Array Assay

The custom EpiSwitch™ array-screening platforms come in 4 densities of, 15K, 45K, 100K, and 250K unique chromosome conformations, each chimeric fragment is repeated on the arrays 4 times, making the effective densities 60K, 180K, 400K and 1 Million respectively.

Custom Designed EpiSwitch™ Arrays

The 15K EpiSwitch™ array can screen the whole genome including around 300 loci interrogated with the EpiSwitch™ Biomarker discovery technology. The EpiSwitch™ array is built on the Agilent™ SurePrint™ G3 Custom CGH microarray platform; this technology offers 4 densities, 60K, 180K, 400K and 1 Million probes. The density per array is reduced to 15K, 45K, 100K and 250K as each EpiSwitch™ probe is presented as a quadruplicate, thus allowing for statistical evaluation of the reproducibility. The average number of potential EpiSwitch™ markers interrogated per genetic loci is 50; as such the numbers of loci that can be investigated are 300, 900, 2000, and 5000.

EpiSwitch™ Custom Array Pipeline

The EpiSwitch™ array is a dual colour system with one set of samples, after EpiSwitch™ library generation, labelled in Cy5 and the other of sample (controls) to be compared/analyzed labelled in Cy3. The arrays are scanned using the Agilent™ SureScan™ Scanner and the resultant features extracted using the Agilent™ Feature Extraction software. The data is then processed using the EpiSwitch™ array processing scripts in R. The arrays are processed using standard dual colour packages in Bioconductor in R: Limma *. The normalisation of the arrays is done using the normalisedWithinArrays function in Limma * and this is done to the on chip Agilent™ positive controls and EpiSwitch™ positive controls. The data is filtered based on the Agilent™ Flag calls, the Agilent control probes are removed and the technical replicate probes are averaged, in order for them to be analysed using Limma *. The probes are modelled based on their difference between the 2 scenarios being compared and then corrected by using False Discovery Rate. Probes with Coefficient of Variation (CV)<=30% that are <=-1.1 or =>1.1 and pass the p<=0.1 FDR p-value are used for further screening. To reduce the probe set further Multiple Factor Analysis is performed using the FactorMineR package in R.

* Note: LIM MA is Linear Models and Empirical Bayes Processes for Assessing Differential Expression in Microarray Experiments. Limma is an R package for the analysis of gene expression data arising from microarray or RNA-Seq.

The pool of probes is initially selected based on adjusted p-value, FC and CV<30% (arbitrary cut off point) parameters for final picking. Further analyses and the final list are drawn based only on the first two parameters (adj. p-value; FC).

The invention is illustrated by the following non-limiting examples.

Example 1

Statistical Pipeline

EpiSwitch™ screening arrays are processed using the EpiSwitch™ Analytical Package in R in order to select high value EpiSwitch™ markers for translation on to the EpiSwitch™ PCR platform.

Step 1

Probes are selected based on their corrected p-value (False Discovery Rate, FDR), which is the product of a modified linear regression model. Probes below p-value <=0.1 are selected and then further reduced by their Epigenetic ratio (ER), probes ER have to be <=-1.1 or =>1.1 in order to be selected for further analysis. The last filter is a coefficient of variation (CV), probes have to be below <=0.3.

Step 2

The top 40 markers from the statistical lists are selected based on their ER for selection as markers for PCR translation. The top 20 markers with the highest negative ER load and the top 20 markers with the highest positive ER load form the list.

Step 3

The resultant markers from step 1, the statistically significant probes form the bases of enrichment analysis using hypergeometric enrichment (HE). This analysis enables marker reduction from the significant probe list, and along with the markers from step 2 forms the list of probes translated on to the EpiSwitch™ PCR platform.

The statistical probes are processed by HE to determine which genetic locations have an enrichment of statistically significant probes, indicating which genetic locations are hubs of epigenetic difference.

The most significant enriched loci based on a corrected p-value are selected for probe list generation. Genetic locations below p-value of 0.3 or 0.2 are selected. The statistical probes mapping to these genetic locations, with the markers from step 2, form the high value markers for EpiSwitch™ PCR translation.

Array Design and Processing

Array Design

1. Genetic loci are processed using the SII software (currently v3.2) to:
   a. Pull out the sequence of the genome at these specific genetic loci (gene sequence with 50 kb upstream and 20 kb downstream)
   b. Define the probability that a sequence within this region is involved in CCs
   c. Cut the sequence using a specific RE
   d. Determine which restriction fragments are likely to interact in a certain orientation
   e. Rank the likelihood of different CCs interacting together.
2. Determine array size and therefore number of probe positions available (x)
3. Pull out x/4 interactions.
4. For each interaction define sequence of 30 bp to restriction site from part 1 and 30 bp to restriction site of part 2. Check those regions aren't repeats, if so exclude and take next interaction down on the list. Join both 30 bp to define probe.
5. Create list of x/4 probes plus defined control probes and replicate 4 times to create list to be created on array
6. Upload list of probes onto Agilent™ Sure design website for custom CGH array.
7. Use probe group to design Agilent™ custom CGH array.

Array Processing

1. Process samples using EpiSwitch™ Standard Operating Procedure (SOP) for template production.
2. Clean up with ethanol precipitation by array processing laboratory.
3. Process samples as per Agilent™ SureTag™ complete DNA labelling kit—Agilent™ Oligonucleotide Array-based CGH for Genomic DNA Analysis Enzymatic labelling for Blood, Cells or Tissues
4. Scan using Agilent™ C Scanner using Agilent™ feature extraction software.

EpiSwitch™ Technology Overview

The EpiSwitch™ platform offers a highly effective means of screening, early detection, companion-diagnosis, monitoring and prognostic analysis of major diseases associated with aberrant and responsive gene expression. The major advantages of this approach is that it is non-invasive, rapid, and relies on highly stable DNA based targets as part of chromosomal signatures, rather than unstable protein/RNA molecules.

EpiSwitch™ biomarker signatures demonstrate high robustness, sensitivity and specificity in the stratification of complex disease phenotypes. This technology takes advantage of the latest breakthroughs in the science of epigenetics, monitoring and evaluation of chromosome conformation signatures as a highly informative class of epigenetic biomarkers. Current research methodologies deployed in academic environment require from 3 to 7 days for biochemical processing of cellular material in order to detect CCSs. Those procedures have limited sensitivity, and reproducibility; and furthermore, do not have the benefit of the targeted insight provided by the EpiSwitch™ Analytical Package at the design stage.

EpiSwitch™ Array in Silico Marker Identification

CCS sites across the genome are directly evaluated by the EpiSwitch™ Array on clinical samples from testing cohorts for identification of all relevant stratifying lead biomarkers. The EpiSwitch™ Array platform is used for marker identification due to its high-throughput capacity, and its ability to screen large numbers of loci rapidly. The array used was the Agilent™ custom-CGH array, which allows markers identified through the in silico software to be interrogated.

EpiSwitch™ PCR

Potential markers identified by EpiSwitch™ Array are then validated either by EpiSwitch™ PCR or DNA sequencers (i.e. Roche 454™, Nanopore™ MinION™, etc.). The top PCR markers which are statistically significant and display the best reproducibility are selected for further reduction into the final EpiSwitch™ Signature Set, and validated on an independent cohort of samples. EpiSwitch™ PCR can be performed by a trained technician following a standardised operating procedure protocol established. All protocols and manufacture of reagents are performed under ISO 13485 and 9001 accreditation to ensure the quality of the work and the ability to transfer the protocols. EpiSwitch™ PCR and EpiSwitch™ Array biomarker platforms are compatible with analysis of both whole blood and cell lines. The tests are sensitive enough to detect abnormalities in very low copy numbers using small volumes of blood.

Analysis of an ALS Cohort

The inventors have used epigenetic chromosomal interactions as the basis for identifying biomarkers to be used as a companion diagnostic method in ALS. The EpiSwitch™ biomarker discovery platform was developed by the inventors to detect epigenetic regulatory signature changes such as those driving phenotypic changes implicated in ALS. The EpiSwitch™ biomarker discovery platform identifies CCSs which define the initial regulatory process in integrating environmental cues into the epigenetic and transcriptional machinery. As such, CCSs are the primary step in a cascade of gene regulation. The CCSs isolated by the EpiSwitch™ biomarker discovery platform have several well documented advantages: severe biochemical and physiological stability; their binary nature and readout; and their primary position in the eukaryotic cascade of gene regulation.

The ability to detect perturbations in the systemic epigenetic control of gene expression allows both early diagnosis of ALS and establishment of patient prognosis. A comparative interrogation of the cellular regulatory genome architecture from healthy and diseased-patient blood samples revealed two ALS-related epigenetic signatures: one with diagnostic potential and a second for prognosis prediction. For this prospective study, samples collected by the clinical-research group at the Oxford Motor Neuron Disorders Clinic at the Nuffield Department of Clinical Neurosciences (NDCN) at the University of Oxford were analyzed using EpiSwitch™, the high throughput platform developed by Oxford BioDynamics™ for monitoring chromosome conformation signatures. This study compares the clinical annotations of the ALS-FRS-R, Forced Vital Capacity (FVC) and other clinical observations to assign ALS-progression subtypes, with analysis for the epigenetic signatures.

A total of 100 patients, presenting to the Oxford Motor Neuron Disorders Clinic, enrolled in the study and were asked to return at 3 and 6 months. Controls (n=100) were collected. During each visit, participants underwent the ALS-FRS-R and FVC tests, and provided a blood sample. The samples were analyzed to identify either an ALS-disease-related diagnostic signature, or the prognostic disease-related signature (at 3 and 6 months). Results of the clinical assessments were compared to the EpiSwitch™ analysis at 0, 3 and 6 months. A cut off of a 0.5-point decline per month of the ALS-FRS-R score was used to cluster the ALS patients into progression-subtypes.

Based on the rate of decline in the ALS-FRS-R score, preliminary results from 3 month samples and 6-month samples demonstrated the epigenetic signature selected faster (>0.5) and slower (<0.5) progressing ALS patients with a sensitivity and specificity of 80%. To date, the results indicate the prognostic signature is robust for selecting subtypes of ALS across time. The results shown in the Tables relate to the diagnostic and prognostic analysis of 75 ALS and 75 control samples (n=150), with an independent sample cohort (n=50).

Further results (including Table 11) are based on 100 patients with ALS who have been observed and evaluated by standard practice of ALSFRS-R score and FVC (forced vital capacity) at baseline, 3 months and 6 months survival. Based on measurements at baseline and 3 months these patients were classified as slow or fast ALS (standard classification). With our three markers readout at the baseline only, we also classified all the patients as slow or fast (EpiSwitch™ classification). These patients were then evaluated on the basis of survival at 6 months, and survival for slow and fast groups was compared. Standard classification had significant number of fatal outcomes in the slow group and statistically the survival difference by p value between slow and fast was insignificant, p=0.052. By EpiSwitch™ classification, the separation between slow and fast at 6 months was highly significant, p=0.0097, and most of the deaths took place in the fast group.

Example 2

Genomic architecture differences at the HTT locus underlie symptomatic and pre-symptomatic cases of Huntington's Disease.

Huntington's disease (HD), a progressive neurodegenerative condition, is a genetic disorder that causes extensive degeneration of neurons in the adult brain, ultimately leading to death. The root cause of HD is an expanded trinucleotide cytosine-adenine-guanine (CAG) repeat in the "huntingtin gene" (HTT), which results in a mutant huntingtin protein with an increased tendency to form intracellular aggregates and cause neuronal death. Importantly, the number of CAG repeats correlate with disease onset and severity and patients with more than 39 CAG repeats will develop HD at some point in their life, the onset of disease can vary by decades within individuals and little is known about this presymptomatic phase. With the advancement of epigenetic approaches and emergence of new technologies for detection of epigenetic regulatory markers for DNA methylation, histone modifications, non-coding RNA and chromosome conformation signatures as part of understanding genome architecture, we were interested in analyzing the systemic regulatory changes in genomic architecture around the HTT gene and its relationship to disease manifestation. Here, we examined the detectable, systemic, non-invasive epigenetic differences at the HTT locus between presymptomatic and symptomatic HD patients compared to unaffected controls.

Methods: Using blood samples from patients with HD and healthy controls we used EpiSwitch™, a validated high-resolution industrial platform for the detection of chromosome conformations, to assess chromatin architecture in the immediate vicinity of the HTT gene. We evaluated the absence or presence of conditional, stable chromatin conformations at 20 interaction sites across over 225 kb of the HTT locus and compared the resulting chromosome conformations between groups of healthy controls, verified symptomatic HD patients (CAG, n>39) and patients with genetically verified CAG extension who had not manifested clinical symptoms of HD.

Results: Consistent and stable chromosome conformations were observed across the patient groups when tested in peripheral blood samples. We found two constitutive interactions (occurring in all patient groups and controls) and seven conditional interactions which were present in HD, but not in healthy controls. Most important, we observed three conditional interactions that were present only in HD patients manifesting clinical symptoms (symptomatic cases), but not in presymptomatic cases. 85% (6 out of 7) of the patients in the symptomatic HD cohort demonstrated at least one of the specific chromosome conformations associated with symptomatic HD.

Conclusion: Our results are the first evidence that the regulatory chromatin architecture at HTT locus is systemically altered in patients with HD. Moreover, the chromatin architecture at the HTT locus also shows conditional differences between clinical stages in symptomatic and presymptomatic HD patients. Given the high clinical utility in having a molecular tool to assess disease progression in HD, these results strongly suggest the non-invasive assessment of systemic chromosome conformation signatures (CCS) can be a valuable addition to prognostic assessment of HD patients.

Introduction

Huntington's Disease (HD) is a neurodegenerative condition characterized cellularly by the loss of neurons in the basal ganglia and clinically by uncontrolled movements, emotional problems, and loss of cognition. HD is an autosomal dominantly inherited disorder and although prevalence rates range widely depending on geography and ethnicity, it is thought to affect more than 50,000 people in the United States and Europe alone. The underlying genetic cause is a trinucleotide CAG expansion in the huntingtin gene (HTT), discovered as a genetic marker by James Gusella from Massachusetts General Hospital in 1983, which results in the production of a mutant huntingtin protein (mHTT) with a toxic poly-glutamine (polyQ) tract. However, despite decades of research and clinical trials, no successful therapy has yet been developed. The "typical" onset of HD is between the ages of 40-50, but up to 15% of cases have very late onset and don't show clinical symptoms until after the age of 60. In a recent meta-analysis of studies investigating cases of late-onset HD (LoHD), more than 90% of patients had CAG repeat lengths of 44. One of the more interesting observations in HD is that while there is a well-known correlation between the length of the polyQ repeat tract and the onset and severity of the disease, there is substantial variability within individual patients. For example, in patients with mid-range repeat lengths (defined here as between 40 and 50), disease onset can vary by 60 years in any individual patient. This means that many patients who are carriers of polyQ tracts that predispose to the development of the disease can live for decades in a "presymptomatic" state. What controls the onset of clinical symptoms remains currently unknown and complicates the prognostic evaluation of HD patients.

Although historically considered a monogenic disease, extensive research into the underlying pathology of HD suggests that the mechanisms leading to disease onset and progression are more complex than originally thought. Many different technologies have been used to look at the molecular changes underlying disease progression in HD including gene expression, proteomics, metabolomics, network analysis, genomics and single nucleotide polymorphism (SNP) profiling). As HD is considered a paradigm of a disease characterized by epigenetic dysregulation, more recently epigenetic approaches have emerged as a promising new tool for assessing pathology-related changes. Most epigenetic studies in HD have focused on looking at genome wide histone modifications (acetylation, methylation) or histone modifications at specific loci related to HD. While these approaches have provided interesting insight into the disease, they have yielded often conflicting results and shown inconsistencies between mouse models and human disease. As such, a consensus picture of epigenetic deregulation in HD using histone modification readouts has yet to materialize. However, not all molecular mechanisms associated with epigenetic regulation have been assessed in the context of HD. An important aspect of epigenetic regulation is at the level of 3-dimensional (3D) genomic architecture.

The 3D organization of the genome reflects the heterogeneous effects of external environmental cues and inputs and can be empirically measured by the assessment of chromosome conformations or when several conformations are measured concomitantly, a chromosome conformation signature (CCS). CCSs can be thought of as the molecular barcode that gives a readout of the epigenetic landscape of a given cellular population. Given the central role of mHTT in the development of HD, we hypothesized that regulatory differences in genomic architecture at the HTT locus may exist between diseased individuals and healthy, unaffected controls. We used EpiSwitch™, an established proprietary industrial platform for monitoring CCSs, to assess chromatin architecture differences between presymptomatic and symptomatic HD patients and healthy, unaffected individuals. EpiSwitch™ readouts provide high resolution, reliable and high throughput detection of CCSs while simultaneously meeting the high bar of industry standards for quality control.

Methods

Sample Collection

All samples were obtained from National BioService, LLC. In total, 20 samples were used in this study; 10 healthy control (HC) samples (CAG repeats, n<35), and 10 HD samples (CAG repeats, n>39). For the HD samples, 7 were from symptomatic patients (HD-Sym) and 3 were from presymptomatic patients who had a diagnosis of HD but did not yet show any clinical symptoms (HD-Pre). One HD patient was taking tetrabenazine and one patient was taking sertraline. All samples were negative for human immunodeficiency virus, hepatitis B virus, hepatitis C virus and syphilis (Table 14).

Study Design

Figure 2:
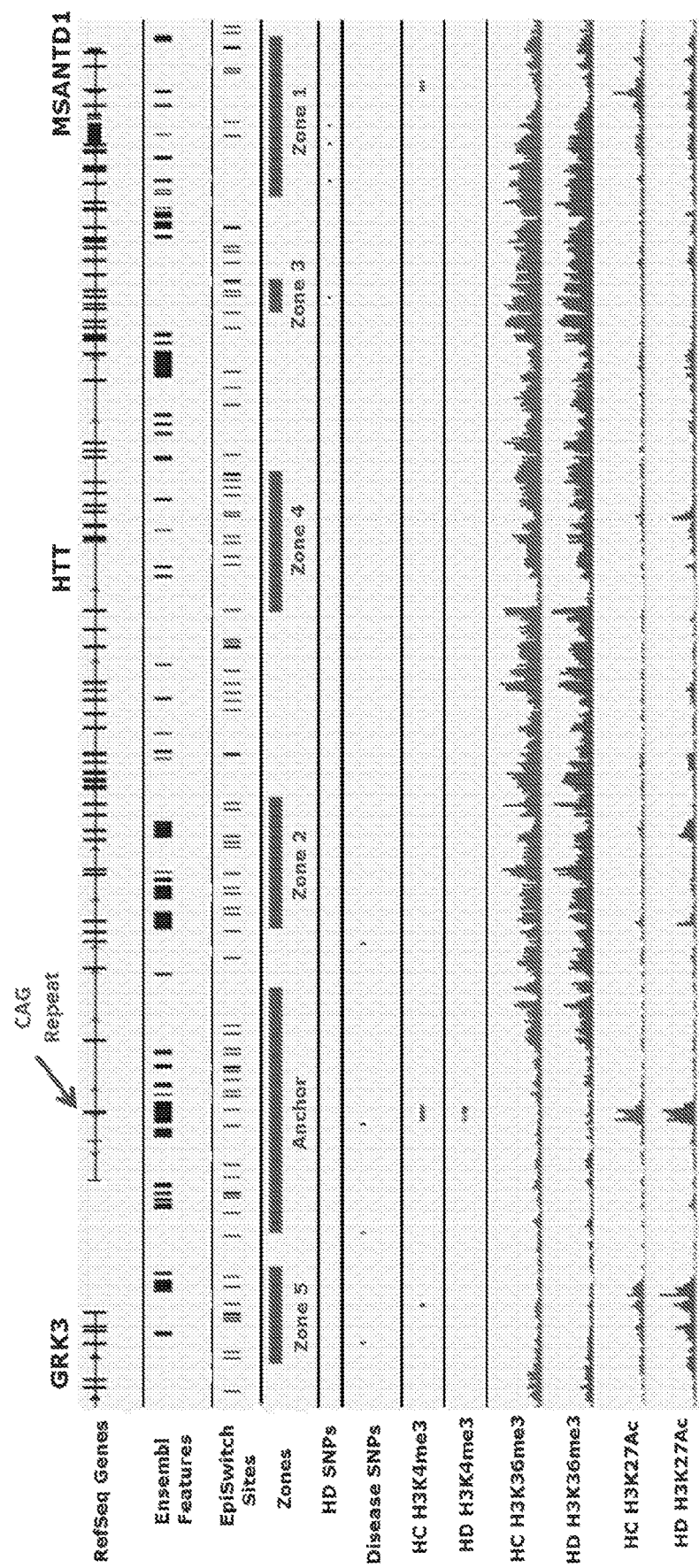
FIG. 2 shows a visual overview of the genomic region investigated in the Huntington's disease work. A ~225 kb region on chromosome 4 spanning the HTT locus was investigated. The Anchor point ("Anchor" in track 4) was defined as a ~42 kb region spanning the CAG repeat tract in exon 1 of HTT (purple arrow at the top of the figure). We defined five Zones (Zones 1-5 in track 4) based on overlap with EpiSwitch™ sites (track 3), SNPs related to HD (track 5) or other diseases (track 6), and observed methylation and acetylation (H3K4me3, H3K36me3 and H3K27Ac) differences between HC and HD (tracks 7 through 12).

We wanted to identify chromosome conformations that differed between healthy controls (low CAG), presymptomatic HD patients (high CAG, no disease manifestation) and symptomatic HD patients (high CAG, disease manifestation). We focused on a ~225 kb region surrounding the HTT locus from (chr4: 3,033,588 to 3,258,170 as annotated in hg38) for our analysis. Using the CAG repeat expansion tract in exon 1 of HTT (chr4: 3,054,162 to 3,095,930) as the anchor point ("Anchor"), we defined five genomic zones surrounding the Anchor to look at chromosome conformations that varied between sample groups (FIG. 2 and Table 15). These Zones were chosen based on: the presence of potential EpiSwitch™ anchoring sites; the presence of known disease related-SNPs (HD and other diseases); and the enrichment of known histone modification sites (H3K4me3, H3K36me3, and H3K27ac) in HD as found in the GWASdvV2 database (http://jjwanglab.org/gwasdb) (FIG. 2).

Chromosome Conformation Identity

A search of the NCBI: GEO database for previously reported HD epigenetic data was performed in February 2018. Peak called ChIP-seq data for H3K4me3 from 12 (6 HD and 6 control samples) post-mortem prefontal cortex brain samples (bed format) was obtained (GSE68952). In addition, Bigwig tracks of ChIP-seq data for H3K27 ac and H3K36me3 from HD iPSC-derived neural cell lines and control cell lines were also downloaded (GSE95342). The data tracks were loaded into the Integrative Genome Viewer (IGV) [41] alongside the EpiSwitch™ and reference sequence annotations. Both visual and programmatic (BEDtools™) comparisons were performed on the HTT locus to identify the 5 Zones of interest.

Appropriate software was used to identify high probability chromatin folding interactions with one "end" occurring in the Anchor zone proximal to the CAG repeats and the other in any of the 5 Zones of interest. A total of 61 interactions matched these criteria, and for practical reasons, 20 interactions were selected to cover interactions between the Anchor site and all the Zones of interest. An automated primer design application was used to design oligonucleotide pairs that amplified the expected DNA sequence caused by the interaction when subjected to the chromosome conformation capture assay.

3C and PCR

Chromosome conformation capture and detection by PCR were performed. Chromatin with intact chromosome conformations from 50 µl of blood sample from each patient sample was extracted using the EpiSwitch™ assay following the manufacturer's instructions (Oxford BioDynamics™ Plc). Quality control on all samples was done using the detection of a chromatin loop at the MM P1 locus, a historical internal control for 3C analysis. Pooled 3C libraries for each of the sample types were generated to provide a generalized population sample for each of the sample subgroups. Real-time PCR was performed with SYBR green with the CFX-96 (Bio-Rad) machine to identify the interactions with differing PCR product detection patterns between the sample types. Oligonucleotides were tested on control templates to confirm that each primer set was working correctly. In line with Royal Forensic Protocol for PCR detection the final nested PCR was performed on each sample in triplicates for the follow up data on individual HD patients. This procedure permitted the detection of limited copy-number templates with higher accuracy. All PCR amplified products were monitored on the LabChip®™ GX from Perkin Elmer™, using the LabChip™ DNA 1K Version2 kit (Perkin Elmer™) and internal DNA markers were loaded on the DNA chip according to the manufacturer's protocol using fluorescent dyes. Fluorescence was detected by laser and electropherogram read-outs translated into a simulated band on gel picture using the instrument software. The threshold of detection for the instrument was set by the manufacturer from 30 fluorescence units and above.

Statistical Analysis

Data analysis was performed in R (language and environment for statistical computing). This included stats and dplyr packages for t-tests and R-squared analysis & a ggplot2 package for boxplots and regression plots.

Results

Patient Clinical Characteristics

HC and HD samples were age (average 36.9 for HC and 35.3 for HD) and sex matched (½ male and ½ female), with the majority (70%) of HD cases being symptomatic (Table 16). All samples were from Non-Hispanic or Latino Whites. Average CAG repeats lengths were 25.7 for HC and 44.2 for HD (Table 16). The HC and HD samples showed no statistical difference in age. The HC patients showed no statistical difference in age from HD-Sym. HD-Pre patients were younger (average age=25.3) than HD-Sym patients (average age=39.6) (p=0.02). There was a moderate negative relationship between disease duration and CAG repeat size and a moderate positive relationship between age at diagnosis and CAG repeat size, though neither were statistically significant.

There was a statistically significant increase in CAG repeat length in HD patients relative to HC (p=1.08 $E^{-7}$). There was a statistically significant increase in CAG repeat length between HC and HD-Pre (p=3.43 $E^{-6}$) and HD-Sym (p=9.50 $E^{-8}$). There was no statistical difference in CAG repeat length between HD-Pre and HD-Sym (p=0.09).

The average age at diagnosis for HD samples was 35.3 and the average disease duration was 3.8 years with 7 out of 10 patients reporting symptoms of irritability, chorea, or both (Table 16).

Chromosome Conformations in HC, HD-Pre and HD-Sym

Of the 20 interactions that were evaluated (Table 17), we identified nine informative interactions. We identified two constitutive interactions and seven conditional interactions which were present in HD, but not healthy controls. Three of the seven conditional interactions were present only in HD-Sym, and absent in HD-Pre.

Constitutive Conformations

All samples passed internal QC analysis for the MMP1 interaction. Two constitutive (identified in all samples) chromatin loops were identified. Both loops were between the Anchor and Zone 2 with the first loop spanning 28 kb and the second loop spanning 34 kb. Two constitutive interactions occurring in all patients (HD-Sym, HD-Pre and HC) were observed in this study. Both interactions (CC1 & CC2) were between the Anchor and Zone 2 with CC1 spanning 28 kb and CC2 spanning 34 kb.

Conditional Conformations

Figure 3:
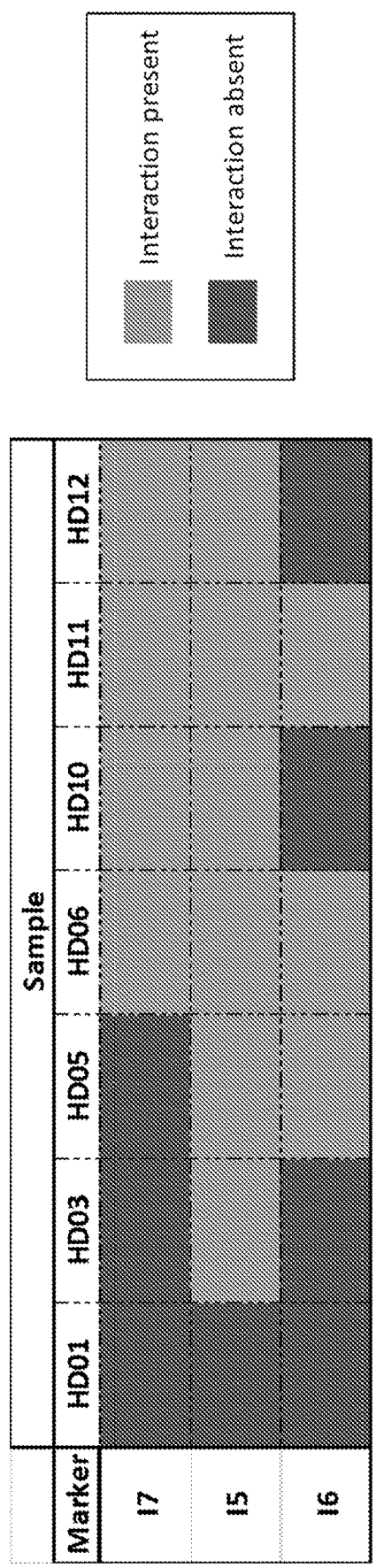
FIG. 3 shows that in six out of seven individual HD-Sym samples, the presence of at least one of the three conditional interactions (I5, I6 and I7) was observed. I5, the interaction spanning the region that contains the r5362331 SNP, was observed in the greatest number of samples (6/7).
Figure 4:
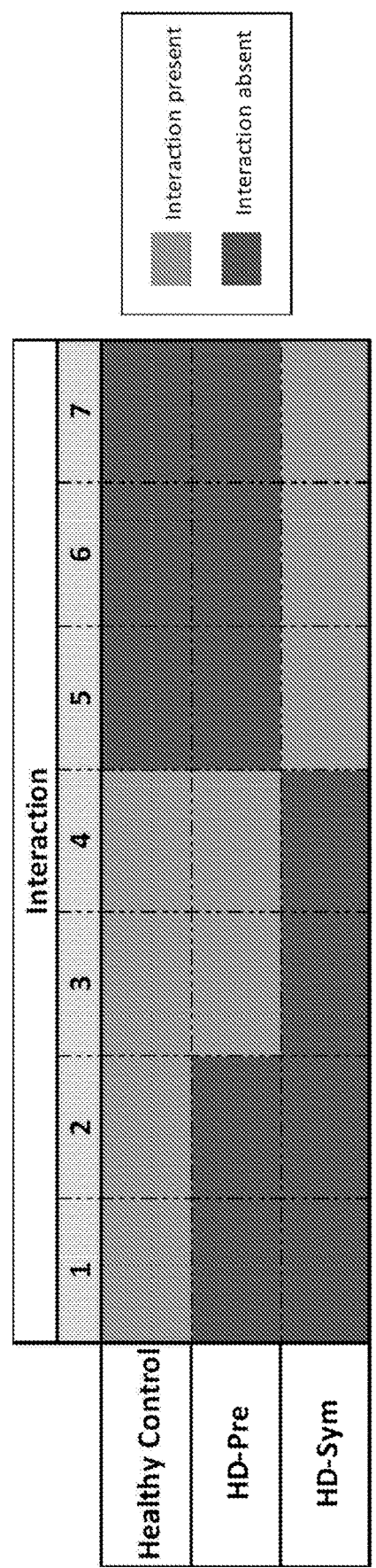
FIG. 4 provides a model for epigenetic changes driving the symptomatic progression of Huntington's disease. It shows an overview of the chromosomal conformation changes associated with the progression of HD. As patients progress from presymptomatic stages to symptomatic diseases, discrete, measurable and discriminating changes in the genomic architecture at the HTT locus are observed.
Figure 5:
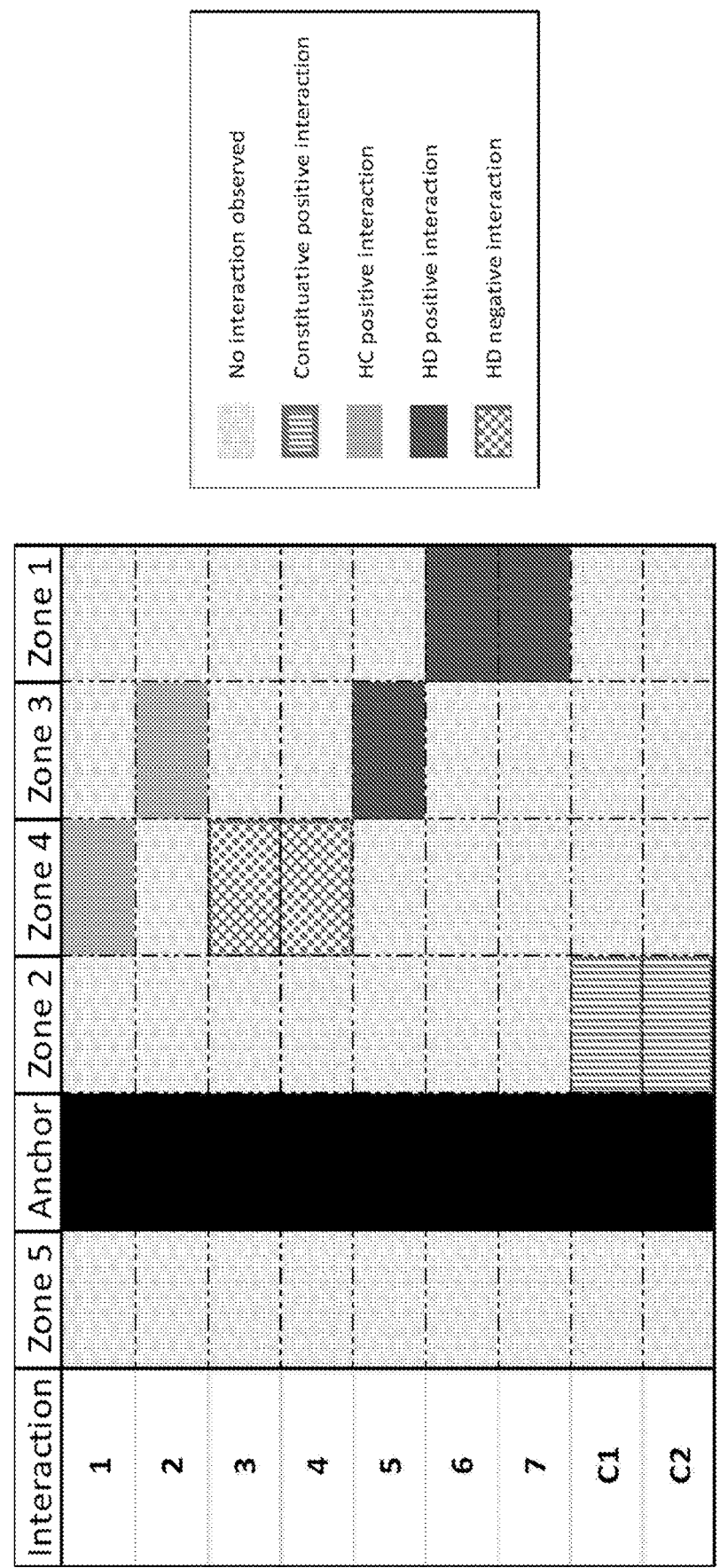
FIG. 5 shows a summary of all the Huntingon's disease interactions which were identified.

We identified seven conditional chromosome conformations that could discriminate between the different patient subgroups evaluated in this study. Specifically, we identified two chromosome interactions that were present in HC, but absent in all HD samples. The first interaction (11) spanned the Anchor and Zone 4 and covered 77 kb while the second interaction (12) spanned the Anchor and Zone 3 and covered 140 kb. We also identified two chromosome interactions that were present in HC and HD-Pre, but absent in HD-Sym samples. Both interactions (13 and 14) spanned the Anchor and Zone 4 and covered 92 kb and 104 kb, respectively. Last, we identified three chromosome interactions that were present in HD-Sym samples, but absent in HD-Pre and HC samples. The first interaction (15) spanned the Anchor and Zone 3, covering 122 kb. Interestingly, this interaction included a SNP (r5362331) known to be a factor in the predisposition to develop HD. The second and third interactions (16 and 17) spanned the Anchor and Zone 1 and covered 185 kb and 174 kb, respectively. Last, we tested the absence or presence of all conditional interactions in individual HD samples. In the HD-Sym samples, we found the presence of at least one of the conditional markers (15, 16 and 17) in six out of seven samples (FIG. 3). A summary of all the interactions that were evaluated in this study are shown in FIG. 4 and FIG. 5. Table 18 gives odds ratios. Table 13 shows chromosome interactions that did not show any differences between subgroups.

Discussion

Problem Statement and Results Summary

While it is well-known that individuals with greater than 39 CAG-repeats will get HD, the clinical onset of disease varies widely amongst individual patients and the factors that influence when the disease manifests clinically are less well characterized. Here we used EpiSwitch™, an industrial platform for assessing chromatin architecture, to evaluate the epigenomic landscape of the HTT locus in HD patients and healthy, unaffected controls. We identified a set of seven interactions that when taken together as a CCS, could differentiate HD from unaffected controls and more importantly, could differentiate between presymptomatic and symptomatic HD patients. One of these interactions, specific for symptomatic HD, contains a SNP (r5362331) shown to be associated with a predisposing disease haplogroup. When taken together, these results show that a simple, non-invasive blood-based test evaluating a CCS can serve as a surrogate biomarker for assessing disease progression in HD.

Biological Relevance

While it is known that the poly-Q repeat tract expansion and production of mHTT are the underlying causes of HD, the molecular events leading to the development of clinical symptoms are less well characterized. Several studies have looked at SNPs within the HTT locus as a potential contributor to disease onset. One recent SNP genotyping study of HD patients identified ~41 SNPs heterozygous in at least 30% of the patients, including the r5362331 C/T SNP in exon 50 of the HTT gene. Perhaps more biologically relevant is that when the r5362331 SNP is allele-selectively knocked down using anti-sense oligonucleotides, siRNAs or miRNA, a dramatic reduction in the levels of mHTT protein is achieved both in vitro and in vivo suggesting that this SNP and its surrounding genomic landscape play an important role in regulating mHTT levels. In this study, we observed a chromosome conformation (15) that was present only in HD-Sym patients and absent in HD-Asy and HCs that overlapped with the r5362331 SNP. This suggests that the production of neurotoxic mHTT in patients that have increased poly-Q tracts and a genetic predisposition to the early development of HD by the presence of the r5362331 SNP may be regulated at the level of higher order chromatin structure. Another outstanding question in HD is how the disease is inherited in cases where neither parent has received a diagnosis. The two main prevailing hypotheses posit that 1) the carrier parent could have passed away from another factor before the onset of the disease and 2) "unstable" CAG repeat tracts expand with each generation. A third possibility also exists, in that at mid-range (35-50) repeats, individuals could be carriers without manifestation of the disease, but their progeny might be unable to compensate for the genetic defect through undefined mechanisms and will develop the disease. The HD patients evaluated in this study all had CAG repeats in this mid-range, raising the possibility that potential compensatory mechanisms in disease development may be mediated through differences in genomic architecture.

Clinical Relevance

HD is unique in that there exists a simple test to definitively diagnose the disease, HTT gene sequencing and measurement of CAG repeat number. For clinical care and clinical trials, there are also several tests to measure disease severity, such as the Unified Huntington's Disease Rating Scale (UHDRS), the Shoulson-Fahn Scale, and the Mini-Mental State Examination (MMSE). While these assessments measure different elements of an HD patients physical and mental well-being as a surrogate for disease severity, they are all subjective in nature and most are not specific for HD. What is missing are concrete molecular tools to monitor disease progression.

There are presently 22 therapeutic agents for treating HD in different stages of preclinical and clinical development, half of which are in Phase 2 or Phase 3. Once further validated, the CCS reported here could be used in clinical trials as a surrogate outcome biomarker to assess the therapeutic efficacy of the drug in question. In addition to monitoring a symptomatic patient's response to a particular therapy in clinical trials, another advantage of the approach described here lies in the information that can be obtained for presymptomatic patients. For most HD patients, the presymptomatic period can last decades. Five of the seven (i3-i7) interactions identified here clearly separate presymptomatic HD patients from symptomatic ones, and when further validated could serve as an "early warning" indicator test for the onset of HD symptoms in presymptomatic carriers.

This study gives first evidence of detectable conditional differences in chromatin architecture specific for the manifestation of HD and correlated with known disease haplotypes. The major strength of this study lies in the unique approach, which is based on the latest developments in understanding the regulatory role of genomic architecture. While there have been several historical studies in HD aimed at developing disease progression biomarkers based on clinical, imaging and molecular measures, to the best of our knowledge this is the first time that the assessment of higher order chromatin structures in a clinically accessible biofluid has been applied in HD.

TABLE 1a

| Probe | Gene Locus | Probe_Count_Total | Probe_Count_Sig |
|---|---|---|---|
| C6orf58_6_127480771_127483471_127600017_127604343_FR | C6orf58 | 10 | 5 |
| NEFH_22_29442588_29445314_29482081_29484217_RR | NEFH | 16 | 10 |
| IL1A_2_112765786_112772711_112810765_112813086_RR | IL1A | 23 | 15 |
| FARP1_13_98271575_98282700_98346930_98348486_FR | FARP1 | 26 | 26 |
| PRKCA_17_66441276_66447067_66475597_66481312_RF | PRKCA | 30 | 16 |
| RNU6-1264P_17_6162286_6163870_6195952_6199184_FR | RNU6-1264P | 31 | 16 |
| PON2_7_95405100_95420940_95465337_95474032_FR | PON2 | 40 | 19 |
| CAPN9_1_230738572_230739927_230752057_230757333_RR | CAPN9 | 50 | 23 |
| ATXN7L1_7_105654123_105657510_105741521_105750599_FR | ATXN7L1 | 130 | 61 |
| CNTNAP2_7_146728706_146734820_146785878_146792823_RF | CNTNAP2 | 144 | 60 |
| CTNNA3_10_66299269_66302507_66496211_66513003_FF | CTNNA3 | 151 | 46 |
| ZFPM2_8_105632010_105638904_105814873_105824107_FR | ZFPM2 | 186 | 68 |
| ALDH1A2_15_58325151_58334051_58485549_58488054_FR | ALDH1A2 | 185 | 70 |
| ALDH1A2_15_58325151_58334051_58538695_58540885_FF | ALDH1A2 | 185 | 70 |
| MAGI2_7_79009346_79018304_79275810_79284623_RF | MAGI2 | 186 | 80 |
| FER1L6_8_123963222_123969450_124085753_124093275_FR | FER1L6 | 98 | 13 |
| UBQLN2_X_56536168_56538402_56570114_56575112_FR | UBQLN2 | 10 | 7 |

TABLE 1b

| HyperG_Stats | FDR_HyperG | Percent_Sig | logFC | AveExpr | t |
|---|---|---|---|---|---|
| 0.192504768 | 0.761792372 | 50 | −0.206940905 | −0.206940905 | −7.657670128 |
| 0.012576275 | 0.174966022 | 62.5 | 0.155885782 | 0.155885782 | 12.07017614 |
| 0.001213793 | 0.03415703 | 65.22 | 0.130559454 | 0.130559454 | 3.67899153 |
| 0.000000000000171 | 0.000000000079 | 100 | 0.254822215 | 0.254822215 | 14.73928749 |
| 0.013706774 | 0.176284348 | 53.33 | 0.24251793 | 0.24251793 | 7.451573283 |
| 0.019964247 | 0.210078331 | 51.61 | −0.152642021 | −0.152642021 | −9.03898498 |
| 0.032185744 | 0.276690843 | 47.5 | −0.178366996 | −0.178366996 | −5.268810519 |
| 0.029727242 | 0.269876723 | 46 | −0.224588757 | −0.224588757 | −8.238208751 |
| 0.000354202 | 0.018221718 | 46.92 | 0.189559955 | 0.189559955 | 6.597539924 |
| 0.011284771 | 0.170730832 | 41.67 | −0.440614155156995 | −0.440614155156995 | −7.4296031698139 |
| 0.713857099 | 1 | 30.46 | −0.436584531378388 | −0.436584531378387 | −14.2285764776972 |
| 0.122432344 | 0.622894915 | 36.56 | −0.425339105073479 | −0.425339105073479 | −10.493629902935 |
| 0.063739285 | 0.421589843 | 37.84 | 0.34586199024656 | 0.34586199024656 | 13.4772416929847 |
| 0.063739285 | 0.421589843 | 37.84 | 0.339861526563037 | 0.339861526563037 | 7.22282802700005 |
| 0.00139007 | 0.035755702 | 43.01 | 0.34944598213495 | 0.34944598213495 | 10.5772811324938 |
| 0.999996196 | 1 | 13.27 | 0.350542987884941 | 0.350542987884941 | 5.66944350076527 |
| 0.016370015 | 0.18948292 | 70 | 0.353892612578078 | 0.353892612578078 | 2.69374295077173 |

TABLE 1c

| P.Value | adj.P.Val | B | FC | FC_1 | LS | Loop detected |
|---|---|---|---|---|---|---|
| 0.000000338 | 8.58E−06 | 6.769090112 | 0.866372344 | −1.154238137 | −1 | Control |
| 0.000000000262 | 7.50E−08 | 13.89074006 | 1.114105444 | 1.114105444 | 1 | ALS |
| 0.001613314 | 0.006000711 | −1.70129901 | 1.094718133 | 1.094718133 | 1 | ALS |

TABLE 1c-continued

| P.Value | adj.P.Val | B | FC | FC_1 | LS | Loop detected |
|---|---|---|---|---|---|---|
| 0.00000000000858 | 1.48E−08 | 17.19553875 | 1.193188696 | 1.193188696 | 1 | ALS |
| 0.0000005 | 1.15E−05 | 6.37489208 | 1.183055643 | 1.183055643 | 1 | ALS |
| 0.0000000281 | 1.46E−06 | 9.26023757 | 0.899601504 | −1.111603299 | −1 | Control |
| 0.000045 | 0.000343598 | 1.852676493 | 0.883702704 | −1.131602286 | −1 | Control |
| 0.000000115 | 3.91E−06 | 7.847763841 | 0.85583895 | −1.168444134 | −1 | Control |
| 0.0000027 | 3.98E−05 | 4.678642967 | 1.140415818 | 1.140415818 | 1 | ALS |
| 5.21452107638594E−07 | 1.18E−05 | 6.332521031 | 0.736820877 | −1.357181957 | −1 | Control |
| 1.58303956750015E−11 | 1.70E−08 | 16.61028384 | 0.738881785 | −1.353396471 | −1 | Control |
| 2.63975825723201E−09 | 2.70E−07 | 11.61504783 | 0.744663678 | −1.342888111 | −1 | Control |
| 4.03123106207005E−11 | 2.85E−08 | 15.71064142 | 1.270910107 | 1.270910107 | 1 | ALS |
| 7.77879601584934E−07 | 1.61E−05 | 5.930445637 | 1.265635109 | 1.265635109 | 1 | ALS |
| 2.32055637317047E−09 | 2.48E−07 | 11.7426843 | 1.27407127 | 1.27407127 | 1 | ALS |
| 0.0000188398197223922 | 0.000175073 | 2.726108027 | 1.275040425 | 1.275040425 | 1 | ALS |
| 0.0144551346098748 | 0.035577015 | −3.813817915 | 1.278004231 | 1.278004231 | 1 | ALS |

TABLE 1d

| Probe sequence | Probe Location | |
|---|---|---|
| 60 mer | Chr | Start1 |
| TCACCACACATCACCCCCTTGCTCCTCCTCGAGTCTTGGTGACCACAACAGGGTGCCACC (SEQ ID NO: 2) | 6 | 127483440 |
| GAGGTGGGTGAATCATGAGGTCAAGGGTTCGACAATAGTTGAGAATCTCCAACCACCTGG (SEQ ID NO: 3) | 22 | 29442590 |
| GGCCTTATAGTCAGCTGATCAGGTGAAATCGATTGGTCCTTAGGATCAGCTACCATTTGC (SEQ ID NO: 4) | 2 | 112765788 |
| GAGGCAGGCGGATCACAAAGTCAAAAGATCGATAACTTCAATAATAGTTACAGATGCAAA (SEQ ID NO: 5) | 13 | 98282669 |
| AGCACCATATCTGGGATGTAGCTATTGCTCGAGATTGCAGTGAGCTGTGATCACACCTCT (SEQ ID NO: 6) | 17 | 66441278 |
| TCTTCCCTCTTTTTAAAACCACCATTCATCGACCCCACACATCCTGTGCCACTCTACTGC (SEQ ID NO: 7) | 17 | 6163839 |
| TAACCATTATGCATCACTAACATAGCATTCGATATGATATGCTCAGTTTAGTTAGGGAAA (SEQ ID NO: 8) | 7 | 95420909 |
| GGCTCAGGAAGAGAACTATTTGTCTCTTTCGACACGCACATGCAGGACACTCACACGTAG (SEQ ID NO: 9) | 1 | 230738574 |
| GTTGGGTGGATCCCTTGAGCTCAGGAATTCGAAGAATGATTTTTCAGCCCGTGTGGAAGG (SEQ ID NO: 10) | 7 | 105657479 |
| ATCAAAAGAAAATAGATACTTGTCTTACTCGAGTTGAATAAAATCCTCAGCTTTCTGTCC (SEQ ID NO: 11) | 7 | 146728708 |
| AAAAGAAACTGTGAAAAGTTGTCACATTTCGATTAAATCCAAAAAGGTCTTCTATGAGGC (SEQ ID NO: 12) | 10 | 66302476 |
| TTAAAAGTATAGTAGTTGGCATTAACATTCGACCTTTTTCTGTTTCAGTAACCAACCCAG (SEQ ID NO: 13) | 8 | 105638873 |
| CATCAACTAATAGTTAAACATTATAATATCGACTGAAGACCTTTCATACTGTAAGATTCA (SEQ ID NO: 14) | 15 | 58334020 |
| CATCAACTAATAGTTAAACATTATAATATCGAGTCTGCAGTGAGCTGAGATCACACTGCC (SEQ ID NO: 15) | 15 | 58334020 |
| TTATTCCTTTCCAAATAGTTAAAATTATTCGAAACTTTTAAGAATCAATATAAAATTTCC (SEQ ID NO: 16) | 7 | 79009348 |
| CATAATTATAAATTAAAAAATGACACTATCGATTATGTCCAGTGTTTCTTGGTTGGTGTC (SEQ ID NO: 17) | 8 | 123969419 |
| CAGAGCACTAAGATAGACTTCTAAGGTTTCGAGGCATATAGCTCCAGCTGTATTGAGGTA (SEQ ID NO: 18) | X | 56538371 |

TABLE 1e

| Probe Location | | 4 kb Sequence Location | | | | |
|---|---|---|---|---|---|---|
| End1 | Start2 | End2 | Chr | Start1 | End1 | Start2 | End2 |
| 127483469 | 127600019 | 127600048 | 6 | 127479470 | 127483469 | 127600019 | 127604018 |
| 29442619 | 29482083 | 29482112 | 22 | 29442590 | 29446589 | 29482083 | 29486082 |
| 112765817 | 112810767 | 112810796 | 2 | 112765788 | 112769787 | 112810767 | 112814766 |
| 98282698 | 98346932 | 98346961 | 13 | 98278699 | 98282698 | 98346932 | 98350931 |
| 66441307 | 66481281 | 66481310 | 17 | 66441278 | 66445277 | 66477311 | 66481310 |
| 6163868 | 6195954 | 6195983 | 17 | 6159869 | 6163868 | 6195954 | 6199953 |
| 95420938 | 95465339 | 95465368 | 7 | 95416939 | 95420938 | 95465339 | 95469338 |
| 230738603 | 230752059 | 230752088 | 1 | 230738574 | 230742573 | 230752059 | 230756058 |
| 105657508 | 105741523 | 105741552 | 7 | 105653509 | 105657508 | 105741523 | 105745522 |
| 146728737 | 146792792 | 146792821 | 7 | 146728707 | 146732707 | 146788822 | 146792821 |
| 66302505 | 66512972 | 66513001 | 10 | 66298506 | 66302505 | 66509002 | 66513001 |
| 105638902 | 105814875 | 105814904 | 8 | 105634903 | 105638902 | 105814875 | 105818874 |
| 58334049 | 58485551 | 58485580 | 15 | 58330050 | 58334049 | 58485551 | 58489550 |
| 58334049 | 58540854 | 58540883 | 15 | 58330050 | 58334049 | 58536884 | 58540883 |
| 79009377 | 79284592 | 79284621 | 7 | 79009377 | 79013347 | 79280622 | 79284621 |
| 123969448 | 124085755 | 124085784 | 8 | 123965449 | 123969448 | 124085755 | 124089754 |
| 56538400 | 56570116 | 56570145 | X | 56534401 | 56538400 | 56570116 | 56574115 |

TABLE 2a

| probe | PCR-Primer1_ID | PCR_Primer1 |
|---|---|---|
| C6orf58_6_127480771_127483471_127600017_127604343_FR | OBD112-021 | AAGCACTTCATTCTCCCCTCACC (SEQ ID NO: 19) |
| NEFH_22_29442588_29445314_29482081_29484217_RR | OBD112-057 | ACTGAGCAATGATGGCAACAAC (SEQ ID NO: 20) |
| IL1A_2_112765786_112772711_112810765_112813086_RR | OBD112-077 | CTAGGCCTGCGTTTCTCCGT (SEQ ID NO: 21) |
| FARP1_13_98271575_98282700_98346930_98348486_FR | OBD112-093 | AGTTCTCTCTAAGAACTCAAGGA (SEQ ID NO: 22) |
| PRKCA_17_66441276_66447067_66475597_66481312_RF | OBD112-101 | CCCCAGGCACTCACACCTTA (SEQ ID NO: 23) |
| RNU6-1264P_17_6162286_6163870_6195952_6199184_FR | OBD112-105 | GGGCACTCAACACCCTTTTGT (SEQ ID NO: 24) |
| PON2_7_95405100_95420940_95465337_95474032_FR | OBD112-125 | GATGGGAATCAAGGGCAAGGG (SEQ ID NO: 25) |
| CAPN9_1_230738572_230739927_230752057_230757333_RR | OBD112-145 | GCATTAGCCAGCAAGCATACCT (SEQ ID NO: 26) |
| ATXN7L1_7_105654123_105657510_105741521_105750599_FR | OBD112-177 | CACCGCCTGATGCAGGTCTT (SEQ ID NO: 27) |
| CNTNAP2_7_146728706_146734820_146785878_146792823_RF | OBD112-217 | GGCACTGTTGGTCTGAAGCAC (SEQ ID NO: 28) |
| CTNNA3_10_66299269_66302507_66496211_66513003_FF | OBD112-229 | GGTCTAGATGTCAGTCTTTCC (SEQ ID NO: 29) |
| ZFPM2_8_105632010_105638904_105814873_105824107_FR | OBD112-245 | GACTATAAATCTCTCCTTGTCAGC (SEQ ID NO: 30) |
| ALDH1A2_15_58325151_58334051_58485549_58488054_FR | OBD112-317 | CCTTACCCGACACCAGGTAGC (SEQ ID NO: 31) |
| ALDH1A2_15_58325151_58334051_58538695_58540885_FF | OBD112-309 | CCCGACACCAGGTAGCATTC (SEQ ID NO: 32) |
| MAGI2_7_79009346_79018304_79275810_79284623_RF | OBD112-329 | GGGCACCCCACTAGACCAC (SEQ ID NO: 33) |
| FER1L6_8_123963222_123969450_124085753_124093275_FR | OBD112-333 | ATTCTCTCCCTGGTAAATCCTGGT (SEQ ID NO: 34) |
| UBQLN2_X_56536168_56538402_56570114_56575112_FR | OBD112-337 | CGCCAGCTCAGCAGCAATAA (SEQ ID NO: 35) |

TABLE 2b

| PCR-Primer2_ID | PCR_Primer2 | GLMNET |
|---|---|---|
| OBD112-023 | ATACTCCCATCCCCTAGGCCC (SEQ ID NO: 36) | 0.799327478 |
| OBD112-059 | CCCTACGACTGGCAAACCCA (SEQ ID NO: 37) | −0.323299991 |
| OBD112-079 | CCCTGGCATTCACATCACCGA (SEQ ID NO: 38) | 0.422829791 |
| OBD112-095 | GTCAAGCAACTGTGTCTGGGG (SEQ ID NO: 39) | 0.471919696 |
| OBD112-103 | GGATCCACGATCTCCCTCCAC (SEQ ID NO: 40) | −0.379552353 |
| OBD112-107 | AGGTCAGGATGGGTACCGTTG (SEQ ID NO: 41) | 0.259971774 |
| OBD112-127 | CTGGGATGATTCCTCTGGACTTCT (SEQ ID NO: 42) | −1.132792925 |
| OBD112-147 | GGTGGGCCTGGGTTAGATGC (SEQ ID NO: 43) | 0.980123681 |
| OBD112-179 | CAGCTGGCCGATCCATCACC (SEQ ID NO: 44) | −0.201292203 |
| OBD112-219 | GAGAACGACGACCTGGCACT (SEQ ID NO: 45) | −0.613932219 |
| OBD112-231 | TCATCCTATCCTCTCCTAGC (SEQ ID NO: 46) | −0.36233865 |
| OBD112-247 | ACTGTAGGCCAACCAGAAG (SEQ ID NO: 47) | 0.541529302 |
| OBD112-319 | CTGGTCCAGTGTCAGCGTGT (SEQ ID NO: 48) | −0.562433398 |
| OBD112-311 | GTGACTCTGCACGCACTGTT (SEQ ID NO: 49) | 0.486039187 |
| OBD112-331 | AGGCTCAGCAGGTTTCTGCC (SEQ ID NO: 50) | −0.759217304 |

TABLE 2b-continued

| PCR-Primer2_ID | PCR_Primer2 | GLMNET |
|---|---|---|
| OBD112-335 | CTGGGCAGGTCATCCAGACAG (SEQ ID NO: 51) | −1.154344187 |
| OBD112-339 | TGCTAGGGCCGAGTAATCATC (SEQ ID NO: 52) | 0.146973789 |

TABLE 3

| Marker | GLMNET |
|---|---|
| OBD112-021/023 | 0.799327478 |
| OBD112-057/059 | −0.323299991 |
| OBD112-077/079 | 0.422829791 |
| OBD112-093/095 | 0.471919696 |
| OBD112-101/103 | −0.379552353 |
| OBD112-105/107 | 0.259971774 |
| OBD112-125/127 | −1.132792925 |
| OBD112-145/147 | 0.980123681 |
| OBD112-177/179 | −0.201292203 |
| OBD112-217/219 | −0.613932219 |
| OBD112-229/231 | −0.36233865 |
| OBD112-245/247 | 0.541529302 |
| OBD112-317/319 | −0.562433398 |
| OBD112-309/311 | 0.486039187 |
| OBD112-329/331 | −0.759217304 |
| OBD112-333/335 | −1.154344187 |
| OBD112-337/339 | 0.146973789 |

TABLE 4a

| Genes | Full Name |
|---|---|
| C6orf58 | Chromosome 6 Open Reading Frame 58 |
| NEFH | Neurofilament Heavy |
| IL1A | Interleukin 1 Alpha |
| FARP1 | FERM, ARH/RhoGEF And Pleckstrin Domain Protein 1 |
| PRKCA | Protein Kinase C Alpha |
| RNU6-1264P | RNA, U6 Small Nuclear 1264, Pseudogene |
| PON2 | Paraoxonase 2 |
| CAPN9 | Calpain 9 |
| ATXN7L1 | Ataxin 7 Like 1 |
| CNTNAP2 | Contactin Associated Protein-Like 2 |
| CTNNA3 | Catenin Alpha 3 |
| ZFPM2 | Zinc Finger Protein, FOG Family Member 2 |
| ALDH1A2 | Aldehyde Dehydrogenase 1 Family Member A2 |
| MAGI2 | Membrane Associated Guanylate Kinase, WW And PDZ Domain Containing 2 |
| FER1L6 | Fer-1 Like Family Member 6 |
| UBQLN2 | Ubiquilin 2 |

TABLE 4b

Activity
Protein Coding gene maintenance of neuronal caliber, intracellular transport to axons and dendrites, neuronal damage and susceptibility to amyotrophic lateral sclerosis (ALS)
various immune responses, inflammatory processes, hematopoiesis and cell injury, activates apoptosis, correlated with rheumatoid arthritis and Alzheimer's disease
dendritic growth in neurons, link between cytoskeleton to the cell membrane
diverse cellular signalling pathways, receptors for phorbol esters, cellular processes such as cell adhesion, cell transformation, cell cycle checkpoint, and cell volume control
Pseudogene, connected with the snRNA class
cellular antioxidant, human tissues and i-nembrane-bound, defence responses to pathogenic bacteria, protecting cells from oxidative stress
neurodegenerative processes and digestive tract, associated with gastric cancer
Protein Coding gene
regulates interactions between neurons and glia, associated with speech and language development, cell adhesion in nervous system

TABLE 4b-continued

Activity
Protein Coding gene cell-cell adhesion in muscle cells, related to arrhythmogenic right ventricular dysplasia
regulates hematopoiesis and cardiogenesis in mammals,
developing and adult tissues, posterior organ development, prevents spina bifida
dentatorubral and pallidoluysian atrophy
Protein Coding gene
in vivo protein degradation

TABLE 5a

Array_data_for_3_month_Samples

| probe | GeneLocus | Probe_Count_Total | Probe_Count_Sig |
|---|---|---|---|
| ZFPM2_8_104964347_104973135_105209447_105218050_FF | ZFPM2 | 187 | 6 |
| VEGFA_6_43733863_43737741_43777557_43780533_FR | VEGFA | 42 | 1 |
| ERBB4_2_212287088_212294815_212317329_212325591_FR | ERBB4 | 193 | 10 |
| ZFPM2_8_105209447_105218050_105302264_105310138_FF | ZFPM2 | 187 | 6 |
| PASD1_X_151600201_151608969_151687203_151692271_FR | PASD1 | 41 | 14 |
| GRM7_3_7259138_7267165_7394377_7401227_RF | GRM7 | 174 | 7 |
| GRIK2_6_102047545_102055341_102078831_102089392_FR | GRIK2 | 188 | 5 |
| SORCS2_4_7219417_7226457_7241158_7248673_FF | SORCS2 | 84 | 6 |
| LINGO2_9_28314155_28333777_28371887_28374860_FR | LINGO2 | 194 | 3 |

TABLE 5b

| HyperG_Stats | FDR_HyperG | Percent_Sig | logFC | AveExpr | t | P.Value | adj.P.Val |
|---|---|---|---|---|---|---|---|
| 0.067854625 | 0.99237389 | 3.21 | 0.272052749 | 7.772607282 | 3.665534368 | 0.001024476 | 0.999953189 |
| 0.475978534 | 1 | 2.38 | −0.142175177 | 14.62826333 | −2.054497284 | 0.049386319 | 0.999953189 |
| 0.000818098 | 0.03828697 | 5.18 | 0.383778852 | 7.597586859 | 3.176083618 | 0.003622402 | 0.999953189 |
| 0.067854625 | 0.99237389 | 3.21 | 0.229570464 | 9.577318093 | 2.801385891 | 0.00913346 | 0.999953189 |
| 7.57E−16 | 3.54E−13 | 34.15 | 0.341166309 | 9.148011765 | 2.62030276 | 0.01404442 | 0.999953189 |
| 0.01784403 | 0.37959119 | 4.02 | 0.306594489 | 9.301524803 | 2.334933566 | 0.026957376 | 0.999953189 |
| 0.16129386 | 1 | 2.66 | 0.286167252 | 9.345860096 | 2.824849044 | 0.008630812 | 0.999953189 |
| 0.001827031 | 0.0712542 | 7.14 | −0.222042969 | 10.03535881 | −2.171963051 | 0.038499943 | 0.999953189 |
| 0.570146657 | 1 | 1.55 | 0.40947654 | 6.9839738 | 2.811551759 | 0.008912387 | 0.999953189 |

TABLE 5c

| B | FC | FC_1 | LS | Loop detected |
|---|---|---|---|---|
| −1.464031868 | 1.207524741 | 1.207524741 | 1 | Fs |
| −3.802493578 | 0.906151904 | −1.103567731 | −1 | Sw |
| −2.223740309 | 1.304754929 | 1.304754929 | 1 | Fs |
| −2.785028975 | 1.172485811 | 1.172485811 | 1 | Fs |
| −3.046315984 | 1.266780276 | 1.266780276 | 1 | Fs |
| −3.440610909 | 1.236784796 | 1.236784796 | 1 | Fs |
| −2.750635647 | 1.219396451 | 1.219396451 | 1 | Fs |
| −3.654353119 | 0.857350501 | −1.166384109 | −1 | Sw |
| −2.770141569 | 1.328203808 | 1.328203808 | 1 | Fs |

TABLE 5d

| Probe sequence | Probe Location | | |
|---|---|---|---|
| 60 mer | Chr | Start1 | End1 |
| TATATTTAAAAATACATACTGGTATACATCGATCTCATGACTTTGCTATTATGCATAGTG (SEQ ID NO: 53) | 8 | 104973104 | 104973133 |
| CCCCAGCCCAGCAACCTGGCTCACCTGATCGAGTACATCTTCAAGCCATCCTGTGTGCCC (SEQ ID NO: 54) | 6 | 43737710 | 43737739 |
| TATAAATAATACAGCTCTATTTGCCTACTCGATTAAAGAATCATATTATATCCTTAATTC (SEQ ID NO: 55) | 2 | 212294784 | 212294813 |
| CACTATGCATAATAGCAAAGTCATGAGATCGAAAATGTTTGTCAAGCAGTAGGTTTTGGG (SEQ ID NO: 56) | 8 | 105218019 | 105218048 |

TABLE 5d-continued

| Probe sequence | Probe Location | | |
|---|---|---|---|
| 60 mer | Chr | Start1 | End1 |
| GATTTTAGAATCTCTAACAAGGCTGCAATCGAGGTTAGCTGCTGCAGAAAGAAGAGAAAA (SEQ ID NO: 57) | X | 151608938 | 151608967 |
| GGTGACTAAAATGAGATTGCATTTTCTTTCGACCATTTGGCCAGCATGCCAAACACTGGT (SEQ ID NO: 58) | 3 | 7259140 | 7259169 |
| TAACCTCTCCTTTCTTAGGTTCTCCATATCGATAGAAAATTGTCTGCAGCCCTTAATGCC (SEQ ID NO: 59) | 6 | 102055310 | 102055339 |
| AGCTCACGGTCAGTGCCGTTCCGTTTGCTCGAATAAAGAACAAGGACCTTAAAAAATAGA (SEQ ID NO: 60) | 4 | 7226426 | 7226455 |
| AAAGTCATACAACTACTATGTAAGATATTCGAATACCTGTTAGAATAGGTGAAGGTTTAT (SEQ ID NO: 61) | 9 | 28333746 | 28333775 |

TABLE 5e

| Probe Location | | 4 kb Sequence Location | | | | |
|---|---|---|---|---|---|---|
| Start2 | End2 | Chr | Start1 | End1 | Start2 | End2 |
| 105218019 | 105218048 | 8 | 104969134 | 104973133 | 105214049 | 105218048 |
| 43777559 | 43777588 | 6 | 43733740 | 43737739 | 43777559 | 43781558 |
| 212317331 | 212317360 | 2 | 212290814 | 212294813 | 212317331 | 212321330 |
| 105310107 | 105310136 | 8 | 105214049 | 105218048 | 105306137 | 105310136 |
| 151687205 | 151687234 | X | 151604968 | 151608967 | 151687205 | 151691204 |
| 7401196 | 7401225 | 3 | 7259140 | 7263139 | 7397226 | 7401225 |
| 102078833 | 102078862 | 6 | 102051340 | 102055339 | 102078833 | 102082832 |
| 7248642 | 7248671 | 4 | 7222456 | 7226455 | 7244672 | 7248671 |
| 28371889 | 28371918 | 9 | 28329776 | 28333775 | 28371889 | 28375888 |

TABLE 6a

Array_data_for_6_month_Samples

| probe | GeneLocus | Probe_Count_Total | Probe_Count_Sig | HyperG_Stats |
|---|---|---|---|---|
| ZFPM2_8_104964347_104973135_105209447_105218050_FF | ZFPM2 | 187 | 8 | 0.007868339 |
| VEGFA_6_43733863_43737741_43777557_43780533_FR | VEGFA | 42 | 1 | 0.472787206 |
| ERBB4_2_212287088_212294815_212317329_212325591_FR | ERBB4 | 193 | 13 | 8.61E−06 |
| ZFPM2_8_105209447_105218050_105302264_105310138_FF | ZFPM2 | 187 | 8 | 0.007868339 |
| PASD1_X_151600201_151608969_151687203_151692271_FR | PASD1 | 41 | 18 | 1.87E−22 |
| GRM7_3_7259138_7267165_7394377_7401227_RF | GRM7 | 174 | 6 | 0.049498361 |
| GRIK2_6_102047545_102055341_102078831_102089392_FR | GRIK2 | 188 | 6 | 0.066833261 |
| SORCS2_4_7219417_7226457_7241158_7248673_FF | SORCS2 | 84 | 3 | 0.134527864 |
| LINGO2_9_28314155_28333777_28371887_28374860_FR | LINGO2 | 194 | 4 | 0.337532174 |

TABLE 6b

| FDR_HyperG | Percent_Sig | logFC | AveExpr | t | P.Value | adj.P.Val |
|---|---|---|---|---|---|---|
| 0.204139683 | 4.28 | 0.214103447 | 7.772607282 | 2.884747708 | 0.007463232 | 0.999935724 |
| 1 | 2.38 | −0.142760759 | 14.62826333 | −2.062959216 | 0.04851942 | 0.999935724 |
| 0.001005104 | 6.74 | 0.365781024 | 7.597586859 | 3.027136877 | 0.005258488 | 0.999935724 |
| 0.204139683 | 4.28 | 0.23990173 | 9.577318093 | 2.927455517 | 0.006723676 | 0.999935724 |
| 8.73E−20 | 43.9 | 0.331193838 | 9.148011765 | 2.543709927 | 0.016785386 | 0.999935724 |
| 0.825561956 | 3.45 | 0.354666043 | 9.301524803 | 2.701032396 | 0.011610123 | 0.999935724 |
| 1 | 3.19 | 0.294782642 | 9.345860096 | 2.909894328 | 0.007018965 | 0.999935724 |
| 1 | 3.57 | −0.229277936 | 10.03535881 | −2.242733507 | 0.033029594 | 0.999935724 |
| 1 | 2.06 | 0.440106238 | 6.9839738 | 3.021861688 | 0.005327738 | 0.999935724 |

TABLE 6c

| B | FC | FC_1 | LS | Loop detected |
|---|---|---|---|---|
| −2.662323695 | 1.159982827 | 1.159982827 | 1 | Fs |
| −3.791998096 | 0.905784176 | −1.104015754 | −1 | Sw |
| −2.449689974 | 1.288579031 | 1.288579031 | 1 | Fs |
| −2.598930246 | 1.18091222 | 1.18091222 | 1 | Fs |
| −3.154405805 | 1.25805399 | 1.25805399 | 1 | Fs |
| −2.930776901 | 1.278689554 | 1.278689554 | 1 | Fs |
| −2.625038885 | 1.226700147 | 1.226700147 | 1 | Fs |
| −3.562656794 | 0.853061739 | −1.172248096 | −1 | Sw |
| −2.457630227 | 1.35670423 | 1.35670423 | 1 | Fs |

Fs = Faster
SW = Slower

TABLE 6d

| Probe sequence | | Probe Location | |
|---|---|---|---|
| 60 mer | Chr | Start1 | End1 |
| TATATTTAAAAATACATACTGGTATACATCGATCTCATGACTTTGCTATTATGCATAGTG (SEQ ID NO: 62) | 8 | 104973104 | 104973133 |
| CCCCAGCCCAGCAACCTGGCTCACCTGATCGAGTACATCTTCAAGCCATCCTGTGTGCCC (SEQ ID NO: 63) | 6 | 43737710 | 43737739 |
| TATAAATAATACAGCTCTATTTGCCTACTCGATTAAAGAATCATATTATATCCTTAATTC (SEQ ID NO: 55) | 2 | 212294784 | 212294813 |
| CACTATGCATAATAGCAAAGTCATGAGATCGAAAATGTTTGTCAAGCAGTAGGTTTTGGG (SEQ ID NO: 64) | 8 | 105218019 | 105218048 |
| GATTTTAGAATCTCTAACAAGGCTGCAATCGAGGTTAGCTGCTGCAGAAAGAAGAGAAAA (SEQ ID NO: 65) | X | 151608938 | 151608967 |
| GGTGACTAAAATGAGATTGCATTTTCTTTCGACCATTTGGCCAGCATGCCAAACACTGGT (SEQ ID NO: 66) | 3 | 7259140 | 7259169 |
| TAACCTCTCCTTTCTTAGGTTCTCCATATCGATAGAAAATTGTCTGCAGCCCTTAATGCC (SEQ ID NO: 67) | 6 | 102055310 | 102055339 |
| AGCTCACGGTCAGTGCCGTTCCGTTTGCTCGAATAAAGAACAAGGACCTTAAAAAATAGA (SEQ ID NO: 68) | 4 | 7226426 | 7226455 |
| AAAGTCATACAACTACTATGTAAGATATTCGAATACCTGTTAGAATAGGTGAAGGTTTAT (SEQ ID NO: 69) | 9 | 28333746 | 28333775 |

TABLE 6e

| Probe Location | | 4 kb Sequence Location | | | | |
|---|---|---|---|---|---|---|
| Start2 | End2 | Chr | Start1 | End1 | Start2 | End2 |
| 105218019 | 105218048 | 8 | 104969134 | 104973133 | 105214049 | 105218048 |
| 43777559 | 43777588 | 6 | 43733740 | 43737739 | 43777559 | 43781558 |
| 212317331 | 212317360 | 2 | 212290814 | 212294813 | 212317331 | 212321330 |
| 105310107 | 105310136 | 8 | 105214049 | 105218048 | 105306137 | 105310136 |
| 151687205 | 151687234 | X | 151604968 | 151608967 | 151687205 | 151691204 |
| 7401196 | 7401225 | 3 | 7259140 | 7263139 | 7397226 | 7401225 |
| 102078833 | 102078862 | 6 | 102051340 | 102055339 | 102078833 | 102082832 |
| 7248642 | 7248671 | 4 | 7222456 | 7226455 | 7244672 | 7248671 |
| 28371889 | 28371918 | 9 | 28329776 | 28333775 | 28371889 | 28375888 |

TABLE 7a

| | | Inner_primers | |
|---|---|---|---|
| probe | PCR-Primer1_ID | PCR_Primer1 | |
| ZFPM2_8_104964347_104973135_105209447_105218050_FF | OBD112_773 | GCAGCACACAGGGAACTCTCTT (SEQ ID NO: 70) | |
| VEGFA_6_43733863_43737741_43777557_43780533_FR | OBD112_765 | GCTAGGAAGGGCCTGGGATG (SEQ ID NO: 71) | |

TABLE 7a-continued

| probe | Inner primers | |
|---|---|---|
| | PCR-Primer1_ID | PCR_Primer1 |
| ERBB4_2_212287088_212294815_212317329_212325591_FR | OBD112_477 | TCCAAAATGTTTAATACTGCCTAGA (SEQ ID NO: 72) |
| ZFPM2_8_105209447_105218050_105302264_105310138_FF | OBD112_777 | CAGCCACTGTAGAGAGCAGT (SEQ ID NO: 73) |
| PASD1_X_151600201_151608969_151687203_151692271_FR | OBD112_637 | ACTTCTTCCCAAGTCACTTTTGC (SEQ ID NO: 74) |
| GRM7_3_7259138_7267165_7394377_7401227_RF | OBD112_517 | TGACGAAGAAGCAATCCCTGGT (SEQ ID NO: 75) |
| GRIK2_6_102047545_102055341_102078831_102089392_FR | OBD112_501 | AATCTCTGCCCTCCTCTCATCTTG (SEQ ID NO: 76) |
| SORCS2_4_7219417_7226457_7241158_7248673_FF | OBD112_725 | AGGTATGCAGCCAGCCTGAG (SEQ ID NO: 77) |
| LINGO2_9_28314155_28333777_28371887_28374860_FR | OBD112_561 | CCGTGCCATATCCTCTGATTTATGC (SEQ ID NO: 78) |

TABLE 7b

| Inner_primers | | |
|---|---|---|
| PCR-Primer2_ID | PCR_Primer2 | GLMNET |
| OBD112_775 | TTGTTGAGCCCAGCAATTCCTTT (SEQ ID NO: 79) | -0.18669073 |
| OBD112_767 | CTCAGTGGGCACACACTCCA (SEQ ID NO: 80) | 0.15278372 |
| OBD112_479 | AGCCATGTGGTCTGGAATCT (SEQ ID NO: 81) | -0.24015518 |
| OBD112_779 | TAACCCACCAGCAGCAAGGT (SEQ ID NO: 82) | 0.22911033 |
| OBD112_647 | TGGCCATCTTGCTTTGCCTC (SEQ ID NO: 83) | 0.52468015 |
| OBD112_519 | GGACCTACCTCCACTGGGTTG (SEQ ID NO: 84) | 0.10503793 |
| OBD112_503 | CATGTTCCCACAGCAAGGAAGTTA (SEQ ID NO: 85) | -0.13060979 |
| OBD112_727 | TTTCCGTGCCAGTGTCCTGT (SEQ ID NO: 86) | -0.1217346 |
| OBD112_563 | GGCTGACCTTCAACAGATTCGC (SEQ ID NO: 87) | 0.01500745 |

TABLE 8

| Gene | Marker | GLMNET |
|---|---|---|
| ERBB4_2 | OBD112_477.479_0.4ng | -0.24015518 |
| ZFPM2_8 | OBD112_773.775_6.5ng | -0.18669073 |
| GRIK2_6 | OBD112_501.503_0.8ng | -0.13060979 |
| SORCS2_4 | OBD112_725.727_3.25ng | -0.1217346 |
| LINGO2_9 | OBD112_561.563_13ng | 0.01500745 |
| GRM7_3 | OBD112_517.519_13ng | 0.10503793 |
| VEGFA_6 | OBD112_765.767_13ng | 0.15278372 |
| ZFPM2_8 | OBD112_777.779_6.5ng | 0.22911033 |
| PASD1_X | OBD112_637.647_3.25ng | 0.52468015 |

TABLE 9

| Genes | Full name | Activity |
|---|---|---|
| ZFPM2 | Zinc Finger Protein, FOG Family Member 2 | transcription factor, regulates the activity of GATA family protein, regulates GATA-target genes expression |
| VEGFA | Vascular Endothelial Growth Factor A | stimulates proliferation and migration of vascular endothelial cells, stimulates physiological and pathological angiogenesis, modulates tumor stage and progression |
| ERBB4 | Erb-B2 Receptor Tyrosine Kinase 4 | stimulates a variety of cellular responses including mitogenesis and differentiation, |
| PASD1 | PAS Domain Containing Repressor 1 | encodes a cancer-associated antigen, induces autologous T-cell responses, immunotherapeutic target for the treatment of various hematopoietic malignancies |
| GRM7 | Glutamate Metabotropic Receptor 7 | activates ionotropic and metabotropic glutamate receptors, involved in most aspects of normal brain function, perturbed in neuropathologic conditions |
| GRIK2 | Glutamate Ionotropic Receptor Kainate Type Subunit 2 | modulates neurophysiologic processes |
| SORCS2 | Sortilin Related VPS10 Domain Containing Receptor 2 | protein coding gene, over expression in the central nervous system |
| LINGO2 | Leucine Rich Repeat And Ig Domain Containing 2 | protein coding gene |

TABLE 10a

| N | Array_Probe | Primer1_ID |
|---|---|---|
| 1 | DCLK1_13_35749195_35757694_36000600_36005542_RR | OBD112_453 |
| 2 | GRM7_3_7259138_7267165_7394377_7401227_RF | OBD112_517 |
| 3 | LINGO2_9_28314155_28333777_28371887_28374860_FR | OBD112_561 |
| 4 | PASD1_X_151600201_151608969_151687203_151692271_FR | OBD112_637 |
| 5 | UBQLN2_X_56536168_56538402_56570114_56575112_RR | OBD112_757 |
| 6 | ZFPM2_8_104964347_104973135_105209447_105218050_FF | OBD112_773 |
| 7 | ZFPM2_8_105209447_105218050_105302264_105310138_FF | OBD112_777 |
| 8 | ZNF804B_7_89108281_89114839_89127203_89146680_RF | OBD112_797 |

TABLE 10c

| Hydrolysis_probe_ID | Hydrolysis_probe_Seq |
|---|---|
| OBD112_88_FAM | AGGTTGCTTTCGAAGTACAGATATCACT (SEQ ID NO: 104) |
| OBD112_57_FAM | ATTTTCTTTCGACCATTTGGCCAGCA (SEQ ID NO: 105) |
| OBD112_90_FAM | TTCTAACAGGTATTCGAATATCTTACATAGT (SEQ ID NO: 106) |
| OBD112_26_FAM | AAGTAACATTCGACAAACCTCTGGTAA (SEQ ID NO: 107) |
| OBD112_95_FAM | TATTCTCTTTGATCGAGGCATATAGCT (SEQ ID NO: 108) |

TABLE 10b

| Primer1_Seq | Primer2_ID | Primer2_Seq |
|---|---|---|
| TCTTGTACACGGTTGGTGGT (SEQ ID NO: 88) | OBD112_455 | TGTCACCTATGTGCTGAGTACTGG (SEQ ID NO: 89) |
| TGACGAAGAAGCAATCCCTGGT (SEQ ID NO: 90) | OBD112_519 | GGACCTACCTCCACTGGGTTG (SEQ ID NO: 91) |
| CCGTGCCATATCCTCTGATTTATGC (SEQ ID NO: 92) | OBD112_563 | GGCTGACCTTCAACAGATTCGC (SEQ ID NO: 93) |
| ACTTCTTCCCAAGTCACTTTTTGC (SEQ ID NO: 94) | OBD112_647 | TGGCCATCTTGCTTTGCCTC (SEQ ID NO: 95) |
| GGATATGCAGTTTTCCTGGCACTAC (SEQ ID NO: 96) | OBD112_759 | CATGCTAGGGCCGAGTAATCATCT (SEQ ID NO: 97) |
| GCAGCACACAGGGAACTCTCTT (SEQ ID NO: 98) | OBD112_775 | TTGTTGAGCCCAGCAATTCCTTT (SEQ ID NO: 99) |
| CAGCCACTGTAGAGAGCAGT (SEQ ID NO: 100) | OBD112_779 | TAACCCACCAGCAGCAAGGT (SEQ ID NO: 101) |
| AGTAGCTTCCCTGTTAGAGGTCTTG (SEQ ID NO: 102) | OBD112_799 | AGCCAGTGACTCCACAACTTCTT (SEQ ID NO: 103) |

TABLE 10c-continued

| Hydrolysis_probe_ID | Hydrolysis_probe_Seq | |
|---|---|---|
| OBD112_80_FAM | AAAGTCATGAGATCGATGTATACCAGTAT (SEQ ID NO: 109) | |
| OBD112_32_FAM | TTGACAAACATTTTCGATCTCATGACTT (SEQ ID NO: 110) | |
| OBD112_33_FAM | TGTGGCTCAGTCGACAGAAAGTACA (SEQ ID NO: 111) | |

TABLE 11a (i)

| probe | GeneLocus | Probe_Count_Total | Probe_Count_Sig |
|---|---|---|---|
| DCLK1_13_35749195_35757694_36000600_36005542_RR | DCLK1 | 182 | 3 |
| UBQLN2_X_56536168_56538402_56570114_56575112_RR | UBQLN2 | 10 | 7 |
| ZNF804B_7_89108281_89114839_89127203_89146680_RF | ZNF804B | 191 | 10 |

TABLE 11a (ii)

| HyperG_Stats | FDR_HyperG | Percent_Sig | logFC | AveExpr | t |
|---|---|---|---|---|---|
| 0.254316537 | 1 | 1.65 | 0.199442299 | 7.402197005 | 2.87151 |
| 0.000000000001 | 0.000000000386 | 70 | 0.283366605 | 9.419823948 | 2.114955 |
| 1.74E−05 | 0.002050325 | 5.24 | 0.228756351 | 9.389157739 | 2.52348 |

TABLE 11a (iii)

| P.Value | adj.P.Val | B | FC | FC_1 | Loop LS | detected |
|---|---|---|---|---|---|---|
| 0.007707652 | 0.999953189 | −2.681902147 | 1.14825439 | 1.14825439 | 0 | Faster |
| 0.043482517 | 0.999953189 | −3.726899057 | 1.217031581 | 1.217031581 | 0 | Faster |
| 0.017587875 | 0.999953189 | −3.182692934 | 1.171824364 | 1.171824364 | 0 | Faster |

TABLE 11b (i)

| probe | PCR-Primer1_ID | PCR_Primer1 |
|---|---|---|
| DCLK1_13_35749195_35757694_36000600_36005542_RR | OBD112_453 | TCTTGTACACGGTTGGTGGT (SEQ ID NO: 112) |
| UBQLN2_X_56536168_56538402_56570114_56575112_RR | OBD112_757 | GGATATGCAGTTTTCCTGGCACTAC (SEQ ID NO: 113) |
| ZNF80413_7_89108281_89114839_89127203_89146680_RF | OBD112_797 | AGTAGCTTCCCTGTTAGAGGTCTTG (SEQ ID NO: 114) |

TABLE 11b (ii)

| PCR-Primer2_ID | PCR_Primer2 | GLMNET |
|---|---|---|
| OBD112_455 | TGTCACCTATGTGCTGAGTACTGG (SEQ ID NO: 115) | 0.047800994 |
| OBD112_759 | CATGCTAGGGCCGAGTAATCATCT (SEQ ID NO: 116) | -0.013191036 |
| OBD112_799 | AGCCAGTGACTCCACAACTTCTT (SEQ ID NO: 117) | -0.025426843 |

TABLE 11c

| Marker | GLMNET |
|---|---|
| OBD112_453.455_3.25ng | 0.047801 |
| OBD112_757.759_13ng | -0.013191 |
| OBD112_797.799_1.6ng | -0.025427 |

TABLE 12a

| probe | GeneLocus | Loop detected | Probe sequence 60 mer |
|---|---|---|---|
| HTT_4_3088056_3090591_3182426_3183765_FRHTT | | HD_Negative | AGATCTAGTTCACAGTAGCACCAATATATC GACAGATAGCTGACATCATCCTCCCAATGT (SEQ ID NO: 118) |
| HTT_4_3076247_3078445_3182426_3183765_RRHTT | | HD_Negative | AGAGTACTTCCTAACTCCTACTGTACACTC GACAGATAGCTGACATCATCCTCCCAATGT (SEQ ID NO: 119) |
| HTT_4_3062575_3066389_3251623_3253432_RFHTT | | HD Positive | TATAACCAGTGCTCCTACGAAGGCCGCTTC GAAGTCTCAAACTTCACTTCTCCTGTGCGC (SEQ ID NO: 120) |
| HTT_4_3076247_3078445_3253432_3258164_RRHTT | | HD Positive | AGAGTACTTCCTAACTCCTACTGTACACTC GAGGATGATCGCTCCGACAGCTCCTCCAGC (SEQ ID NO: 121) |
| HTT_4_3070353_3072847_3212506_3214871_FRHTT | | HD_Negative | GGGTTTCGCCATGTTGGCCAGGCTGGTCTC GAAGTTGATGCATCTGTGCTCACGTTTGCA (SEQ ID NO: 122) |
| HTT_4_3088056_3090591_3212506_3214871_FFHTT | | HD Positive | AGATCTAGTTCACAGTAGCACCAATATATC GACTGTCTCCTGTTGGCCATCTCTCACCCT (SEQ ID NO: 123) |
| HTT_4_3088056_3090591_3167292_3170536_FRHTT | | HD_Negative | AGATCTAGTTCACAGTAGCACCAATATATC GAACTCCTGACCTTGTGATCCACCCACCTC (SEQ ID NO: 124) |

TABLE 12b

| Probe Location | | | | | | PCR- | |
|---|---|---|---|---|---|---|---|
| Chr | Start1 | End1 | Start2 | End2 | probe | Primer1_ID | PCR_Primer1 |
| 4 | 3090560 | 3090591 | 3182426 | 3182457 | HTT_4_3088056_3090591_3182426_3183765_FR | RD031_037 | GAATACCCAGGAATG CTTACTTGAGC (SEQ ID NO: 125) |
| 4 | 3076247 | 3076278 | 3182426 | 3182457 | HTT_4_3076247_3078445_3182426_3183765_RR | RD031_061 | ACCAAATGCCATCTG GGACACATCCA (SEQ ID NO: 126) |
| 4 | 3062575 | 3062606 | 3253401 | 3253432 | HTT_4_3062575_3066389_3251623_3253432_RF | RD031_185 | CCCGCTAAGTCCACC CCTCTGTA (SEQ ID NO: 127) |

TABLE 12b-continued

| | Probe Location | | | | | PCR- | |
|---|---|---|---|---|---|---|---|
| Chr | Start1 | End1 | Start2 | End2 | probe | Primer1_ID | PCR_Primer1 |
| 4 | 3076247 | 3076278 | 3253432 | 3253463 | HTT_4_3076247_3078445_3253432_3258164_RR | RD031_237 | ACCAAATGCCATCTG GGACACATCCA (SEQ ID NO: 128) |
| 4 | 3072816 | 3072847 | 3212506 | 3212537 | HTT_4_3070353_3072847_3212506_3214871_FR | RD031_241 | AGTCTGCCCACTGAG GTAACTAACAA (SEQ ID NO: 129) |
| 4 | 3090560 | 3090591 | 3214840 | 3214871 | HTT_4_3088056_3090591_3212506_3214871_FF | RD031_329 | GAATACCCAGGAATG CTTACTTGAGC (SEQ ID NO: 125) |
| 4 | 3090560 | 3090591 | 3167292 | 3167323 | HTT_4_3088056_3090591_3167292_3170536_FF | RD031_333 | GAATACCCAGGAATG CTTACTTGAGC (SEQ ID NO: 125) |

TABLE 12c

| PCR-Primer2_ID | PCR_Primer2 |
|---|---|
| RD031_039 | GATTCCAGCCACCCACCTTTCACAAG (SEQ ID NO: 129) |
| RD031_063 | TGATTCCAGCCACCCACCTTTCACAA (SEQ ID NO: 130) |
| RD031_187 | GAACCGCACTTACCCTCAGCAGT (SEQ ID NO: 131) |
| RD031_239 | GGACAAGCAGACACACTACCTGAACT (SEQ ID NO: 132) |
| RD031_243 | ATCCCCTGAAACAGAAGGACCTCGTG (SEQ ID NO: 133) |
| RD031_331 | GAGCCGTCTCATAATAACCTCAGGGT (SEQ ID NO: 134) |
| RD031_335 | CAGTGGTTTAGGGCAAAGAGAGGGAG (SEQ ID NO: 135) |

TABLE 13a

| probe | GeneLocus | Loop detected | Probe sequence 60 mer |
|---|---|---|---|
| HTT_4_3088056_3090591_3112545_3114867_FR | HTT | No difference | AGATCTAGTTCACAGTAGCACCAATATATC GACATTAAGTTCATGAGAGTCTTCTATATT (SEQ ID NO: 136) |
| HTT_4_3062575_3066389_3119060_3125597_RR | HTT | No difference | GCGCACAGGAGAAGTGAAGTTTGAGACTTC GAAAAAGGAATAAATTGAAAAATAGAGGAA (SEQ ID NO: 137) |
| HTT_4_3076247_3078445_3241592_3247577_RR | HTT | No difference | AGAGTACTTCCTAACTCCTACTGTACACTC GATGTTTTGGGTATTGAATGTGGTAAGTGG (SEQ ID NO: 138) |
| HTT_4_3080953_3084487_3253432_3258164_RR | HTT | No difference | ATCAAGACTGTATGGTACTGGCACAGGATC GAGGATGATCGCTCCGACAGCTCCTCCAGC (SEQ ID NO: 139) |
| HTT_4_3080953_3084487_3241592_3247577_RR | HTT | No difference | ATCAAGACTGTATGGTACTGGCACAGGATC GATGTTTTGGGTATTGAATGTGGTAAGTGG (SEQ ID NO: 140) |
| HTT_4_3080953_3084487_3112545_3114867_RR | HTT | No difference | ATCAAGACTGTATGGTACTGGCACAGGATC GACATTAAGTTCATGAGAGTCTTCTATATT (SEQ ID NO: 141) |
| HTT_4_3076247_3078445_3112545_3114867_RF | HTT | No difference | TGTCCAGTTAAATTGCAGATATTTCCGATC GAGTGTACAGTAGGAGTTAGGAAGTACTCT (SEQ ID NO: 142) |
| HTT_4_3080953_3084487_3167292_3170536_RR | HTT | No difference | ATCAAGACTGTATGGTACTGGCACAGGATC GAACTCCTGACCTTGTGATCCACCCACCTC (SEQ ID NO: 143) |

TABLE 13a-continued

| probe | GeneLocus | Loop detected | Probe sequence 60 mer |
|---|---|---|---|
| HTT_4_3038381_3040238_3088056_3090591_RF | HTT | No difference | AGATCTAGTTCACAGTAGCACCAATATATC GAATCTGGGTGTTTCAAAGACATCAACAAA (SEQ ID NO: 144) |
| HTT_4_3088056_3090591_3253432_3258164_FR | HTT | No difference | AGATCTAGTTCACAGTAGCACCAATATATC GAGGATGATCGCTCCGACAGCTCCTCCAGC (SEQ ID NO: 145) |
| HTT_4_3062575_3066389_3167292_3170536_FR | HTT | No difference | GGGTTTCACCATGTTGGCCAGGATGGTCTC GAACTCCTGACCTTGTGATCCACCCACCTC (SEQ ID NO: 146) |
| HTT_4_3088056_3090591_3251623_3253432_FF | HTT | No difference | AGATCTAGTTCACAGTAGCACCAATATATC GAAGCGGCCTTCGTAGGAGCACTGGTTATA (SEQ ID NO: 147) |
| HTT_4_3088056_3090591_3241592_3247577_FF | HTT | No difference | AGATCTAGTTCACAGTAGCACCAATATATC GACTAAGGTCAGCCCTCCGTGCTGGGGGCT (SEQ ID NO: 148) |

TABLE 13b

| Probe Location | | | | | | PCR-Primer1_IDPCR_Primer1 | |
|---|---|---|---|---|---|---|---|
| Chr | Start1 | End1 | Start2 | End2 | probe | | |
| 4 | 3090560 | 3090591 | 3112545 | 3112576 | HTT_4_3088056_3090591_3112545_3114867_FR | RD031_001 | GAATACCCAGGAATGC TTACTTGAGC (SEQ ID NO: 125) |
| 4 | 3062575 | 3062606 | 3119060 | 3119091 | HTT_4_3062575_3066389_3119060_3125597_RR | RD031_009 | GGTCCAGAGAACCGCA CTTACCC (SEQ ID NO: 149) |
| 4 | 3076247 | 3076278 | 3241592 | 3241623 | HTT_4_3076247_3078445_3241592_3247577_RR | RD031_025 | ACCAAATGCCATCTGG GACACATCCA (SEQ ID NO: 126) |
| 4 | 3080953 | 3080984 | 3253432 | 3253463 | HTT_4_3080953_3084487_3253432_3258164_RR | RD031_041 | TCCCTCTCAGAATCCT ACTTGGCTTC (SEQ ID NO: 150) |
| 4 | 3080953 | 3080984 | 3241592 | 3241623 | HTT_4_3080953_3084487_3241592_3247577_RR | RD031_057 | TCCCTCTCAGAATCCT ACTTGGCTTC (SEQ ID NO: 150) |
| 4 | 3080953 | 3080984 | 3112545 | 3112576 | HTT_4_3080953_3084487_3112545_3114867_RR | RD031_065 | TCCCTCTCAGAATCCT ACTTGGCTTC (SEQ ID NO: 150) |
| 4 | 3076247 | 3076278 | 3114836 | 3114867 | HTT_4_3076247_3078445_3112545_3114867_RF | RD031_097 | GAACAGTTTGTGGGTA GTATGCGGTC (SEQ ID NO: 151) |
| 4 | 3080953 | 3080984 | 3167292 | 3167323 | HTT_4_3080953_3084487_3167292_3170536_RR | RD031_149 | TCCCTCTCAGAATCCT ACTTGGCTTC (SEQ ID NO: 150) |
| 4 | 3038381 | 3038412 | 3090560 | 3090591 | HTT_4_3038381_3040238_3088056_3090591_RF | RD031_157 | GAATACCCAGGAATGC TTACTTGAGC (SEQ ID NO: 125) |
| 4 | 3090560 | 3090591 | 3253432 | 3253463 | HTT_4_3088056_3090591_3253432_3258164_FR | RD031_205 | GAATACCCAGGAATGC TTACTTGAGC (SEQ ID NO: 125) |
| 4 | 3066358 | 3066389 | 3167292 | 3167323 | HTT_4_3062575_3066389_3167292_3170536_FR | RD031_261 | TCTGGACAAGGTATCT GGAAGGCTGA (SEQ ID NO: 152) |
| 4 | 3090560 | 3090591 | 3253401 | 3253432 | HTT_4_3088056_3090591_3251623_3253432_FF | RD031_301 | GAATACCCAGGAATGC TTACTTGAGC (SEQ ID NO: 125) |

TABLE 13b-continued

| Probe Location | | | | | probe | PCR-Primer1_ID | PCR_Primer1 |
|---|---|---|---|---|---|---|---|
| Chr | Start1 | End1 | Start2 | End2 | | | |
| 4 | 3090560 | 3090591 | 3247546 | 3247577 | HTT_4_3088056_3090591_3241592_3247577_FFR | D031_337 | GAATACCCAGGAATGCTTACTTGAGC (SEQ ID NO: 125) |

TABLE 13c

| PCR-Primer2_id | PCR_Primer2 |
|---|---|
| RD031_003 | GCACTGCTCGCAATAGCCAAGAACTA (SEQ ID NO: 153) |
| RD031_011 | CTTGCTGACCCTCCTATGGATGG (SEQ ID NO: 154) |
| RD031_027 | GCACAGAGTTCCAACATTTCCTCCAC (SEQ ID NO: 155) |
| RD031_043 | GGACAAGCAGACACACTACCTGAACT (SEQ ID NO: 156) |
| RD031_059 | GCACAGAGTTCCAACATTTCCTCCAC (SEQ ID NO: 155) |
| RD031_067 | GCACTGCTCGCAATAGCCAAGAACTA (SEQ ID NO: 157) |
| RD031_099 | ACCAAATGCCATCTGGGACACATCCA (SEQ ID NO: 126) |
| RD031_151 | ACAGTGGTTTAGGGCAAAGAGAGGGA (SEQ ID NO: 158) |
| RD031_159 | GAAGAAGCCTCTGTTTGGTCTGGAAA (SEQ ID NO: 159) |
| RD031_207 | GGAAGGACAAGCAGACACACTACCTG (SEQ ID NO: 160) |
| RD031_263 | GTGGTTTAGGGCAAAGAGAGGGAGAT (SEQ ID NO: 161) |
| RD031_303 | TCCCCGAGTCCTGTGATGGCAAACT (SEQ ID NO: 161) |
| RD031_339 | ATGGCTACGGAAAGGGCATTCGGAC (SEQ ID NO: 163) |

TABLE 14

| Subject ID (Unique ID for each subject) | Disease or Control | Type of biospecimen (e.g. FFPE-primary/ metastatic, serum, blood, DNA etc.) | Age (At time of collection) | Gender (M or F) | Date of collection (TBD) | Ethnicity | Age at Diagnosis | Method of diagnosis |
|---|---|---|---|---|---|---|---|---|
| control 01 | Control | Whole blood 9 ml | 32 | F | 2017 Nov. 7 | Caucasian (White) | — | PCR |
| control 02 | Control | Whole blood 9 ml | 65 | F | 2017 Nov. 10 | Caucasian (White) | — | PCR |
| control 03 | Control | Whole blood 9 ml | 41 | M | 2017 Nov. 13 | Caucasian (White) | — | PCR |
| control 04 | Control | Whole blood 9 ml | 19 | M | 2017 Nov. 10 | Caucasian (White) | — | PCR |
| control 05 | Control | Whole blood 9 ml | 46 | M | 2017 Nov. 10 | Caucasian (White) | — | PCR |
| control 06 | Control | Whole blood 9 ml | 29 | F | 2017 Nov. 13 | Caucasian (White) | — | PCR |
| control 07 | Control | Whole blood 9 ml | 47 | F | 2017 Nov. 14 | Caucasian (White) | — | PCR |
| control 08 | Control | Whole blood 9 ml | 22 | M | 2017 Nov. 14 | Caucasian (White) | — | PCR |
| control 09 | Control | Whole blood 9 ml | 35 | F | 2017 Nov. 15 | Caucasian (White) | — | PCR |
| control 11 | Control | Whole blood 9 ml | 33 | M | 2017 Nov. 16 | Caucasian (White) | — | PCR |
| HD 01 | Huntington's | Whole blood 9 ml | 32 | M | 2017 Oct. 30 | Caucasian (White) | 27 | PCR |
| HD 02 | Huntington's | Whole blood 9 ml | 32 | F | 2017 Oct. 30 | Caucasian (White) | 29 | PCR |
| HD 03 | Huntington's | Whole blood 9 ml | 28 | F | 2017 Nov. 1 | Caucasian (White) | 25 | PCR |
| HD 12 | Huntington's | Whole blood 9 ml | 50 | M | 2017 Nov. 2 | Caucasian (White) | 46 | PCR |
| HD 05 | Huntington's | Whole blood 9 ml | 52 | M | 2017 Nov. 2 | Caucasian (White) | 49 | PCR |
| HD 06 | Huntington's | Whole blood 9 ml | 43 | M | 2017 Nov. 2 | Caucasian (White) | 35 | PCR |
| HD 08 | Huntington's | Whole blood 9 ml | 23 | F | 2017 Nov. 2 | Caucasian (White) | — | PCR |

TABLE 14-continued

| | | | | | | | | |
|---|---|---|---|---|---|---|---|---|
| HD 09 | Huntington's | Whole blood 9 ml | 21 | F | 2017 Nov. 2 | Caucasian (White) | — | PCR |
| HD 10 | Huntington's | Whole blood 9 ml | 38 | F | 2017 Nov. 2 | Caucasian (White) | 36 | PCR |
| HD 11 | Huntington's | Whole blood 9 ml | 34 | M | 2017 Nov. 15 | Caucasian (White) | 32 | PCR |

| Subject ID (Unique ID for each subject) | Genetic Test Results for CAG repeats | Recorded Symptoms | Medications at time of collection | Any other genetic test results if available | Test results for HIV | Test results for HBV | Test results for HCV | Test results for syphilis |
|---|---|---|---|---|---|---|---|---|
| control 01 | n1 = 17<br>n2 = 28 | no | no | no | neg | neg | neg | neg |
| control 02 | n1 < 35<br>n2 < 35 | no | no | no | neg | neg | neg | neg |
| control 03 | n1 < 35<br>n2 < 35 | no | no | no | neg | neg | neg | neg |
| control 04 | n1 = 17<br>n2 = 21 | no | no | no | neg | neg | neg | neg |
| control 05 | n1 = 15<br>n2 = 17 | no | no | no | neg | neg | neg | neg |
| control 06 | n1 < 35<br>n2 < 35 | no | no | no | neg | neg | neg | neg |
| control 07 | n1 < 35<br>n2 < 35 | no | no | no | neg | neg | neg | neg |
| control 08 | n1 = 19<br>n2 = 22 | no | no | no | neg | neg | neg | neg |
| control 09 | n1 < 35<br>n2 < 35 | no | no | no | neg | neg | neg | neg |
| control 11 | n1 < 35<br>n2 < 35 | no | no | no | neg | neg | neg | neg |
| HD 01 | n1 < 35<br>n2 = 48 | Irritability, chorea | no | no | neg | neg | neg | neg |
| HD 02 | n1 < 35<br>n2 = 42 | no | no | no | neg | neg | neg | neg |
| HD 03 | n1 = 20<br>n2 = 46 | Irritability | no | no | neg | neg | neg | neg |
| HD 12 | n1 = 20<br>n2 = 48 | Irritability, chorea | no | no | neg | neg | neg | neg |
| HD 05 | n1 < 35<br>n2 = 45 | Irritability, chorea | no | no | neg | neg | neg | neg |
| HD 06 | n1 = 22<br>n2 = 40 | Irritability, chorea | Tetrabenazine | no | neg | neg | neg | neg |
| HD 08 | n1 < 35<br>n2 = 44 | no | no | no | neg | neg | neg | neg |
| HD 09 | n1 = 22<br>n2 = 41 | no | no | no | neg | neg | neg | neg |
| HD 10 | n1 < 35<br>n2 = 45 | Irritability | no | no | neg | neg | neg | neg |
| HD 11 | n1 = 24<br>n2 = 43 | Irritability, chorea | Sertraline | no | neg | neg | neg | neg |

TABLE 15

| Zone | hg19 coordinates | hg38 coordinates |
|---|---|---|
| Anchor point CAG repeat site | chr4: 3055890-3097657 | chr4: 3054163-3095930 |
| Zone 1 | chr4: 3232680-3259897 | chr4: 3230953-3258170 |
| Zone 2 | chr4: 3107637-3130235 | chr4: 3105908-3128508 |
| Zone 3 | chr4: 3212999-3218545 | chr4: 3211272-3216818 |
| Zone 4 | chr4: 3161885-3185826 | chr4: 3160158-3184099 |
| Zone 5 | chr4: 3033588-3050187 | chr4: 3031861-3048460 |

TABLE 16

| | Healthy Controls (N = 10) | Huntington's Disease (N = 10) |
|---|---|---|
| Gender | | |
| Male (N, (%)) | 5 (50) | 5 (50) |
| Female, (N, (%)) | 5 (50) | 5 (50) |
| Ethnicity | | |
| Non-Hispanic or Latino | 10 (100) | 10 (100) |
| Race | | |
| White (N, (%)) | 10 (100) | 10 (100) |
| Huntington's Type | | |
| Symptomatic (N, (%)) | N/A | 7 (70) |
| Asymptomatic, (N, (%)) | N/A | 3 (30) |
| CAG repeat length (Average, (SD)) | 25.7 (5.4) | 44.2 (2.6) |
| Age at Diagnosis (Average, (SD)) | N/A | 34.9* (8.1) |
| Age at Sample Collection (Average, (SD)) | 36.9 (12.8) | 35.3 (10.0) |
| Disease Duration** (Years) (Average, (SD)) | N/A | 3.8 (1.9) |

TABLE 16-continued

|  | Healthy Controls (N = 10) | Huntington's Disease (N = 10) |
|---|---|---|
| % Reporting Irritibility | N/A | 70 |
| % Reporting Chorea | N/A | 50 |

*Age at Diagnosis was not available for 2 of the 10 HD patients
N/A = Not Applicable

TABLE 17

| Interaction ID | Zone5 | Anchor | Zone2 | Zone4 | Zone3 | Zone1 |
|---|---|---|---|---|---|---|
| RD031_025/27 |  | ✓ |  |  |  | ✓ |
| RD031_041/43 |  | ✓ |  |  |  | ✓ |
| RD031_057/59 |  | ✓ |  |  |  | ✓ |
| RD031_061/63 |  | ✓ |  | ✓ |  |  |
| RD031_065/67 |  | ✓ | ✓ |  |  |  |
| RD031_097/99 |  | ✓ | ✓ |  |  |  |
| RD031_009/11 |  | ✓ | ✓ |  |  |  |
| RD031_149/151 |  | ✓ |  | ✓ |  |  |
| RD031_237/239 |  | ✓ |  |  |  | ✓ |
| RD031_261/263 |  | ✓ |  | ✓ |  |  |
| RD031_157/159 | ✓ | ✓ |  |  |  |  |
| RD031_001/3 |  | ✓ | ✓ |  |  |  |
| RD031_329/331 |  | ✓ |  |  | ✓ |  |
| RD031_301/303 |  | ✓ |  |  |  | ✓ |
| RD031_337/339 |  | ✓ |  |  |  | ✓ |
| RD031_037/39 |  | ✓ |  | ✓ |  |  |
| RD031_185/187 |  | ✓ |  |  |  | ✓ |
| RD031_205/207 |  | ✓ |  |  |  | ✓ |
| RD031_241/243 |  | ✓ |  |  | ✓ |  |
| RD031_333/335 |  | ✓ | ✓ |  |  |  |

TABLE 18a

| Marker | HD01 | HD03 | HD05 | HD06 | HD10 | HD11 | HD12 | Detection rates |
|---|---|---|---|---|---|---|---|---|
| RD031_237.239 | 0 | 0 | 0 | 1 | 1 | 1 | 1 | 57.14 |
| RD031_329.331 | 0 | 1 | 1 | 1 | 1 | 1 | 1 | 85.71 |
| RD031_185.187 | 0 | 0 | 1 | 1 | 0 | 1 | 0 | 42.86 |

TABLE 18b

| 237.239 | | | |
|---|---|---|---|
|  | Symptoms | No Symptoms |  |
| Loop Present | 4 | 1 | risk ratio 0.8 |
| Loop Absent | 3 | 12 | risk ratio 4 |
|  |  |  | Odds ratio 16 |

TABLE 18c

| 329.331 | | | |
|---|---|---|---|
|  | Symptoms | No Symptoms |  |
| Loop Present | 6 | 1 | risk ratio 0.85714 |
| Loop Absent | 1 | 12 | risk ratio 11.1429 |
|  |  |  | Odds ratio 72 |

TABLE 18d

| 185.187 | | | |
|---|---|---|---|
|  | Symptoms | No Symptoms |  |
| Loop Present | 3 | 1 | risk ratio 0.75 |
| Loop Absent | 4 | 12 | risk ratio 3 |
|  |  |  | Odds ratio 9 |

TABLE 19

>GRM7_3_7259138_7267165_7394377_7401227_RF (SEQ ID NO: 164)
TTGGGCAAATTACTTATTCTGTATGAGTTTCAGTGTGCACATTCACCAAA
TGTGGATAATAATAATGGTTAACTCCTAGGATGTTTGTGAGAATTGAAAT
AATATATCATTCTTAGCCCAGTATAATCATTTAAATTTTTTTTTAGTAA
GCATTAGCTGGAATCATTGGTATTGTTTTTATTTTCTTATCTACCCTCAA
ACATTGAAAGTGTCTTGGAGCAGAAGTTGTATATTACATACTTTCAGAAT
CTCTCTACCATGGGGCCTTTTGCTTTAATTAATTTCTGCTATAATTAATT
GCTCTATTATGCCATTTTCTGATTTCATCCAAGACACACTCTAAATGTAT
<u>ATGACGAAGAAGCAATCCCTGGTGACTAAAATGAGATTGCATTTTCT</u>
<u>TTCGA</u>CCATTTGGCCAGCATGCCAAACACTGGTAAATTGGCATTCCAAAG
CTCACATTGGCTGATTGATAAATTCACTACTTTGGGCTCAGTTTTGCCAT
CTGTAAAGTGATGGTGATCAAATGAGCAAGTGTATTTATTTATTTTAAAA
ATACTTTTATTTTAGATTTTGGGATACATGTGTAAGTTTGCTATATAGGT
AAATTCATGTCATGGGAGTTTATTGTAAAGATTATTTCATCATCCAGGTA
CTAAGCCTAGTACACAATAGTTATTTTTTTTCTGATTCTTTTCCTCCTCC
CAACTT<u>CAACCCAGTGGAGGTAGG</u>TCCCAGTGTCTGTTGTCCCCCTCTTT
GTGTCCATGTGTTCTCATCATTTAGCCCCCACTTATAAGTGATAATATGT
GGT

The invention claimed is:

1. A process for selecting a human individual and treating the selected human individual, wherein the selected human individual is in need of therapy for amyotrophic lateral sclerosis (ALS), wherein selecting the human individual is by:
   detecting the absence of a first chromosome interaction,
   detecting the presence of a second chromosome interaction,
   detecting the presence of a third chromosome interaction,
   detecting the presence of a fourth chromosome interaction,
   detecting the presence of a fifth chromosome interaction,
   detecting the absence of a sixth chromosome interaction,
   detecting the absence of a seventh chromosome interaction,
   detecting the absence of an eighth chromosome interaction,
   detecting the presence of a ninth chromosome interaction,
   detecting the absence of a tenth chromosome interaction,
   detecting the absence of an eleventh chromosome interaction,
   detecting the absence of a twelfth chromosome interaction,
   detecting the presence of a thirteenth chromosome interaction,
   detecting the presence of a fourteenth chromosome interaction,
   detecting the presence of a fifteenth chromosome interaction,
   detecting the presence of a sixteenth chromosome interaction, and
   detecting the presence of a seventeenth chromosome interaction
   in a sample from the human individual;
   and treating the selected human individual for amyotrophic lateral sclerosis (ALS) by administering an agent which is therapeutic for amyotrophic lateral sclerosis (ALS);
   wherein said detecting comprises:
   (i) cross-linking of chromosome regions which have come together in a chromosome interaction;
   (ii) subjecting said cross-linked regions to cleavage to form cross-linked cleaved nucleic acid;
   (iii) ligating said cross-linked cleaved nucleic acid ends to form ligated nucleic acid; and
   (iv) detecting the presence or absence of the ligated nucleic acid;
   wherein:
   the ligated nucleic acid corresponding to the first chromosome interaction is detected by the probe sequence (SEQ ID NO: 2)
   TCACCACACATCACCCCCTTGCTCCTCCTCGAGTCTTGGTGACCACAAC
   AGGGTGCCACC, the ligated nucleic acid corresponding to the second chromosome interaction is detected by the probe sequence (SEQ ID NO: 3)
   GAGGTGGGTGAATCATGAGGTCAAGGGTTCGACAATAGTTGAGAATCTC
   CAACCACCTGG, the ligated nucleic acid corresponding to the third chromosome interaction is detected by the probe sequence (SEQ ID NO: 4)
   GGCCTTATAGTCAGCTGATCAGGTGAAATCGATTGGTCCTTAGGATCAGC
   TACCATTTGC, the ligated nucleic acid corresponding to the fourth chromosome interaction is detected by the probe sequence (SEQ ID NO: 5)
   GAGGCAGGCGGATCACAAAGTCAAAAGATCGATAACTTCAATAATAGTTA
   CAGATGCAAA, the ligated nucleic acid corresponding to the fifth chromosome interaction is detected by the probe sequence (SEQ ID NO: 6)
   AGCACCATATCTGGGATGTAGCTATTGCTCGAGATTGCAGTGAGCTGTGA
   TCACACCTCT, the ligated nucleic acid corresponding to the sixth chromosome interaction is detected by the probe sequence (SEQ ID NO: 7)
TCTTCCCTCTTTTTAAAACCACCATTCATCGACCCCACACATCCTGTGCC

ACTCTACTGC, the ligated nucleic acid corresponding to the seventh chromosome interaction is detected by the probe sequence (SEQ ID NO: 8)
TAACCATTATGCATCACTAACATAGCATTCGATATGATATGCTCAGTTTA

GTTAGGGAAA, the ligated nucleic acid corresponding to the eighth chromosome interaction is detected by the probe sequence (SEQ ID NO: 9)
GGCTCAGGAAGAGAACTATTTGTCTCTTTCGACACGCACATGCAGGACAC

TCACACGTAG, the ligated nucleic acid corresponding to the ninth chromosome interaction is detected by the probe sequence (SEQ ID NO: 10)
GTTGGGTGGATCCCTTGAGCTCAGGAATTCGAAGAATGATTTTTCAGCCC

GTGTGGAAGG, the ligated nucleic acid corresponding to the tenth chromosome interaction is detected by the probe sequence (SEQ ID NO: 11)
ATCAAAAGAAAATAGATACTTGTCTTACTCGAGTTGAATAAAATCCTCAG

CTTTCTGTCC, the ligated nucleic acid corresponding to the eleventh chromosome interaction is detected by the probe sequence (SEQ ID NO: 12)
AAAAGAAACTGTGAAAAGTTGTCACATTTCGATTAAATCCAAAAAGGTCT

TCTATGAGGC, the ligated nucleic acid corresponding to the twelfth chromosome interaction is detected by the probe sequence (SEQ ID NO: 13)
TTAAAAGTATAGTAGTTGGCATTAACATTCGACCTTTTTCTGTTTCAGTA

ACCAACCCAG, the ligated nucleic acid corresponding to the thirteenth chromosome interaction is detected by the probe sequence (SEQ ID NO: 14)
CATCAACTAATAGTTAAACATTATAATATCGACTGAAGACCTTTCATACT

GTAAGATTCA, the ligated nucleic acid corresponding to the fourteenth chromosome interaction is detected by the probe sequence (SEQ ID NO: 15)
CATCAACTAATAGTTAAACATTATAATATCGAGTCTGCAGTGAGCTGAGA

TCACACTGCC, the ligated nucleic acid corresponding to the fifteenth chromosome interaction is detected by the probe sequence (SEQ ID NO: 16)
TTATTCCTTTCCAAATAGTTAAAATTATTCGAAACTTTTAAGAATCAATA

TAAAATTTCC, the ligated nucleic acid corresponding to the sixteenth chromosome interaction is detected by the probe sequence (SEQ ID NO: 17)
CATAATTATAAATTAAAAAATGACACTATCGATTATGTCCAGTGTTTCTT

GGTTGGTGTC, and the ligated nucleic acid corresponding to the seventeenth chromosome interaction is detected by the probe sequence (SEQ ID NO: 18)
CAGAGCACTAAGATAGACTTCTAAGGTTTCGAGGCATATAGCTCCAGCTG

TATTGAGGTA.

2. The process according to claim 1 wherein the detecting comprises specific detection of the ligated nucleic acid by quantitative PCR (qPCR), wherein the probe comprises:
a fluorophore covalently attached to the 5' end of the probe, and/or
a quencher covalently attached to the 3' end of the probe.

* * * * *

SEQUENCE LISTING

<160> NUMBER OF SEQ ID NOS: 164

<210> SEQ ID NO 1
<211> LENGTH: 14
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t

<400> SEQUENCE: 1
ccgcgnggng gcag                                                   14

<210> SEQ ID NO 2
<211> LENGTH: 60
<212> TYPE: DNA
<213> ORGANISM: Homo sapiens

<400> SEQUENCE: 2
tcaccacaca tcaccccctt gctcctcctc gagtcttggt gaccacaaca gggtgccacc   60

<210> SEQ ID NO 3
<211> LENGTH: 60
<212> TYPE: DNA
<213> ORGANISM: Homo sapiens

<400> SEQUENCE: 3
gaggtgggtg aatcatgagg tcaagggttc gacaatagtt gagaatctcc aaccacctgg   60

<210> SEQ ID NO 4
<211> LENGTH: 60
<212> TYPE: DNA
<213> ORGANISM: Homo sapiens

<400> SEQUENCE: 4
ggccttatag tcagctgatc aggtgaaatc gattggtcct taggatcagc taccatttgc   60

<210> SEQ ID NO 5
<211> LENGTH: 60
<212> TYPE: DNA
<213> ORGANISM: Homo sapiens

<400> SEQUENCE: 5
gaggcaggcg gatcacaaag tcaaaagatc gataacttca ataatagtta cagatgcaaa   60

<210> SEQ ID NO 6
<211> LENGTH: 60
<212> TYPE: DNA
<213> ORGANISM: Homo sapiens

<400> SEQUENCE: 6
agcaccatat ctgggatgta gctattgctc gagattgcag tgagctgtga tcacacctct   60

<210> SEQ ID NO 7
<211> LENGTH: 60
<212> TYPE: DNA
<213> ORGANISM: Homo sapiens

<400> SEQUENCE: 7
tcttccctct ttttaaaacc accattcatc gaccccacac atcctgtgcc actctactgc   60

```
<210> SEQ ID NO 8
<211> LENGTH: 60
<212> TYPE: DNA
<213> ORGANISM: Homo sapiens

<400> SEQUENCE: 8
taaccattat gcatcactaa catagcattc gatatgatat gctcagttta gttagggaaa    60

<210> SEQ ID NO 9
<211> LENGTH: 60
<212> TYPE: DNA
<213> ORGANISM: Homo sapiens

<400> SEQUENCE: 9
ggctcaggaa gagaactatt tgtctctttc gacacgcaca tgcaggacac tcacacgtag    60

<210> SEQ ID NO 10
<211> LENGTH: 60
<212> TYPE: DNA
<213> ORGANISM: Homo sapiens

<400> SEQUENCE: 10
gttgggtgga tcccttgagc tcaggaattc gaagaatgat ttttcagccc gtgtggaagg    60

<210> SEQ ID NO 11
<211> LENGTH: 60
<212> TYPE: DNA
<213> ORGANISM: Homo sapiens

<400> SEQUENCE: 11
atcaaaagaa aatagatact tgtcttactc gagttgaata aaatcctcag ctttctgtcc    60

<210> SEQ ID NO 12
<211> LENGTH: 60
<212> TYPE: DNA
<213> ORGANISM: Homo sapiens

<400> SEQUENCE: 12
aaagaaaact gtgaaaagtt gtcacatttc gattaaatcc aaaaggtct tctatgaggc     60

<210> SEQ ID NO 13
<211> LENGTH: 60
<212> TYPE: DNA
<213> ORGANISM: Homo sapiens

<400> SEQUENCE: 13
ttaaaagtat agtagttggc attaacattc gaccttttc tgtttcagta accaacccag     60

<210> SEQ ID NO 14
<211> LENGTH: 60
<212> TYPE: DNA
<213> ORGANISM: Homo sapiens

<400> SEQUENCE: 14
catcaactaa tagttaaaca ttataatatc gactgaagac ctttcatact gtaagattca    60

<210> SEQ ID NO 15
<211> LENGTH: 60
<212> TYPE: DNA
<213> ORGANISM: Homo sapiens

<400> SEQUENCE: 15
```

```
catcaactaa tagttaaaca ttataatatc gagtctgcag tgagctgaga tcacactgcc    60

<210> SEQ ID NO 16
<211> LENGTH: 60
<212> TYPE: DNA
<213> ORGANISM: Homo sapiens

<400> SEQUENCE: 16
ttattccttt ccaaatagtt aaaattattc gaacttttta agaatcaata taaaatttcc    60

<210> SEQ ID NO 17
<211> LENGTH: 60
<212> TYPE: DNA
<213> ORGANISM: Homo sapiens

<400> SEQUENCE: 17
cataattata aattaaaaaa tgacactatc gattatgtcc agtgtttctt ggttggtgtc    60

<210> SEQ ID NO 18
<211> LENGTH: 60
<212> TYPE: DNA
<213> ORGANISM: Homo sapiens

<400> SEQUENCE: 18
cagagcacta agatagactt ctaaggtttc gaggcatata gctccagctg tattgaggta    60

<210> SEQ ID NO 19
<211> LENGTH: 23
<212> TYPE: DNA
<213> ORGANISM: Homo sapiens

<400> SEQUENCE: 19
aagcacttca ttctcccctc acc                                           23

<210> SEQ ID NO 20
<211> LENGTH: 22
<212> TYPE: DNA
<213> ORGANISM: Homo sapiens

<400> SEQUENCE: 20
actgagcaat gatggcaaca ac                                            22

<210> SEQ ID NO 21
<211> LENGTH: 20
<212> TYPE: DNA
<213> ORGANISM: Homo sapiens

<400> SEQUENCE: 21
ctaggcctgc gtttctccgt                                               20

<210> SEQ ID NO 22
<211> LENGTH: 25
<212> TYPE: DNA
<213> ORGANISM: Homo sapiens

<400> SEQUENCE: 22
agttctctct ctaagaactc aagga                                         25

<210> SEQ ID NO 23
<211> LENGTH: 20
<212> TYPE: DNA
<213> ORGANISM: Homo sapiens

<400> SEQUENCE: 23
```
ccccaggcac tcacacctta                                              20

<210> SEQ ID NO 24
<211> LENGTH: 21
<212> TYPE: DNA
<213> ORGANISM: Homo sapiens

<400> SEQUENCE: 24
gggcactcaa cacccttttg t                                            21

<210> SEQ ID NO 25
<211> LENGTH: 21
<212> TYPE: DNA
<213> ORGANISM: Homo sapiens

<400> SEQUENCE: 25
gatgggaatc aagggcaagg g                                            21

<210> SEQ ID NO 26
<211> LENGTH: 22
<212> TYPE: DNA
<213> ORGANISM: Homo sapiens

<400> SEQUENCE: 26
gcattagcca gcaagcatac ct                                           22

<210> SEQ ID NO 27
<211> LENGTH: 20
<212> TYPE: DNA
<213> ORGANISM: Homo sapiens

<400> SEQUENCE: 27
caccgcctga tgcaggtctt                                              20

<210> SEQ ID NO 28
<211> LENGTH: 21
<212> TYPE: DNA
<213> ORGANISM: Homo sapiens

<400> SEQUENCE: 28
ggcactgttg gtctgaagca c                                            21

<210> SEQ ID NO 29
<211> LENGTH: 21
<212> TYPE: DNA
<213> ORGANISM: Homo sapiens

<400> SEQUENCE: 29
ggtctagatg tcagtctttc c                                            21

<210> SEQ ID NO 30
<211> LENGTH: 24
<212> TYPE: DNA
<213> ORGANISM: Homo sapiens

<400> SEQUENCE: 30
gactataaat ctctccttgt cagc                                         24

<210> SEQ ID NO 31
<211> LENGTH: 21
<212> TYPE: DNA
<213> ORGANISM: Homo sapiens

```
<400> SEQUENCE: 31
ccttacccga caccaggtag c                                              21

<210> SEQ ID NO 32
<211> LENGTH: 20
<212> TYPE: DNA
<213> ORGANISM: Homo sapiens

<400> SEQUENCE: 32
cccgacacca ggtagcattc                                                20

<210> SEQ ID NO 33
<211> LENGTH: 19
<212> TYPE: DNA
<213> ORGANISM: Homo sapiens

<400> SEQUENCE: 33
gggcacccca ctagaccac                                                 19

<210> SEQ ID NO 34
<211> LENGTH: 24
<212> TYPE: DNA
<213> ORGANISM: Homo sapiens

<400> SEQUENCE: 34
attctctccc tggtaaatcc tggt                                           24

<210> SEQ ID NO 35
<211> LENGTH: 20
<212> TYPE: DNA
<213> ORGANISM: Homo sapiens

<400> SEQUENCE: 35
cgccagctca gcagcaataa                                                20

<210> SEQ ID NO 36
<211> LENGTH: 21
<212> TYPE: DNA
<213> ORGANISM: Homo sapiens

<400> SEQUENCE: 36
atactcccat cccctaggcc c                                              21

<210> SEQ ID NO 37
<211> LENGTH: 20
<212> TYPE: DNA
<213> ORGANISM: Homo sapiens

<400> SEQUENCE: 37
ccctacgact ggcaaaccca                                                20

<210> SEQ ID NO 38
<211> LENGTH: 21
<212> TYPE: DNA
<213> ORGANISM: Homo sapiens

<400> SEQUENCE: 38
ccctggcatt cacatcaccg a                                              21

<210> SEQ ID NO 39
<211> LENGTH: 21
<212> TYPE: DNA
<213> ORGANISM: Homo sapiens
```

-continued

```
<400> SEQUENCE: 39
gtcaagcaac tgtgtctggg g                                               21

<210> SEQ ID NO 40
<211> LENGTH: 21
<212> TYPE: DNA
<213> ORGANISM: Homo sapiens

<400> SEQUENCE: 40
ggatccacga tctccctcca c                                               21

<210> SEQ ID NO 41
<211> LENGTH: 21
<212> TYPE: DNA
<213> ORGANISM: Homo sapiens

<400> SEQUENCE: 41
aggtcaggat gggtaccgtt g                                               21

<210> SEQ ID NO 42
<211> LENGTH: 24
<212> TYPE: DNA
<213> ORGANISM: Homo sapiens

<400> SEQUENCE: 42
ctgggatgat tcctctggac ttct                                            24

<210> SEQ ID NO 43
<211> LENGTH: 20
<212> TYPE: DNA
<213> ORGANISM: Homo sapiens

<400> SEQUENCE: 43
ggtgggcctg ggttagatgc                                                 20

<210> SEQ ID NO 44
<211> LENGTH: 20
<212> TYPE: DNA
<213> ORGANISM: Homo sapiens

<400> SEQUENCE: 44
cagctggccg atccatcacc                                                 20

<210> SEQ ID NO 45
<211> LENGTH: 20
<212> TYPE: DNA
<213> ORGANISM: Homo sapiens

<400> SEQUENCE: 45
gagaacgacg acctggcact                                                 20

<210> SEQ ID NO 46
<211> LENGTH: 20
<212> TYPE: DNA
<213> ORGANISM: Homo sapiens

<400> SEQUENCE: 46
tcatcctatc ctctcctagc                                                 20

<210> SEQ ID NO 47
<211> LENGTH: 19
<212> TYPE: DNA
```

<213> ORGANISM: Homo sapiens

<400> SEQUENCE: 47
actgtaggcc aaccagaag                                            19

<210> SEQ ID NO 48
<211> LENGTH: 20
<212> TYPE: DNA
<213> ORGANISM: Homo sapiens

<400> SEQUENCE: 48
ctggtccagt gtcagcgtgt                                           20

<210> SEQ ID NO 49
<211> LENGTH: 20
<212> TYPE: DNA
<213> ORGANISM: Homo sapiens

<400> SEQUENCE: 49
gtgactctgc acgcactgtt                                           20

<210> SEQ ID NO 50
<211> LENGTH: 20
<212> TYPE: DNA
<213> ORGANISM: Homo sapiens

<400> SEQUENCE: 50
aggctcagca ggtttctgcc                                           20

<210> SEQ ID NO 51
<211> LENGTH: 21
<212> TYPE: DNA
<213> ORGANISM: Homo sapiens

<400> SEQUENCE: 51
ctgggcaggt catccagaca g                                         21

<210> SEQ ID NO 52
<211> LENGTH: 21
<212> TYPE: DNA
<213> ORGANISM: Homo sapiens

<400> SEQUENCE: 52
tgctagggcc gagtaatcat c                                         21

<210> SEQ ID NO 53
<211> LENGTH: 60
<212> TYPE: DNA
<213> ORGANISM: Homo sapiens

<400> SEQUENCE: 53
tatatttaaa aatacatact ggtatacatc gatctcatga ctttgctatt atgcatagtg    60

<210> SEQ ID NO 54
<211> LENGTH: 60
<212> TYPE: DNA
<213> ORGANISM: Homo sapiens

<400> SEQUENCE: 54
ccccagccca gcaacctggc tcacctgatc gagtacatct tcaagccatc ctgtgtgccc    60

<210> SEQ ID NO 55
<211> LENGTH: 60

```
<212> TYPE: DNA
<213> ORGANISM: Homo sapiens

<400> SEQUENCE: 55
tataaataat acagctctat ttgcctactc gattaaagaa tcatattata tccttaattc    60

<210> SEQ ID NO 56
<211> LENGTH: 60
<212> TYPE: DNA
<213> ORGANISM: Homo sapiens

<400> SEQUENCE: 56
cactatgcat aatagcaaag tcatgagatc gaaaatgttt gtcaagcagt aggttttggg    60

<210> SEQ ID NO 57
<211> LENGTH: 60
<212> TYPE: DNA
<213> ORGANISM: Homo sapiens

<400> SEQUENCE: 57
gattttagaa tctctaacaa ggctgcaatc gaggttagct gctgcagaaa gaagagaaaa    60

<210> SEQ ID NO 58
<211> LENGTH: 60
<212> TYPE: DNA
<213> ORGANISM: Homo sapiens

<400> SEQUENCE: 58
ggtgactaaa atgagattgc attttctttc gaccatttgg ccagcatgcc aaacactggt    60

<210> SEQ ID NO 59
<211> LENGTH: 60
<212> TYPE: DNA
<213> ORGANISM: Homo sapiens

<400> SEQUENCE: 59
taacctctcc tttcttaggt tctccatatc gatagaaaat tgtctgcagc ccttaatgcc    60

<210> SEQ ID NO 60
<211> LENGTH: 60
<212> TYPE: DNA
<213> ORGANISM: Homo sapiens

<400> SEQUENCE: 60
agctcacggt cagtgccgtt ccgtttgctc gaataaagaa caaggacctt aaaaaataga    60

<210> SEQ ID NO 61
<211> LENGTH: 60
<212> TYPE: DNA
<213> ORGANISM: Homo sapiens

<400> SEQUENCE: 61
aaagtcatac aactactatg taagatattc gaatacctgt tagaataggt gaaggtttat    60

<210> SEQ ID NO 62
<211> LENGTH: 60
<212> TYPE: DNA
<213> ORGANISM: Homo sapiens

<400> SEQUENCE: 62
tatatttaaa aatacatact ggtatacatc gatctcatga ctttgctatt atgcatagtg    60

<210> SEQ ID NO 63
```

```
<211> LENGTH: 60
<212> TYPE: DNA
<213> ORGANISM: Homo sapiens

<400> SEQUENCE: 63
ccccagccca gcaacctggc tcacctgatc gagtacatct tcaagccatc ctgtgtgccc    60

<210> SEQ ID NO 64
<211> LENGTH: 60
<212> TYPE: DNA
<213> ORGANISM: Homo sapiens

<400> SEQUENCE: 64
cactatgcat aatagcaaag tcatgagatc gaaaatgttt gtcaagcagt aggttttggg    60

<210> SEQ ID NO 65
<211> LENGTH: 60
<212> TYPE: DNA
<213> ORGANISM: Homo sapiens

<400> SEQUENCE: 65
gattttagaa tctctaacaa ggctgcaatc gaggttagct gctgcagaaa gaagagaaaa    60

<210> SEQ ID NO 66
<211> LENGTH: 60
<212> TYPE: DNA
<213> ORGANISM: Homo sapiens

<400> SEQUENCE: 66
ggtgactaaa atgagattgc attttctttc gaccatttgg ccagcatgcc aaacactggt    60

<210> SEQ ID NO 67
<211> LENGTH: 60
<212> TYPE: DNA
<213> ORGANISM: Homo sapiens

<400> SEQUENCE: 67
taacctctcc tttcttaggt tctccatatc gatagaaaat tgtctgcagc ccttaatgcc    60

<210> SEQ ID NO 68
<211> LENGTH: 60
<212> TYPE: DNA
<213> ORGANISM: Homo sapiens

<400> SEQUENCE: 68
agctcacggt cagtgccgtt ccgtttgctc gaataaagaa caaggacctt aaaaaataga    60

<210> SEQ ID NO 69
<211> LENGTH: 60
<212> TYPE: DNA
<213> ORGANISM: Homo sapiens

<400> SEQUENCE: 69
aaagtcatac aactactatg taagatattc gaatacctgt tagaataggt gaaggtttat    60

<210> SEQ ID NO 70
<211> LENGTH: 22
<212> TYPE: DNA
<213> ORGANISM: Homo sapiens

<400> SEQUENCE: 70
gcagcacaca gggaactctc tt                                             22
```

-continued

```
<210> SEQ ID NO 71
<211> LENGTH: 20
<212> TYPE: DNA
<213> ORGANISM: Homo sapiens

<400> SEQUENCE: 71
gctaggaagg gcctgggatg                                              20

<210> SEQ ID NO 72
<211> LENGTH: 25
<212> TYPE: DNA
<213> ORGANISM: Homo sapiens

<400> SEQUENCE: 72
tccaaaatgt ttaatactgc ctaga                                        25

<210> SEQ ID NO 73
<211> LENGTH: 20
<212> TYPE: DNA
<213> ORGANISM: Homo sapiens

<400> SEQUENCE: 73
cagccactgt agagagcagt                                              20

<210> SEQ ID NO 74
<211> LENGTH: 24
<212> TYPE: DNA
<213> ORGANISM: Homo sapiens

<400> SEQUENCE: 74
acttcttccc aagtcacttt ttgc                                         24

<210> SEQ ID NO 75
<211> LENGTH: 22
<212> TYPE: DNA
<213> ORGANISM: Homo sapiens

<400> SEQUENCE: 75
tgacgaagaa gcaatccctg gt                                           22

<210> SEQ ID NO 76
<211> LENGTH: 24
<212> TYPE: DNA
<213> ORGANISM: Homo sapiens

<400> SEQUENCE: 76
aatctctgcc ctcctctcat cttg                                         24

<210> SEQ ID NO 77
<211> LENGTH: 20
<212> TYPE: DNA
<213> ORGANISM: Homo sapiens

<400> SEQUENCE: 77
aggtatgcag ccagcctgag                                              20

<210> SEQ ID NO 78
<211> LENGTH: 25
<212> TYPE: DNA
<213> ORGANISM: Homo sapiens

<400> SEQUENCE: 78
ccgtgccata tcctctgatt tatgc                                        25
```

```
<210> SEQ ID NO 79
<211> LENGTH: 23
<212> TYPE: DNA
<213> ORGANISM: Homo sapiens

<400> SEQUENCE: 79
ttgttgagcc cagcaattcc ttt                                              23

<210> SEQ ID NO 80
<211> LENGTH: 20
<212> TYPE: DNA
<213> ORGANISM: Homo sapiens

<400> SEQUENCE: 80
ctcagtgggc acacactcca                                                  20

<210> SEQ ID NO 81
<211> LENGTH: 20
<212> TYPE: DNA
<213> ORGANISM: Homo sapiens

<400> SEQUENCE: 81
agccatgtgg tctggaatct                                                  20

<210> SEQ ID NO 82
<211> LENGTH: 20
<212> TYPE: DNA
<213> ORGANISM: Homo sapiens

<400> SEQUENCE: 82
taacccacca gcagcaaggt                                                  20

<210> SEQ ID NO 83
<211> LENGTH: 20
<212> TYPE: DNA
<213> ORGANISM: Homo sapiens

<400> SEQUENCE: 83
tggccatctt gctttgcctc                                                  20

<210> SEQ ID NO 84
<211> LENGTH: 21
<212> TYPE: DNA
<213> ORGANISM: Homo sapiens

<400> SEQUENCE: 84
ggacctacct ccactgggtt g                                                21

<210> SEQ ID NO 85
<211> LENGTH: 24
<212> TYPE: DNA
<213> ORGANISM: Homo sapiens

<400> SEQUENCE: 85
catgttccca cagcaaggaa gtta                                             24

<210> SEQ ID NO 86
<211> LENGTH: 20
<212> TYPE: DNA
<213> ORGANISM: Homo sapiens

<400> SEQUENCE: 86
tttccgtgcc agtgtcctgt                                                  20
```

<210> SEQ ID NO 87
<211> LENGTH: 22
<212> TYPE: DNA
<213> ORGANISM: Homo sapiens

<400> SEQUENCE: 87
ggctgacctt caacagattc gc                                          22

<210> SEQ ID NO 88
<211> LENGTH: 20
<212> TYPE: DNA
<213> ORGANISM: Homo sapiens

<400> SEQUENCE: 88
tcttgtacac ggttggtggt                                             20

<210> SEQ ID NO 89
<211> LENGTH: 24
<212> TYPE: DNA
<213> ORGANISM: Homo sapiens

<400> SEQUENCE: 89
tgtcacctat gtgctgagta ctgg                                        24

<210> SEQ ID NO 90
<211> LENGTH: 22
<212> TYPE: DNA
<213> ORGANISM: Homo sapiens

<400> SEQUENCE: 90
tgacgaagaa gcaatccctg gt                                          22

<210> SEQ ID NO 91
<211> LENGTH: 21
<212> TYPE: DNA
<213> ORGANISM: Homo sapiens

<400> SEQUENCE: 91
ggacctacct ccactgggtt g                                           21

<210> SEQ ID NO 92
<211> LENGTH: 25
<212> TYPE: DNA
<213> ORGANISM: Homo sapiens

<400> SEQUENCE: 92
ccgtgccata tcctctgatt tatgc                                       25

<210> SEQ ID NO 93
<211> LENGTH: 22
<212> TYPE: DNA
<213> ORGANISM: Homo sapiens

<400> SEQUENCE: 93
ggctgacctt caacagattc gc                                          22

<210> SEQ ID NO 94
<211> LENGTH: 24
<212> TYPE: DNA
<213> ORGANISM: Homo sapiens

<400> SEQUENCE: 94
acttcttccc aagtcacttt ttgc                                    24

<210> SEQ ID NO 95
<211> LENGTH: 20
<212> TYPE: DNA
<213> ORGANISM: Homo sapiens

<400> SEQUENCE: 95
tggccatctt gctttgcctc                                         20

<210> SEQ ID NO 96
<211> LENGTH: 25
<212> TYPE: DNA
<213> ORGANISM: Homo sapiens

<400> SEQUENCE: 96
ggatatgcag ttttcctggc actac                                   25

<210> SEQ ID NO 97
<211> LENGTH: 24
<212> TYPE: DNA
<213> ORGANISM: Homo sapiens

<400> SEQUENCE: 97
catgctaggg ccgagtaatc atct                                    24

<210> SEQ ID NO 98
<211> LENGTH: 22
<212> TYPE: DNA
<213> ORGANISM: Homo sapiens

<400> SEQUENCE: 98
gcagcacaca gggaactctc tt                                      22

<210> SEQ ID NO 99
<211> LENGTH: 23
<212> TYPE: DNA
<213> ORGANISM: Homo sapiens

<400> SEQUENCE: 99
ttgttgagcc cagcaattcc ttt                                     23

<210> SEQ ID NO 100
<211> LENGTH: 20
<212> TYPE: DNA
<213> ORGANISM: Homo sapiens

<400> SEQUENCE: 100
cagccactgt agagagcagt                                         20

<210> SEQ ID NO 101
<211> LENGTH: 20
<212> TYPE: DNA
<213> ORGANISM: Homo sapiens

<400> SEQUENCE: 101
taacccacca gcagcaaggt                                         20

<210> SEQ ID NO 102
<211> LENGTH: 25
<212> TYPE: DNA
<213> ORGANISM: Homo sapiens

<400> SEQUENCE: 102
agtagcttcc ctgttagagg tcttg                                           25

<210> SEQ ID NO 103
<211> LENGTH: 23
<212> TYPE: DNA
<213> ORGANISM: Homo sapiens

<400> SEQUENCE: 103
agccagtgac tccacaactt ctt                                             23

<210> SEQ ID NO 104
<211> LENGTH: 28
<212> TYPE: DNA
<213> ORGANISM: Homo sapiens

<400> SEQUENCE: 104
aggttgcttt cgaagtacag atatcact                                        28

<210> SEQ ID NO 105
<211> LENGTH: 26
<212> TYPE: DNA
<213> ORGANISM: Homo sapiens

<400> SEQUENCE: 105
attttctttc gaccatttgg ccagca                                          26

<210> SEQ ID NO 106
<211> LENGTH: 31
<212> TYPE: DNA
<213> ORGANISM: Homo sapiens

<400> SEQUENCE: 106
ttctaacagg tattcgaata tcttacatag t                                    31

<210> SEQ ID NO 107
<211> LENGTH: 27
<212> TYPE: DNA
<213> ORGANISM: Homo sapiens

<400> SEQUENCE: 107
aagtaacatt cgacaaacct ctggtaa                                         27

<210> SEQ ID NO 108
<211> LENGTH: 27
<212> TYPE: DNA
<213> ORGANISM: Homo sapiens

<400> SEQUENCE: 108
tattctcttt gatcgaggca tatagct                                         27

<210> SEQ ID NO 109
<211> LENGTH: 29
<212> TYPE: DNA
<213> ORGANISM: Homo sapiens

<400> SEQUENCE: 109
aaagtcatga gatcgatgta taccagtat                                       29

<210> SEQ ID NO 110
<211> LENGTH: 28
<212> TYPE: DNA
<213> ORGANISM: Homo sapiens

```
<400> SEQUENCE: 110
ttgacaaaca ttttcgatct catgactt                                28

<210> SEQ ID NO 111
<211> LENGTH: 25
<212> TYPE: DNA
<213> ORGANISM: Homo sapiens

<400> SEQUENCE: 111
tgtggctcag tcgacagaaa gtaca                                   25

<210> SEQ ID NO 112
<211> LENGTH: 20
<212> TYPE: DNA
<213> ORGANISM: Homo sapiens

<400> SEQUENCE: 112
tcttgtacac ggttggtggt                                         20

<210> SEQ ID NO 113
<211> LENGTH: 25
<212> TYPE: DNA
<213> ORGANISM: Homo sapiens

<400> SEQUENCE: 113
ggatatgcag ttttcctggc actac                                   25

<210> SEQ ID NO 114
<211> LENGTH: 25
<212> TYPE: DNA
<213> ORGANISM: Homo sapiens

<400> SEQUENCE: 114
agtagcttcc ctgttagagg tcttg                                   25

<210> SEQ ID NO 115
<211> LENGTH: 24
<212> TYPE: DNA
<213> ORGANISM: Homo sapiens

<400> SEQUENCE: 115
tgtcacctat gtgctgagta ctgg                                    24

<210> SEQ ID NO 116
<211> LENGTH: 24
<212> TYPE: DNA
<213> ORGANISM: Homo sapiens

<400> SEQUENCE: 116
catgctaggg ccgagtaatc atct                                    24

<210> SEQ ID NO 117
<211> LENGTH: 23
<212> TYPE: DNA
<213> ORGANISM: Homo sapiens

<400> SEQUENCE: 117
agccagtgac tccacaactt ctt                                     23

<210> SEQ ID NO 118
<211> LENGTH: 60
<212> TYPE: DNA
<213> ORGANISM: Homo sapiens
```

<400> SEQUENCE: 118
agatctagtt cacagtagca ccaatatatc gacagatagc tgacatcatc ctcccaatgt    60

<210> SEQ ID NO 119
<211> LENGTH: 60
<212> TYPE: DNA
<213> ORGANISM: Homo sapiens

<400> SEQUENCE: 119
agagtacttc ctaactccta ctgtacactc gacagatagc tgacatcatc ctcccaatgt    60

<210> SEQ ID NO 120
<211> LENGTH: 60
<212> TYPE: DNA
<213> ORGANISM: Homo sapiens

<400> SEQUENCE: 120
tataaccagt gctcctacga aggccgcttc gaagtctcaa acttcacttc tcctgtgcgc    60

<210> SEQ ID NO 121
<211> LENGTH: 60
<212> TYPE: DNA
<213> ORGANISM: Homo sapiens

<400> SEQUENCE: 121
agagtacttc ctaactccta ctgtacactc gaggatgatc gctccgacag ctcctccagc    60

<210> SEQ ID NO 122
<211> LENGTH: 60
<212> TYPE: DNA
<213> ORGANISM: Homo sapiens

<400> SEQUENCE: 122
gggtttcgcc atgttggcca ggctggtctc gaagttgatg catctgtgct cacgtttgca    60

<210> SEQ ID NO 123
<211> LENGTH: 60
<212> TYPE: DNA
<213> ORGANISM: Homo sapiens

<400> SEQUENCE: 123
agatctagtt cacagtagca ccaatatatc gactgtctcc tgttggccat ctctcaccct    60

<210> SEQ ID NO 124
<211> LENGTH: 60
<212> TYPE: DNA
<213> ORGANISM: Homo sapiens

<400> SEQUENCE: 124
agatctagtt cacagtagca ccaatatatc gaactcctga ccttgtgatc cacccacctc    60

<210> SEQ ID NO 125
<211> LENGTH: 26
<212> TYPE: DNA
<213> ORGANISM: Homo sapiens

<400> SEQUENCE: 125
gaatacccag gaatgcttac ttgagc                                         26

<210> SEQ ID NO 126
<211> LENGTH: 26
<212> TYPE: DNA

```
<213> ORGANISM: Homo sapiens

<400> SEQUENCE: 126
accaaatgcc atctgggaca catcca                                              26

<210> SEQ ID NO 127
<211> LENGTH: 23
<212> TYPE: DNA
<213> ORGANISM: Homo sapiens

<400> SEQUENCE: 127
cccgctaagt ccacccctct gta                                                 23

<210> SEQ ID NO 128
<211> LENGTH: 26
<212> TYPE: DNA
<213> ORGANISM: Homo sapiens

<400> SEQUENCE: 128
agtctgccca ctgaggtaac taacaa                                              26

<210> SEQ ID NO 129
<211> LENGTH: 26
<212> TYPE: DNA
<213> ORGANISM: Homo sapiens

<400> SEQUENCE: 129
gattccagcc acccacctttt cacaag                                             26

<210> SEQ ID NO 130
<211> LENGTH: 26
<212> TYPE: DNA
<213> ORGANISM: Homo sapiens

<400> SEQUENCE: 130
tgattccagc cacccacctt tcacaa                                              26

<210> SEQ ID NO 131
<211> LENGTH: 23
<212> TYPE: DNA
<213> ORGANISM: Homo sapiens

<400> SEQUENCE: 131
gaaccgcact taccctcagc agt                                                 23

<210> SEQ ID NO 132
<211> LENGTH: 26
<212> TYPE: DNA
<213> ORGANISM: Homo sapiens

<400> SEQUENCE: 132
ggacaagcag acacactacc tgaact                                              26

<210> SEQ ID NO 133
<211> LENGTH: 26
<212> TYPE: DNA
<213> ORGANISM: Homo sapiens

<400> SEQUENCE: 133
atcccctgaa acagaaggac ctcgtg                                              26

<210> SEQ ID NO 134
<211> LENGTH: 26
```

```
<212> TYPE: DNA
<213> ORGANISM: Homo sapiens

<400> SEQUENCE: 134
gagccgtctc ataataacct cagggt                                          26

<210> SEQ ID NO 135
<211> LENGTH: 26
<212> TYPE: DNA
<213> ORGANISM: Homo sapiens

<400> SEQUENCE: 135
cagtggttta gggcaaagag agggag                                          26

<210> SEQ ID NO 136
<211> LENGTH: 60
<212> TYPE: DNA
<213> ORGANISM: Homo sapiens

<400> SEQUENCE: 136
agatctagtt cacagtagca ccaatatatc gacattaagt tcatgagagt cttctatatt     60

<210> SEQ ID NO 137
<211> LENGTH: 60
<212> TYPE: DNA
<213> ORGANISM: Homo sapiens

<400> SEQUENCE: 137
gcgcacagga gaagtgaagt ttgagacttc gaaaaaggaa taaattgaaa aatagaggaa     60

<210> SEQ ID NO 138
<211> LENGTH: 60
<212> TYPE: DNA
<213> ORGANISM: Homo sapiens

<400> SEQUENCE: 138
agagtacttc ctaactccta ctgtacactc gatgttttgg gtattgaatg tggtaagtgg     60

<210> SEQ ID NO 139
<211> LENGTH: 60
<212> TYPE: DNA
<213> ORGANISM: Homo sapiens

<400> SEQUENCE: 139
atcaagactg tatggtactg gcacaggatc gaggatgatc gctccgacag ctcctccagc     60

<210> SEQ ID NO 140
<211> LENGTH: 60
<212> TYPE: DNA
<213> ORGANISM: Homo sapiens

<400> SEQUENCE: 140
atcaagactg tatggtactg gcacaggatc gatgttttgg gtattgaatg tggtaagtgg     60

<210> SEQ ID NO 141
<211> LENGTH: 60
<212> TYPE: DNA
<213> ORGANISM: Homo sapiens

<400> SEQUENCE: 141
atcaagactg tatggtactg gcacaggatc gacattaagt tcatgagagt cttctatatt     60

<210> SEQ ID NO 142
```

```
<211> LENGTH: 60
<212> TYPE: DNA
<213> ORGANISM: Homo sapiens

<400> SEQUENCE: 142
tgtccagtta aattgcagat atttccgatc gagtgtacag taggagttag gaagtactct    60

<210> SEQ ID NO 143
<211> LENGTH: 60
<212> TYPE: DNA
<213> ORGANISM: Homo sapiens

<400> SEQUENCE: 143
atcaagactg tatggtactg gcacaggatc gaactcctga ccttgtgatc cacccacctc    60

<210> SEQ ID NO 144
<211> LENGTH: 60
<212> TYPE: DNA
<213> ORGANISM: Homo sapiens

<400> SEQUENCE: 144
agatctagtt cacagtagca ccaatatatc gaatctgggt gtttcaaaga catcaacaaa    60

<210> SEQ ID NO 145
<211> LENGTH: 60
<212> TYPE: DNA
<213> ORGANISM: Homo sapiens

<400> SEQUENCE: 145
agatctagtt cacagtagca ccaatatatc gaggatgatc gctccgacag ctcctccagc    60

<210> SEQ ID NO 146
<211> LENGTH: 60
<212> TYPE: DNA
<213> ORGANISM: Homo sapiens

<400> SEQUENCE: 146
gggtttcacc atgttggcca ggatggtctc gaactcctga ccttgtgatc cacccacctc    60

<210> SEQ ID NO 147
<211> LENGTH: 60
<212> TYPE: DNA
<213> ORGANISM: Homo sapiens

<400> SEQUENCE: 147
agatctagtt cacagtagca ccaatatatc gaagcggcct tcgtaggagc actggttata    60

<210> SEQ ID NO 148
<211> LENGTH: 60
<212> TYPE: DNA
<213> ORGANISM: Homo sapiens

<400> SEQUENCE: 148
agatctagtt cacagtagca ccaatatatc gactaaggtc agccctccgt gctgggggct    60

<210> SEQ ID NO 149
<211> LENGTH: 23
<212> TYPE: DNA
<213> ORGANISM: Homo sapiens

<400> SEQUENCE: 149
ggtccagaga accgcactta ccc                                            23
```

```
<210> SEQ ID NO 150
<211> LENGTH: 26
<212> TYPE: DNA
<213> ORGANISM: Homo sapiens

<400> SEQUENCE: 150
tccctctcag aatcctactt ggcttc                                          26

<210> SEQ ID NO 151
<211> LENGTH: 26
<212> TYPE: DNA
<213> ORGANISM: Homo sapiens

<400> SEQUENCE: 151
gaacagtttg tgggtagtat gcggtc                                          26

<210> SEQ ID NO 152
<211> LENGTH: 26
<212> TYPE: DNA
<213> ORGANISM: Homo sapiens

<400> SEQUENCE: 152
tctggacaag gtatctggaa ggctga                                          26

<210> SEQ ID NO 153
<211> LENGTH: 26
<212> TYPE: DNA
<213> ORGANISM: Homo sapiens

<400> SEQUENCE: 153
gcactgctcg caatagccaa gaacta                                          26

<210> SEQ ID NO 154
<211> LENGTH: 23
<212> TYPE: DNA
<213> ORGANISM: Homo sapiens

<400> SEQUENCE: 154
cttgctgacc ctcctatgga tgg                                             23

<210> SEQ ID NO 155
<211> LENGTH: 26
<212> TYPE: DNA
<213> ORGANISM: Homo sapiens

<400> SEQUENCE: 155
gcacagagtt ccaacatttc ctccac                                          26

<210> SEQ ID NO 156
<211> LENGTH: 26
<212> TYPE: DNA
<213> ORGANISM: Homo sapiens

<400> SEQUENCE: 156
ggacaagcag acacactacc tgaact                                          26

<210> SEQ ID NO 157
<211> LENGTH: 26
<212> TYPE: DNA
<213> ORGANISM: Homo sapiens

<400> SEQUENCE: 157
gcactgctcg caatagccaa gaacta                                          26
```

<210> SEQ ID NO 158
<211> LENGTH: 26
<212> TYPE: DNA
<213> ORGANISM: Homo sapiens

<400> SEQUENCE: 158
acagtggttt agggcaaaga gaggga                                              26

<210> SEQ ID NO 159
<211> LENGTH: 26
<212> TYPE: DNA
<213> ORGANISM: Homo sapiens

<400> SEQUENCE: 159
gaagaagcct ctgtttggtc tggaaa                                              26

<210> SEQ ID NO 160
<211> LENGTH: 26
<212> TYPE: DNA
<213> ORGANISM: Homo sapiens

<400> SEQUENCE: 160
ggaaggacaa gcagacacac tacctg                                              26

<210> SEQ ID NO 161
<211> LENGTH: 26
<212> TYPE: DNA
<213> ORGANISM: Homo sapiens

<400> SEQUENCE: 161
gtggtttagg gcaaagagag ggagat                                              26

<210> SEQ ID NO 162
<211> LENGTH: 25
<212> TYPE: DNA
<213> ORGANISM: Homo sapiens

<400> SEQUENCE: 162
tccccgagtc ctgtgatggc aaact                                               25

<210> SEQ ID NO 163
<211> LENGTH: 25
<212> TYPE: DNA
<213> ORGANISM: Homo sapiens

<400> SEQUENCE: 163
atggctacgg aaagggcatt cggac                                               25

<210> SEQ ID NO 164
<211> LENGTH: 800
<212> TYPE: DNA
<213> ORGANISM: Homo sapiens

<400> SEQUENCE: 164
ttgggcaaat tacttattct gtatgagttt cagtgtgcac attcaccaaa tgtggataat         60
aataatggtt aactcctagg atgtttgtga gaattgaaat aatatatcat tcttagccca        120
gtataatcat ttaaattttt tttttagtaa gcattagctg gaatcattgg tattgttttt        180
attttcttat ctaccctcaa acattgaaag tgtcttggag cagaagttgt atattacata        240 cttttcagaat ctctctacca tggggccttt tgctttaatt aatttctgct ataattaatt      300
gctctattat gccatttcct gatttcatcc aagacacact ctaaatgtat atgacgaaga        360

```
agcaatccct ggtgactaaa atgagattgc attttctttc gaccatttgg ccagcatgcc        420
aaacactggt aaattggcat tccaaagctc acattggctg attgataaat tcactacttt        480
gggctcagtt ttgccatctg taaagtgatg gtgatcaaat gagcaagtgt atttatttat        540
tttaaaaata ctttattt agattttggg atacatgtgt aagtttgcta tataggtaaa         600
ttcatgtcat gggagtttat tgtaaagatt atttcatcat ccaggtacta agcctagtac        660
acaatagtta ttttttttct gattcttttc ctcctcccaa cttcaaccca gtggaggtag        720
gtcccagtgt ctgttgtccc cctctttgtg tccatgtgtt ctcatcattt agcccccact        780
tataagtgat aatatgtggt                                                    800
```